US011690884B2

(12) United States Patent
Im et al.

(10) Patent No.: US 11,690,884 B2
(45) Date of Patent: Jul. 4, 2023

(54) LACTOBACILLUS PLANT ARUM STRAIN, POLYSACCHARIDES DERIVED FROM STRAIN, AND USE THEREOF

(71) Applicant: IMMUNOBIOME INC., Gyeongsangbuk-do (KR)

(72) Inventors: Sin-Hyeog Im, Gyeongsangbuk-do (KR); Garima Sharma, Gyeongsangbuk-do (KR); Sun-Hee Park, Gyeongsangbuk-do (KR); Amit Sharma, Gyeongsangbuk-do (KR)

(73) Assignee: IMMUNOBIOME INC., Gyeongbuk (KR)

( * ) Notice: Subject to any disclaimer, the term of this patent is extended or adjusted under 35 U.S.C. 154(b) by 0 days.

(21) Appl. No.: 17/811,542

(22) Filed: Jul. 8, 2022

(65) Prior Publication Data

US 2022/0370525 A1 Nov. 24, 2022

Related U.S. Application Data

(63) Continuation of application No. PCT/KR2021/000351, filed on Jan. 11, 2021.

(30) Foreign Application Priority Data

Jan. 10, 2020 (KR) ........................ 10-2020-0003493

(51) Int. Cl.

| | |
|---|---|
| ***A61K 35/747*** | (2015.01) |
| ***A23L 33/135*** | (2016.01) |
| ***A61P 35/00*** | (2006.01) |
| ***C12N 1/20*** | (2006.01) |
| *C12R 1/25* | (2006.01) |

(52) U.S. Cl.

CPC .......... *A61K 35/747* (2013.01); *A23L 33/135* (2016.08); *A61P 35/00* (2018.01); *C12N 1/205* (2021.05); *C12R 2001/25* (2021.05)

(58) Field of Classification Search

CPC ..... C12N 1/205; A61K 35/747; A61K 35/745

See application file for complete search history.

(56) References Cited

U.S. PATENT DOCUMENTS

2019/0307794 A1 10/2019 Hong et al.

FOREIGN PATENT DOCUMENTS

| | | | |
|---|---|---|---|
| JP | 2012533319 | A | 12/2012 |
| JP | 2014511856 | A | 5/2014 |
| JP | 2016155851 | A | 9/2016 |
| JP | 201890605 | A | 6/2018 |
| KR | 1020160112699 | A | 9/2016 |
| KR | 101761186 | B1 | 7/2017 |
| KR | 101919938 | B1 | 11/2018 |
| KR | 1020180136395 | A | 12/2018 |
| KR | 1020200043266 | A | 4/2020 |

OTHER PUBLICATIONS

Behera, S.S., et al., "Lactobacillus plantarum with Functional Properties: An Approach to Increase Safety and Shelf-Life of Fermented Foods", BioMed Research International, 2018, https://doi.10.1155/2018/9361614, No. 9361614, Publisher: Hindawi.

Bock, K., et al., "CARBON-13 Nuclear Magnetic Resonance Spectroscopy of Monosaccharides", Advances in Carbohydrate Chemistry and Biochemistry, 1983, pp. 27-66, vol. 41, Publisher: Adademic Press, Inc.

Bover-Cid, S., et al., "Improved screening procedure for biogenic amine production by lactic acid bacteria", International Journal of Food Microbiology, 1999, pp. 33-41, vol. 53, Publisher: Elsevier.

Brubaker, S.W., et al., "Innate Immune Pattern Recognition: A Cell Biological Perspective", The Annual Review of Immunology, 2015, pp. 257-290; doi:10.1146/annurev-immunol-032414-112240, vol. 33, No. 10, Publisher Reviews in Advance.

Cerf-Bensussan, N., et al., "The immune system and the gut microbiota: friends or foes?", Nature Reviews Immunology, 2010, pp. 735-744, vol. 10, No. 10, Publisher: Macmillan Publishers Limited.

Cheigh, H-S, et al., "Biochemical, microbiological, and nutritional aspects of kimchi (Korean fermented vegetable products)", Critical Reviews in Food Science and Nutrition, 1994, pp. 175-203, vol. 34, No. 2.

Cheng, H., et al., "Macrophage Polarization in the Development and Progression of Ovarian Cancers: An Overview", Frontiers in Oncology, 2019, doi:1013389/fonc.2019.00421, vol. 9, No. 421.

Clemente, J.C., et al., "The Impact of the Gut Microbiota on Human Health: An Integrative View", Cell, 2012, pp. 1258-1270; DOI 10.1016/j.cell.2012.01.035, vol. 148, Publisher: Elsevier.

(Continued)

*Primary Examiner* — Thane Underdahl

(74) *Attorney, Agent, or Firm* — Hultquist, PLLC; Steven J. Hultquist

(57) ABSTRACT

The present invention relates to a novel *Lactobacillus plantarum* IMB19 strain, polysaccharides derived from the strain, and a use thereof. A novel *Lactobacillus plantarum* IMB19 strain and polysaccharides derived from the strain of the present invention exhibit an excellent CD8+T cell activity stimulating ability and Treg cell inhibitory activity, and stimulate and improve an antitumor immune response through various mechanisms such as increased macrophage infiltration in CPS tumors and differentiation and reprogramming of macrophages into an inflammatory phenotype (M1). Therefore, a strain and polysaccharides derived from the strain of the present invention can be effectively used for immune regulation, especially immune boosting, in a subject, and can inhibit tumor growth by inducing and enhancing an antitumor immune response. A novel strain and polysaccharides derived from the strain of the present invention are useful in the prevention, alleviation or treatment of such as tumors, infectious diseases and various immune diseases that are the cause of or symptom of immune dysfunction.

19 Claims, 21 Drawing Sheets

Specification includes a Sequence Listing.

(56) References Cited

OTHER PUBLICATIONS

Dela Cruz, T.E., et al., "Gelatin Hydrolysis Test Protocol", American Society for Microbiology, 2012, pp. 1-10.
Grimstrup, K., et al., "Real-Time Whole-Genome Sequencing for Routine Typing, Surveillance, and Outbreak Detection of Verotoxigenic *Escherichia coli*", J.Clin. Microbiol., 2014, pp. 1501; DOI:10.1128/JCM.03617-13, vol. 52, No. 5.
Hill, C., et al., "The International Scientific Association for Probiotics and Prebiotics consensus statement on the scope and appropriate use of the term probiotic", Nat. Rev. Gastroenterol. Hepatol., 2014, pp. 506-514, vol. 11, Publisher: Macmillan Publishers Limited.
Iliev, I.D., et al., "Fungal dysbiosis: immunity and interactions at mucosal barriers", Nature Reviews Immunology, 2017, pp. 635-646; doi.10.1038/nn.2017.55, vol. 17, No. 10, Publisher: Macmillan Publishers Limited.
Kimura, A., et al., "IL-6: Regulator of Treg/Th17 balance", Eur. J. Immunol., 2010, pp. 1830-1835, vol. 40, Publisher: WILEY-VCH Verlag GmbH & Co.
Lanitis, "Mechanisms regulating T-cell infiltration and activity in solid tumors", Annals of Oncology, 2017, doi.10.1093/annonc/mdx238, vol. 28, Publisher: Oxford University Press.
Lee, J-S, et al., "Analysis of kimchi micrflora using denaturing gradient gel electrophoresis", International Journal of Food Microbiology, 2005, pp. 143-150, vol. 102, Publisher: Elsevier.
Lee, K., et al., "Effect of Lactobacillus plantarum as a Starter on the Food Quality and Microbiota of Kimchi", Food Sci. Biotechnol., 2010, pp. 641-646, vol. 19, No. 3.
Lee, Y.K., et al., "Has the Microbiota Played a Critical Role in the Evolution of the Adaptive Immune System?", Science, 2010, pp. 1768-1773, vol. 330.
Li, Q., et al., "Mechanism of action differences in the antitumor effects of transmembrane and secretory tumor necrosis factor-alpha in viro and in vivo", Cancer Immunol Immunother, 2006, pp. 1470-1479; DOI 10.1007/s00262-006-0150-x, vol. 55.
Mazmanian, S.K., et al., "A microbial symbiosis factor prevents intestinal inflammatory disease", Nature, 2008, doi: 10.1038/nature07008, vol. 453, Publisher: Nature Publishing Group.
Pessione, E., "Lactic acid bacteria contribution to gut microbiota complexity: lights and shadows", Frontiers in Cellular and Infection Microbiology, 2012, doi:10.3389/fcimb.2012.00086, vol. 2, No. 86.
Routy, B., et al., "Gut microbiome influences efficacy of PD-1-based immunotherapy against epithelial tumors", Science, 2017, 10.1126/science.aan3706, Publisher: www.sciencemag.org.
Scott, K.P., et al., "Manipulating the gut microbiota to maintain health and treat disease", Microbial Ecology in Health and Disease, 2015, pp. 25877; http:/dx.doi.org/10.3402/mehd.v26.25877, vol. 26.
Senchenkova, S.N., et al., "Structure of a highly phosphorylated O-polysaccharide of Proteus mirabilis 041", Carbbohydrate Research, 2004, pp. 1347-1352, vol. 339, Publisher: Elsevier.
Shashkov, A.S., et al., "Anionic Polymers of the Cell Wall of *Bacillus subtilis* subsp. subtilis VKM B-501T", Biochemistry (Moscow), 2009, pp. 543-548, vol. 74, Nos. Publisher: Pleiades Publishing, Ltd.
Sivan, A., et al., "Commensal Bifidobacterium promotes antitumor immunity and facilitates anti-PD-L1-efficacy", Sciencexpress, 2015, who10.1126/science.aad1329, Publisher: www.sciencemag.org.
Streshinskaya, G.M., et al., "Carbohydrate-Containing Cell Wall Polymers of Some Strains of the bacillus subtilis Group", Microbiology, 2011, pp. 21-29, vol. 80, No. 1, Publisher: Pleiades Publishing, Ltd.
Stubbendieck, R.M., et al., "Competition among Nasal Bacteria Suggests a Role for Siderophore-Mediated Interactions in Shaping the Human Nasal Microbiota", Applied and Environmental Microbiology, 2019, e02406, vol. 85, No. 10, Publisher: American Society for Microbiology.
Tan, T.G., et al., "Identifying species of symbiont bacteria from the human gut that, alone, can induce intestinal Th17 cells in mice", PNAS Early Edition, 2016, pp. E8141-E8150;www.pnas.org/cgi/doi/10.1073/pnas.1617460113, vol. 113, No. 50, Publisher: CrossMark.
Tomita, S., et al., "A rapid NMR-based method for discrimination of strain-specific cell wall teichoic acid structures reveals a third backbone type in Lactobacillus plantarum", FEMS Microbiology Letters, 2017, doi:10.1093/femsle/fnx034, vol. 364, Publisher: Journals Investing in Science.
Torriani, S., et al., "Differentiation of Lactobacillus plantarum, L. pentosus, and L. paraplantarum by recA Gene Sequence Analysis and Multiplex PCR Assay with recA Gene-Derived Primers", Applied and Environmental Microbiology, 2001, pp. 3450-3454, vol. 67, No. 8.
Underhill, D.M., et al., "The mycobiota: interactions between commensal fungi and the host immune system", Nature Reviews Immunology, 2014, pp. 405-416; doi:10.1038/nri3684, vol. 14, No. 6, Publisher: Macmillan Publishers Limited.
Valueva, O.A., et al., "Structures of cell-wall phosphate-containing glycooloymers Bifidobacterium longum BIM B-476-D", Carbohydrate Research, 2013, pp. 22-27, vol. 373, Publisher: Elsevier.
Verma, R., et al., "Cell surface plysaccharides of Bifidobacterium bifidum induce the generation Foxp3 regulatory T cells", Science Immunology, 2018, eaat6975; 1-14, vol. 3.
Vetizou, M., et al., "Anticancer immunotherapy by CTLA-4 blockade relies on the gut microbiota", Sciencexpress, 2015, 10.1126/science.aad1329, Publisher: www.sciencemag.org.
Viaud, S., et al., "The Intestinal Microbiota Modulates the Anticancer Immune Effects of Cyclophosphamide", Science, 2013, pp. 971-976; DOI 10.1126/science.1240537, vol. 342, Publisher: AAAS.
Wheeler, M.L., et al., "Immunity to Commensal Fungi: Detente and Disease", The Annual Review of Pathology Mechanisms of Disease, 2017, pp. 359-385, vol. 12, No. 14.
Korean Intellectual Property Office 071322 Office Action in KR101919938B1.
Korean Intellectual Property Office 071322 Office Action in KR101919938B1_English Translation.
Deng, H., et al., "A novel strain of Bacteroides fragilis enhances phagocytosis and polarises M1 macrophages", Scientific Reports, 2016, pp. DOI:10.1038/srep29401, vol. 6, No. 29401, Publisher: www.nature.com/scientificreports.
Garcia-Vello, P., et al., "Structural features and immunological perception of the cell surface glycans of Lactobacilllus plantarum: a novel rhamnose-rich polysaccharide and teichoic acids", Carbohydrate Polymers, 2020, pp. 1-9, vol. 233, No. 115857.
Remus, D.M., et al., "Impact of 4 Lactobacillus plantarum capsular polysaccharide clusters on surface glycan composition and host cell signaling", Microbial Cell Factories, 2012, pp. http://www.microbialcellfactories.com/11/1/149, vol. 11, No. 149, Publisher: BioMed Central.
Takano, T., et al., "Lactobacillus plantarum OLL2712 induces IL-10 production by intestinal dendritic cells", Bioscience of Microbiota, Food and Health, 2020, pp. 39-44, vol. 39, No. 2, Publisher: The Intestinal Microbiology Society.
Garcia-Vello, P., et al., "Structural features and immunological perception of the cell surface glycans of Lactobacilllus plantarum: a novel rhamnose-rich polysaccharide and teichoic acids", Carbohydrate Polymers, 2020, pp. 115857; https://doi.org/10.1016./j.carbpol.2020.115857, vol. 233, Publisher: Elsevier.
Office Action dated Dec. 7, 2022 in Counterpart JP Patent Application No. 2022542386.
English Translation of Office Action dated Dec. 7, 2022 in Counterpart JP Patent Application No. 2022542386.
Notice of Allowance issued in counterpart Korean Patent Application No. 10-2021-0003433 dated Feb. 28, 2023.
English Translation of Notice of Allowance issued in counterpart Korean Patent Application No. 10-2021-0003433 dated Feb. 28, 2023.
Mistou, M-Y, et al., "Bacterial gycobiology: rhamnose-containing cell wall polysaccharides in Gram-positive bacteria", FEMS Microbiology Reviews, 2016, pp. 464-479, vol. 40.

SEQUENCE LISTING

```
Sequence total quantity: 4
SEQ ID NO: 1          moltype = DNA  length = 20
FEATURE               Location/Qualifiers
source                1..20
                      mol_type = other DNA
                      organism = Synthetic construct
SEQUENCE: 1
agagtttgat cmtggctcag                                              20

SEQ ID NO: 2          moltype = DNA  length = 22
FEATURE               Location/Qualifiers
source                1..22
                      mol_type = other DNA
                      organism = Synthetic construct
```

```
SEQUENCE: 2
tacggytacc ttgttacgac tt                                          22

SEQ ID NO: 3           moltype = DNA  length = 1522
FEATURE                Location/Qualifiers
source                 1..1522
                       mol_type = other DNA
                       organism = Synthetic construct
SEQUENCE: 3
agcgctggga tgatgctagt gttggagggt ttccgccctt cagtgctgca gctaacgcat  60
taagcattcc gcctggggag tacggccgca aggctgaaac tcaaaggaat tgacgggggc  120
ccgcacaagc ggtggagcat gtggtttaat tcgaagctac gcgaagaacc ttaccaggtc  180
ttgacatact atgcaaatct aagagattag acgttccctt cggggacatg gatacaggtg  240
gtgcatggtt gtcgtcagct cgtgtcgtga gatgttgggt taagtcccgc aacgagcgca  300
acccttatta tcagttgcca gcattaagtt gggcactctg gtgagactgc cggtgacaaa  360
ccggaggaag gtggggatga cgtcaaatca tcatgcccct tatgacctgg gctacacacg  420
tgctacaatg gatggtacaa cgagttgcga actcgcgaga gtaagctaat ctcttaaagc  480
cattctcagt tcggattgta ggctgcaact cgcctacatg aagtcggaat cgctagtaat  540
cgcggatcag catgccgcgg tgaatacgtt cccgggcctt gtacacaccg cccgtcacac  600
catgagagtt tgtaacaccc aaagtcggtg gggtaacctt ttaggaacca gccgcctaag  660
gtgggacaga tgattagggt gaagtcgtaa cagggtaaaa ccgtaaagat gttcaacccg  720
ccacatctgt cgcgtctccg tcgtagatat aagaaagcca aagggccttt cttccatggc  780
tgggtgttca tgcaataaca tcgaccggtt atccacgaca caagaaagga ttacgttggt  840
cctggttgtg cgctcaggtt ttatagtgac agcgggccta tttgtatggt gtaaaccgga  900
gtgctaacaa tcttctacaa gaaacagcct gtacataaat ttacggcata tatataccgg  960
aacgtggctt ggccacgtat gttattaacg cgggctggca ggaacttact aggccgtgcc  1020
attccggtgt caaatccgac cgaatccggg gactcgtctc gcggaaatgt gtttcttttt  1080
agagacatgg attcttacaa accgagaccc tgtcatgccc gggatgaggg tctgccacta  1140
acaactttcc gaacatgatg ggaagaaccc cctaacgggc gcccacctgg aggaatttgg  1200
gccggggcac caccgcccga ggtggggcgg aaaaccccct ccaggggtcc catcctcaat  1260
ttttccgggg gggacccccc tccccccaa aatgagggaa aacccccggg ggggcacccc  1320
caaaagaagg agagcccccc accctcactc ttcccgcccg gcgtgcgggg gcgggttttt  1380
ttttctgtca aaataaattt tgtgttgttt gtgtgttcct cccccccccg ccgcgggggc  1440
ggggttgtac ttttttccct ctccatcccc cccccaccac aaaagaaaag gaggggacga  1500
cacccacagt gggtgtgttt tt                                          1522

SEQ ID NO: 4           moltype = DNA  length = 1554
FEATURE                Location/Qualifiers
source                 1..1554
                       mol_type = other DNA
                       organism = Synthetic construct
SEQUENCE: 4
ttgacggggg ggtctccagg cggaatgctt aatgcgttag ctgcagcact gaagggcgga  60
aaccccccaa cacttagcat tcatcgttta cggtatggac taccagggta tctaatcctg  120
tttgctaccc atactttcga gcctcagcgt cagttacaga ccagacagcc gccttcgcca  180
ctggtgttct tccatatatc tacgcatttc accgctacac atggagttcc actgtcctct  240
tctgcactca agtttcccag tttccgatgc acttcttcgg ttgagccgaa ggctttcaca  300
tcagacttaa aaaaccgcct gcgctcgctt tacgcccaat aaatccggac aacgcttgcc  360
acctacgtat taccgcggct gctggcacgt agttagccgt ggctttctgg ttaaataccg  420
tcaatacctg aacagttact ctcagatatg ttcttcttta acaacagagt tttacgagcc  480
gaaacccttc ttcactcacg cggcgttgct ccatcagact ttcgtccatt gtggaagatt  540
ccctactgct gcctcccgta ggagtttggg ccgtgtctca gtcccaatgt ggccgattac  600
cctctcaggt cggctacgta tcattgccat ggtgagccgt taccccacca tctagctaat  660
acgccgcggg accatccaaa agtgatagcc gaagccatct ttcaaactcg gaccatgcgg  720
tccaagttgt tatgcggtat tagcatctgt ttccaggtgt tatcccccgc ttctgggcag  780
gtttcccacg tgttactcac cagttcgcca ctcactcaaa tgtaaatcat gatgcaagca  840
ccaatcaata ccagagttcg ttcgacttgc atgtattagg cacgccgcca gcgttcgtcc  900
tgacagagag aaaaaaaaaa aaaaaaaagg gccgggggga tcgggggggg gggggggggg  960
ggtgaggggt tgaggggggg gggggggggg gggggggggg gggggggggg gggggggggg  1020
gggggggggg gggggggggg gggggggggg gggggggggg gggggggggg gggggggggg  1080
gggggggggg ggggtgtgtg gggggggggg ggttgttgtt tttgtttggg gggggggttg  1140
tttttttgtgt gtgttttgtt gtttgtttgg gggtgtgttt tgttgtgggg tggggtgttg  1200
gggggggttgg gggggggggtg ttgtttgggg ggggtggggg ggggggtttt tttgttgttg  1260
tgtggttgtg tgttgtgtgg tgggtggggg gggtggtgtg tgtgtggggg tggggggtgt  1320
ttggtggggg gggggttgtt gtgggggggt ggtgtttgtt ttttgttttt ttttgtgtgt  1380
gggggggggg ggtgggggggt ggtttgtggg gtgttgtttg tgtgtggttg gtggtggtgt  1440
gtgggggggt tggggggggg ggggttgtct tttttgttgg tgttgggtgt ttgttggtgt  1500
tggtgtgtgg tggggtggtg tggtgggtgg gtgcttgttg tgtgtgtggt gtgt        1554
```

LACTOBACILLUS PLANT ARUM STRAIN, POLYSACCHARIDES DERIVED FROM STRAIN, AND USE THEREOF

CROSS-REFERENCE TO RELATED APPLICATIONS

This is a Continuation under 35 USC § 120 and 35 USC § 365(c) of International Patent Application No. PCT/KR2021/000351 filed Jan. 11, 2021, and claims priority under 35 USC § 119 of Korean Patent Application No. 10-2020-0003493 filed Jan. 10, 2020. The disclosures of all such applications are hereby incorporated herein by reference in their respective entireties, for all purposes.

DEPOSITED MICROORGANISM

In conformity with the requirements of 37 CFR § 1.801-1.809, a deposit of the biological material (microorganism strain) identified herein as *Lactobacillus plantarum* IMB19 was made by the applicant hereof on Oct. 21, 2020 at Korean Collection for Type Cultures (KCTC), Korea Research Institute of Bioscience and Biotechnology (KRIBB), 181, Ipsin-gil, Jeongeup-si, Jeolllabuk-do 56212, Republic of Korea, for which a KCTC Deposit Receipt was issued on Oct. 21, 2020 (Accession Number: KCTC 14337BP), under and subject to the Budapest Treaty on the International Recognition of the Deposit of Microorganisms for the Purpose of Patent Procedure.

REFERENCE TO SEQUENCE LISTING

This application includes an electronically submitted sequence listing in .XML format. The .XML file contains a sequence listing entitled "621_SeqID.xml" created on Jul. 12, 2022 and is 7,664 bytes in size. The sequence listing contained in this .XML file is part of the specification and is hereby incorporated by reference herein in its entirety.

TECHNICAL FIELD

The present invention relates to a novel *Lactobacillus plantarum* IMB19 strain, a polysaccharide derived from the strain, and the use thereof, and more particularly to a *Lactobacillus plantarum* IMB19 strain having accession number KCTC 14337BP and having immunostimulatory activity and anti-tumor activity, a polysaccharide derived from the strain, and the use thereof for immune modulation, tumor inhibition, and treatment of an infectious disease.

BACKGROUND ART

Mammals host a community of microbes that constantly interact with the immune system. Symbiotic microorganisms enter into a symbiotic relationship with the host and interact with the host in a variety of processes, such as digestion, behavior, and maturation of the immune system (Cerf-Bensussan N., Gaboriau-Routhiau V. The immune system and the gut microbiota: friends or foes? Nat. Rev. Immunol. 2010; 10(10):735-44). Likewise, fungi exist in the human body and affect the immune system of the host (Wheeler M. L., Limon J. J., Underhill D. M. Immunity to Commensal Fungi: Detente and Disease. Annu. Rev. Pathol. 2017; 12:359-85). Innate immune cells detect various pathogen-associated molecular patterns (PAMPs) on the surface of fungal cells, including polysaccharides, through pattern recognition receptors (PRRs) such as toll-like receptors (TLRs). Upon detection of a signal, innate immune cells produce immune signaling molecules such as cytokines in order to alter gene expression profiles and control acquired immunity (Iliev I.D., Leonardi I. Nat. Rev. Immunol. 2017; 17(10):635-46, Underhill D. M., Iliev I.D., Nat. Rev. Immunol. 2014; 14(6):405-16, and Brubaker S. W., Bonham K. S., Zanoni I. et al. Annu. Rev. Immunol. 2015; 33:257-90).

The WHO defines probiotics as live microorganisms that, when administered in appropriate amounts, are beneficial to the health of the host (*Nat. Rev. Gastroenterol Hepatol* 11, 506-514 (2014)). Probiotics serve as a supplement to the host's gut microflora, and have been reported to be effective in improving intestinal barrier function and modulating the host's immune system (Microb. Ecol. Health Dis. 26, 25877 (2015)). Most probiotics belong to the phylum Firmicutes, which is the largest single bacterial phylum, and most thereof are gram-positive bacteria having low "G+C" content, and are mainly classified into the Bacilli and Clostridia groups. *Lactobacillus* species is lactic acid bacteria (LAB) belonging to the family Lactobacillaceae. *Lactobacillus* is a well-known microbial organism having a distinct ecological status. Several types of LAB are known to be traditionally associated with foods such as milk, dairy products, fermented foods, and sausages. Lactobacilli are a group of microorganisms recognized as GRAS (Generally Regarded As Safe) by the FDA, and are widely used in food and other industries. Lactobacilli are classified as conditioned anaerobic, nonsporulation, non-motile, rod-shaped, and gram-positive bacteria, and are generally considered catalase-negative. *Lactobacillus* may exhibit homofermentative or heterofermentative characteristics, and produces lactic acid as a final product of primary fermentation (Front Cell Infect Microbiol. 2, 86 (2012)). *Lactobacillus* forms smooth and convex colonies.

Molecular identification methods are needed in order to identify individual strains due to similar biochemical and morphological properties in LAB. Several types of lactic acid bacteria have been isolated and characterized from foods, particularly fermented foods. Fermentation generally refers to biochemical changes caused by microorganisms. Kimchi, a traditional Korean food, is mostly fermented cabbage, and has beneficial effects on nutrition and health (*Crit. Rev. Food Sci. Nutr.* 34, 175-203 (1994)). Kimchi is known to contain a unique microbial community. According to several reports, it is known that lactic acid bacteria are mainly present in kimchi, and *Weissella, Lactobacillus*, and *Leuconostoc* are the dominant species, and in particular, *Lactobacillus plantarum* is known as the most dominant strain (*Food Sci. Biotechnol.* 19, 641-646 (2010)). *Lactobacillus plantarum* is one of the most studied strains due to strain-specific probiotic profiles and technical application in the food industry. Most kimchi microbes may be cultured (*Int. J. Food Microbiol.* 102, 143-150 (2005)), and isolation of individual microorganisms is essential to study the benefits thereof on health.

Meanwhile, cancer growth and proliferation are strictly regulated by the host immune response. For the growth and proliferation of tumor cells, it must be possible to evade surveillance by the immune system, which induces early death of tumor cells. Tumor cells grow and proliferate by evading the immune system by forming an immunosuppressive tumor microenvironment through various pathways such as cytokine secretion, molecular expression on the cell surface, and the like. As a cancer treatment strategy targeting this immune evasion mechanism, various efforts have been made to induce or strengthen the immune system. Tumor immunotherapy is said to be a therapeutic method for restoring or enhancing the ability of the immune system to recognize or destroy tumors in order to overcome the mechanism of immune suppression or evasion acquired by the tumor. In 2011, an ipilimumab immunotherapeutic drug was used to successfully treat patients with malignant melanoma. Since then, various immunotherapeutic agents such as nivolumab and pembrolizumab have been continuously developed.

As a tool for such tumor immunotherapy, there are an increasing number of reports and cases pertaining to the importance of gut microbiota and application thereof. Gut microbiota play an essential role in forming the host's local and systemic immune responses (*Science* 330, 1768-1773 (2010), *Cell* 148, 1258-1270 (2012)). The diversity and composition of gut microbiota have also been shown to affect responsiveness to chemotherapy (Cancer Immunol. Immunother. 55, 1470-1479 (2006); *Science* 342, 971-976 (2013)). In particular, certain symbiotic microorganisms have been found to be associated with activation of spontaneous anti-tumor immunity, and have been found to exhibit synergistic effects on the therapeutic efficacy of immunotherapeutic agents in experiments (*Science* 350, 1084-1089 (2015), *Science* 350, 1079-1084 (2015)) and human cancer (*Science* 359, 91-97 (2018), *Nature* 453, 620-625 (2008)). Thus, it is becoming clear that certain strains, such as gut microbiota, may also influence the progression of extramucosal and distant tumors. Based on these various reports, alteration of gut microbiota is regarded as an effective and viable clinical treatment option. Most recent studies have demonstrated the comprehensive effect of a specific strain or a community of strains on the host's immune system or anti-tumor immunity from the point of view of probiotics, but little information is known about mechanisms such as active ingredients derived from specific strains showing these effects and signaling pathways thereof.

In particular, as a consideration for the use of such microorganisms or metabolites thereof to treat patients, some patients have to suppress an overactive immune response (i.e. allergy or autoimmune disease), while some patients have to strengthen the immune system (i.e. cancer or viral infection). For example, when *Bifidobacterium*, which is a Th17-induced probiotic, was administered to an animal model of rheumatoid arthritis, arthritis symptoms were exacerbated (Tze Guan Tan, 113(50):E8141-E8150, 2016). Therefore, it is of great therapeutic importance to identify beneficial microorganisms and elucidate the mechanism of action factors thereof.

Against this technical background, the present inventors made great efforts to elucidate a clear correlation and mechanism between components, structures, molecular weights, etc. of microorganism-derived polysaccharides and immunomodulatory activity thereof, identified a novel *Lactobacillus plantarum* strain having remarkably high immune-enhancing activity from kimchi, a traditional Korean food, and deposited the same with accession number KCTC 14337BP at the Korea Biological Resource Center. Moreover, it has been confirmed that, when a host was fed with the novel strain, *Lactobacillus plantarum* KCTC 14337BP, the number of effector T cells was significantly increased and Treg production was inhibited, thereby stimulating the immune system in the host and inhibiting tumor growth and proliferation.

Furthermore, the present inventors not only identified and characterized the novel strain, but also ascertained that the capsular polysaccharide of the novel strain and a fraction having a specific structure (CPS-100) thereof are effective molecules exhibiting immune stimulation and enhancement effects, and also that, by stimulating anti-tumor immune responses through various mechanisms, such as activation of CD8+ T-cell function, increased macrophage infiltration in tumors by CPS, and differentiation/reprogramming of macrophages to an inflammatory phenotype, it is possible to greatly inhibit tumor growth, thus culminating in the present invention.

The information described in the background section is only for improving understanding of the background of the present invention, and it is not to be construed as including information forming the related art already known to those skilled in the art to which the present invention belongs.

DISCLOSURE

It is an object of the present invention to provide a novel strain having immunostimulatory activity.

It is another object of the present invention to provide a polysaccharide derived from the strain having immunostimulatory activity.

It is still another object of the present invention to provide the use of the strain and the polysaccharide derived from the strain for immune modulation and/or prevention, amelioration, or treatment of a tumor or an infectious disease.

In order to accomplish the above objects, the present invention provides a *Lactobacillus plantarum* IMB19 strain having accession number KCTC 14337BP.

In addition, the present invention provides a capsular polysaccharide derived from the strain having immune-enhancing activity.

In addition, the present invention provides a method of producing a capsular polysaccharide having immune-enhancing activity including culturing the strain and obtaining a capsular polysaccharide from the cultured strain.

In addition, the present invention provides a polysaccharide represented by Formula I below:

$$-[\text{-D-B-I-F-G-C-E-H-A-}]_n- \quad \text{[Formula I]}$$

in Formula I,

A and D are galactose,

B, C, E, G, and H are rhamnose,

F is N-acetylglucosamine,

I is glucose, and n is an integer from 1 to 10.

In addition, the present invention provides a composition for immune modulation containing the strain and/or the polysaccharide as an active ingredient.

In addition, the present invention provides a pharmaceutical composition for preventing or treating a tumor or an infectious disease containing the strain and/or the polysaccharide as an active ingredient.

In addition, the present invention provides a food composition for immune enhancement containing the strain and/or the polysaccharide as an active ingredient.

In addition, the present invention provides a method of preventing, ameliorating, or treating a tumor or an infectious disease including administering the strain and/or the polysaccharide to a subject.

In addition, the present invention provides the use of the strain and/or the polysaccharide for immune modulation and/or prevention, amelioration, or treatment of a tumor or an infectious disease.

In addition, the present invention provides the use of the strain and/or the polysaccharide for the manufacture of a composition for immune modulation.

In addition, the present invention provides the use of the strain and/or the polysaccharide for the manufacture of a pharmaceutical composition for the prevention or treatment of a tumor or an infectious disease.

In addition, the present invention provides the use of the strain and/or the polysaccharide for the manufacture of a food composition for immune enhancement.

In addition, the present invention provides a method of producing inflammatory T cells including priming antigen-presenting cells with the *L. plantarum* IMB19 strain and/or the polysaccharide of Formula I and co-culturing the primed antigen-presenting cells with T cells.

In addition, the present invention provides a method of producing M1-phenotype macrophages including differentiating macrophages into M1-phenotype macrophages by treating macrophages with the *L. plantarum* IMB19 strain and/or the polysaccharide of Formula I and obtaining the differentiated M1-phenotype macrophages.

In addition, the present invention provides a cell therapeutic agent for preventing or treating a tumor or an infectious disease containing, as an active ingredient, the inflammatory T cells produced through the above method and/or the M1-phenotype macrophages produced through the above method.

Figure 26:
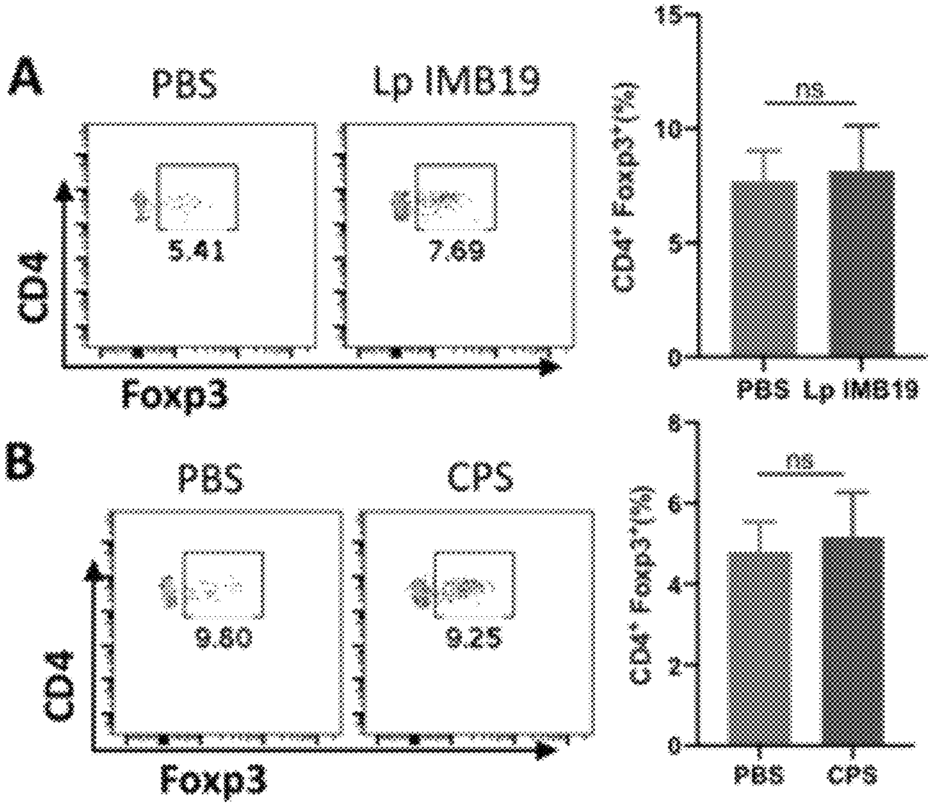
Figure 27:
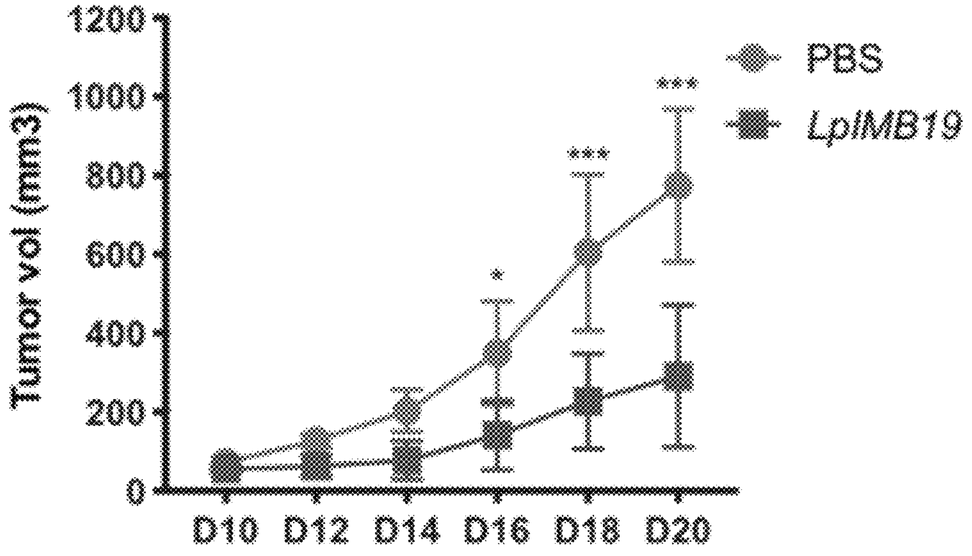
Figure 28:
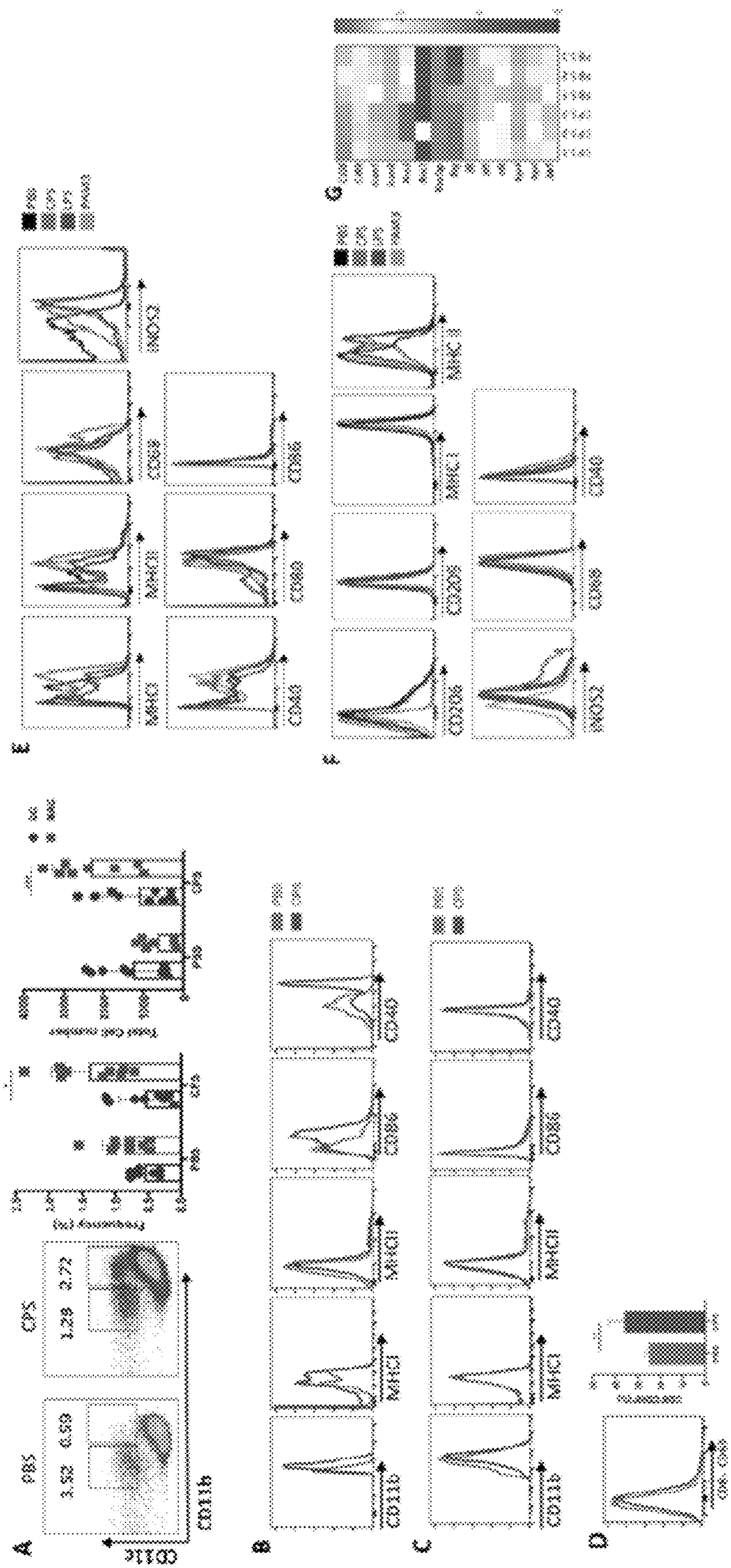

SPF mice treated or not treated with *L. plantarum* IMB 19 or CPS, with B showing images of tumors isolated from mice, with C and D showing the proportions of tumor-infiltrating CD8+ and CD4+ T cells as determined through flow cytometry 16 to 18 days after the start of treatment with *L. plantarum* IMB 19 (C) or CPS (D), in which data are mean±SEM values, and data were analyzed through two-way ANOVA using Dunnett's multiple comparisons (A) or non-parametric two-tailed t-test (C-D), *p<0.05, p<0.01, *p<0.001, with E and F showing the percentage of tumor-infiltrating IFNγ+ CD8+ T cells and mean fluorescence intensity (MFI) of tumor-infiltrating CD8+ T cells when treated or not treated with *L. plantarum* IMB 19 (E) or CPS (F), and with G and H showing the frequency of IFNγ+ CD4+ T cells when treated or not treated with *L. plantarum* IMB 19 (G) or CPS (H), in which data are mean±SEM values, and data were analyzed through a non-parametric two-tailed t-test, *P<0.05, ns: not significant;

FIG. 26 shows that *L. plantarum* IMB19 and CPS do not alter regulatory T cell populations in tumors, in which A and B show the percentage of tumor-infiltrating CD4+ Foxp3+ regulatory T cells in tumor-infiltrating lymphocytes upon treatment with *L. plantarum* IMB 19 (A) or CPS (B), in which data were analyzed through a non-parametric two-tailed t-test, *P<0.05, ns: not significant;

FIG. 27 shows the tumor growth inhibitory activity of *L. plantarum* IMB19 in EMT breast cancer, showing the growth kinetics of EMT-6 breast cancer in Balb/c SPF mice treated or not treated with *L. plantarum* IMB19, in which data are mean±SEM and were analyzed through two-way ANOVA with Dunnett's multiple comparisons, *P<0.05, *P<0.001; and FIG. 28** shows the activity of CPS on improving intratumoral infiltration of inflammatory macrophages in B16.F10 melanoma, in which A shows the number and percentage of CD45+ CD11c+ CD11b+ tumor-infiltrating macrophages upon CPS treatment 40 hours after tumor inoculation, B and C show the activity markers, namely CD11b, MHC I, MHC II, CD86, and CD40, on tumor-infiltrating macrophages (B) and dendritic cells (C) upon CPS treatment, D shows the percentage of CD8+ CD69+ T cells in tumor-draining lymph nodes upon CPS treatment, in which data are mean±SEM and were analyzed through two-way ANOVA with Dunnett's multiple comparisons (A) or non-parametric two-tailed t-test (B) *P<0.05, P<0.01, *P<0.001, E and F show the activity markers, namely MHC I, MHC II, iNOS2, CD68, CD40, CD80, and CD86, on CPS (10 μg/ml)-treated mouse peritoneal macrophages in vitro immediately after isolation (E) or after 24 hours of IL-4 treatment (F), and G shows the results of DAVID pathway analysis of the M1 macrophage gene signature enriched in CPS- or PBS-treated tumor-derived macrophages isolated 40 hours after tumor inoculation.

MODE FOR INVENTION

Unless otherwise defined, all technical and scientific terms used herein have the same meanings as those typically understood by those skilled in the art to which the present invention belongs. In general, the nomenclature used herein is well known in the art and is typical.

As symbiotic microorganisms are known to be deeply involved in the immunomodulatory response of a host such as a human, thorough research on symbiotic microorganisms having the ability to enhance or suppress immunity, namely probiotics, is ongoing. Among the numerous microorganism species coexisting evolutionarily with humans, only a very small number of microorganism species have been found to have immunomodulatory activity, and even within a given species of microorganism, immunomodulatory activity varies significantly depending on the type of strain, or even has the opposite effect. Since the activity possessed by microorganisms is very diverse and different for each microorganism, interest in postbiotics such as useful metabolites or effective molecules produced by microorganisms having immunomodulatory activity has recently surged. In particular, mannose, beta-glucan, and polysaccharides derived from microorganisms are known to have various effects on the immune system of the host. However, it has been reported that microorganism-derived polysaccharides also have various activities depending on the types and structures thereof, and that polysaccharides such as zymosan simultaneously exhibit aspects of both immune enhancement and immune suppression. Therefore, it is very important to elucidate the immunomodulatory mechanism of each polysaccharide in order to use probiotic-derived polysaccharides for immune modulation of subjects, particularly for clinical treatment of humans. However, there have been few reports on the relationship between polysaccharide structure and immunomodulatory activity.

The present inventors have earnestly endeavored to elucidate the relationship between polysaccharide structure and immunomodulatory activity from the point of view of postbiotics, and have revealed the relationship and mechanism of the immunomodulatory activity and the structure of polysaccharides derived from various strains such as *Bifidobacterium* and yeast showing immunomodulatory activity and filed a patent application thereof (Korean Patent Application No. 2018-0067535 (to be registered), No. 2019-0091908, etc.).

In an embodiment of the present invention, the present inventors identified a novel *Lactobacillus plantarum* IMB19 strain exhibiting high immunostimulatory activity from kimchi, a traditional fermented food of Korea, and deposited the same with the Korea Biological Resource Center (Accession number: KCTC 14337BP).

In another embodiment of the present invention, it has been confirmed that, in a co-culture system designed to include both the innate immune system and the adaptive immune system, the strain increased immunostimulatory cytokines (e.g. IFN-γ), inhibited anti-inflammatory cytokines (e.g. IL-10), significantly increased effector T cells, and inhibited Treg production, thereby stimulating the immune system in the host and inhibiting tumor growth and proliferation.

Accordingly, an aspect of the present invention pertains to a *Lactobacillus plantarum* IMB19 strain having accession number KCTC 14337BP (*Lactobacillus plantarum* IMB19).

The *Lactobacillus plantarum* IMB19 strain of the present invention may exhibit excellent immune-enhancing activity and anti-tumor activity. More specifically, the strain of the present invention may exhibit various immune-enhancing and/or anti-tumor activities, such as i) induction of T-cell differentiation to an inflammatory phenotype such as induction of helper T cells and inhibition of Treg cell differentiation, ii) stimulation of CD8+ T cells, enhancement of activity, and improvement of intratumoral infiltration, iii) inhibition of Treg cell activity, iv) increased macrophage infiltration in tumors, and v) activation of macrophages to inflammatory cells and reprogramming from M2 to M1 macrophages.

The *Lactobacillus plantarum* IMB19 strain of the present invention (hereinafter abbreviated as *L. plantarum* IMB19) was isolated from kimchi, identified as a novel strain through 16S rRNA analysis, recA amplification/band comparison, whole-gene sequencing, and phylogenetic, morphological, and physiological analysis, and deposited.

In the present invention, the *L. plantarum* IMB19 strain may be derived from a fermented food, for example, kimchi.

In the present invention, the *L. plantarum* IMB19 strain may form small, smooth, and circular translucent colonies.

In the present invention, the *L. plantarum* IMB19 strain may be non-flagellated.

In the present invention, the *L. plantarum* IMB19 strain may form rod-shaped colonies.

In the present invention, the *L. plantarum* IMB19 strain may have a capsular layer.

In the present invention, the *L. plantarum* IMB19 strain may be non-hemolytic or γ-hemolytic.

In the present invention, the *L. plantarum* IMB19 strain may be negative for gelatinase activity.

In the present invention, the *L. plantarum* IMB19 strain may not produce biogenic amines such as histamine, cadaverine, tyramine, and/or putrescine.

In the present invention, the *L. plantarum* IMB19 strain may have resistance to kanamycin.

In the present invention, the *L. plantarum* IMB19 strain may have immune-enhancing activity and/or anti-tumor activity. More specifically, the *L. plantarum* IMB19 strain may exhibit various immune-enhancing and/or anti-tumor activities, such as i) induction of T-cell differentiation to an inflammatory phenotype such as induction of helper T cells and inhibition of Treg cell differentiation, ii) stimulation of CD8+ T cells, enhancement of activity, and improvement of intratumoral infiltration, iii) inhibition of Treg cell activity, iv) increased macrophage infiltration in tumors, and v) activation of macrophages to inflammatory cells and reprogramming from M2 to M1 macrophages, but the present invention is not limited thereto.

In the present invention, the *L. plantarum* IMB19 strain is capable of inhibiting tumor growth.

In an embodiment of the present invention, it has been confirmed that, in an animal tumor model fed with the strain, a remarkable immune-enhancing effect and anti-tumor activity were exhibited through various mechanisms such as stimulation of CD8+ T cells, differentiation in macrophages, phenotype induction, inhibition of Treg, improvement of intratumoral infiltration of immune cells, and the like.

In another embodiment of the present invention, it has been confirmed that tumor growth was significantly inhibited upon treatment with CPS.

Accordingly, another aspect of the present invention pertains to a composition for immune modulation containing the strain and/or a culture solution thereof as an active ingredient.

In addition, another aspect of the present invention pertains to an immunomodulation method including administering the strain and/or the culture solution thereof to a subject.

In addition, another aspect of the present invention pertains to the use of the strain and/or the culture solution thereof for immune modulation.

In addition, another aspect of the present invention pertains to the use of the strain and/or the culture solution thereof for the manufacture of a composition for immune modulation.

As used herein, the term "immune modulation" refers to overcoming an immune imbalance in the blood and maintaining immune homeostasis. Maintenance of immune homeostasis refers to a state in which immune tolerance, which suppresses immunity, and immune response, which enhances immunity, are balanced. Maintaining such a state is essential for the treatment of most diseases, including tumors and cancer. In the present invention, the composition is preferably used for immune stimulation.

In the present invention, the composition for immune modulation may be used for immune stimulation.

In the present invention, the composition for immune modulation may be a composition for immune stimulation or immune enhancement.

In the present invention, the composition for immune modulation may be a probiotic composition.

As used herein, the term "probiotic" means a live microorganism that is beneficial to the health of a host when administered in an appropriate amount (*Nat. Rev. Gastroenterol Hepatol* 11, 506-514 (2014)). Probiotics serve as a supplement to the host's gut microflora, and may be characterized by improving intestinal barrier function and modulating the host's immune system.

In the present invention, the probiotic composition may further include prebiotics.

In the present invention, the composition for immune modulation may be used as a pharmaceutical composition or a food composition for the purpose of preventing, ameliorating, or treating tumors, infectious diseases, and immune diseases caused by or symptomatic of immune reduction/suppression. Here, the amount and form of use may be appropriately adjusted depending on the purpose.

In the present invention, the composition for immune modulation may be used in combination with other pharmaceutical compositions or food compositions, or may be used as an adjuvant. Examples of the other pharmaceutical compositions include, but are not limited to, immunotherapy-related immunotherapeutic agents, immune-cell therapeutic agents, and the like. Examples of the other food compositions may include, but are not limited to, fermented foods, fermentation starters for producing fermented food, functional health foods such as nutritional supplements, and the like.

In the present invention, the composition for immune modulation may further include other probiotic strains, compounds, adjuvants, additives, carriers, excipients, etc., in addition to the *L. plantarum* IMB19 strain of the present invention and/or the culture solution thereof.

As used herein, the term "culture solution thereof" may be a culture stock solution containing the *L. plantarum* IMB19 strain of the present invention, and may be used in a comprehensive sense including all of its lysate, centrifugation supernatant or pellet, concentrate, dried product, and the like. The *L. plantarum* IMB19 strain of the present invention may be cultured through a typical method of culturing a *Lactobacillus* strain. The method of culturing the strain of the present invention has been exemplarily described in Examples. The medium may include a natural medium or a synthetic medium. Examples of the carbon source of the medium may include glucose, sucrose, dextrin, glycerol, etc., and examples of the nitrogen source may include peptone, meat extract, yeast, soybean, ammonium salt, nitrate, and other organic or inorganic nitrogen-containing compounds, but the present invention is not limited thereto. The inorganic salt included in the medium may include, but is not limited to, magnesium, manganese, calcium, iron, potassium, etc. In addition to the components of the carbon source, nitrogen source, and inorganic salt, amino acids, vitamins, nucleic acids, and the like may be added.

In the present invention, the culture solution may contain an *L. plantarum* IMB19 strain and/or an active ingredient (e.g. polysaccharide) having immunomodulatory activity derived from the *L. plantarum* IMB19 strain. The strain may be in a liquid state or a dry state, and the drying method may include, for example, natural drying, spray drying, and freeze drying, but is not limited thereto.

Still another aspect of the present invention pertains to a pharmaceutical composition for preventing or treating a tumor or an infectious disease containing the *L. plantarum* IMB19 strain of the present invention or a culture solution thereof as an active ingredient.

In addition, still another aspect of the present invention pertains to a method of preventing or treating a tumor or an infectious disease including administering the strain and/or the culture solution thereof to a subject.

In addition, still another aspect of the present invention pertains to the use of the strain and/or the culture solution thereof for the prevention, amelioration, or treatment of a tumor or an infectious disease.

The present invention also pertains to the use of the strain and/or the culture solution thereof for the manufacture of a pharmaceutical composition for the prevention or treatment of a tumor or an infectious disease.

As used herein, the term "tumor" refers to a phenomenon by which cells become autonomous and excessively proliferate by deviating from the body's regulatory mechanisms, or neoplasms or hyperplasia generated thereby. The tumor includes, for example, all of benign, premalignant, and malignant tumors, and more specific examples thereof include histiocytoma, glioma, astrocytoma, osteoma, various types of cancer, for example, lung cancer, small-cell lung cancer, gastric cancer, gastrointestinal cancer, bowel cancer, colon cancer, rectal cancer, pancreatic cancer, breast cancer, skin cancer, ovarian cancer, prostate cancer, testicular cancer, liver cancer, kidney cancer, bladder cancer, pancreatic cancer, brain cancer, sarcoma, osteosarcoma, melanoma, lymphoma (Hodgkin's lymphoma, FL, MCL, MZBL, CLL, T-ALL, AML, ALL, etc.), blood cancer, leukemia, psoriasis, bone disease, fibroproliferative disorder, atherosclerosis, etc., and preferably melanoma, breast cancer, kidney cancer, lung cancer, bladder cancer, and rectal cancer, but the present invention is not limited thereto.

As used herein, the term "infectious disease" refers to a pathogen-associated disease induced or exacerbated by infection with various pathogens. For example, the infectious disease may be a disease induced or aggravated by infection with a virus, bacterium, fungus, protozoan, parasite, prion, or protein aggregate, but the present invention is not limited thereto.

As used herein, the term "prevention" refers to any action of inhibiting a disease or delaying the onset of a disease by administration of the pharmaceutical composition according to the present invention.

As used herein, the term "treatment" refers to any action by which symptoms of a disease are ameliorated or beneficially changed by administration of the pharmaceutical composition according to the present invention.

The pharmaceutical composition of the present invention exhibits preventive or therapeutic and anti-inflammatory effects on various diseases through the aforementioned immune-enhancing effect and/or anti-tumor effect of the active ingredient thereof.

The pharmaceutical composition may further include suitable carriers, excipients, and diluents commonly used in pharmaceutical compositions, in addition to containing the *L. plantarum* IMB19 strain of the present invention or the culture solution thereof.

The carriers, excipients and diluents that may be included in the composition include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. When formulating the composition, it is usually prepared using a diluent or excipient such as a filler, an extender, a binder, a wetting agent, a disintegrant, a surfactant, etc.

The pharmaceutical composition according to the present invention may be formulated and used in various forms according to a typical method. Suitable formulations include tablets, pills, powders, granules, sugar-coated tablets, hard or soft capsules, solutions, suspensions, emulsions, injections, oral formulations such as aerosols, external preparations, suppositories, and sterile injection solutions, but the present invention is not limited thereto.

The pharmaceutical composition according to the present invention may be formulated in a suitable dosage form using a pharmaceutically inert organic or inorganic carrier. Specifically, when the formulation is a tablet, coated tablet, sugar-coated tablet, or hard capsule, it may include lactose, sucrose, starch or derivatives thereof, talc, calcium carbonate, gelatin, stearic acid, or salts thereof. Also, when the formulation is a soft capsule, it may include vegetable oils, waxes, fats, and semi-solid and liquid polyols. Also, when the formulation is in the form of a solution or syrup, it may include water, polyol, glycerol, and vegetable oil.

The pharmaceutical composition according to the present invention may further include a preservative, a stabilizer, a wetting agent, an emulsifier, a solubilizing agent, a sweetener, a colorant, an osmotic pressure adjuster, an antioxidant, and the like, in addition to the carrier described above.

The pharmaceutical composition according to the present invention is administered in a pharmaceutically effective amount. In the present invention, "pharmaceutically effective amount" means an amount sufficient to treat a disease at a reasonable benefit/risk ratio applicable to medical treatment, and the effective dose level is determined depending on various factors including the type of patient's disease, severity of disease, drug activity, sensitivity to drugs, administration time, administration route, excretion rate, treatment period, and drugs used simultaneously therewith, and other factors well-known in the medical field. The pharmaceutical composition according to the present invention may be administered as an individual therapeutic agent or in combination with other therapeutic agents, may be administered sequentially or simultaneously with conventional therapeutic agents, and may be administered one or multiple times. In consideration of all of the above factors, it is important to administer the composition in the minimum amount capable of obtaining the maximum effect without side effects, which may be easily determined by those skilled in the art.

The pharmaceutical composition of the present invention may be administered to a subject through any of various routes. The mode of administration may be, for example, subcutaneous, intravenous, intramuscular, intrauterine dural, or intracerebrovascular injection. The pharmaceutical composition of the present invention is determined depending on the type of drug as an active ingredient, in consideration of various factors such as the disease to be treated, the route of administration, the patient's age, gender, and body weight, and the severity of disease.

The mode of administration of the pharmaceutical composition according to the present invention may be easily selected depending on the dosage form, and oral or parenteral administration is possible. The dosage thereof may vary depending on the patient's age, gender, and body weight, the severity of disease, and the route of administration.

The composition of the present invention may be administered in combination with other therapeutic regimens or therapeutic agents. When used for the prevention or treatment of tumors, the other therapy or therapeutic agent is preferably an immunotherapy or immune-cell therapeutic agent, but is not limited thereto, and may be used in various combinations according to the judgment of a clinician.

Yet another aspect of the present invention pertains to a food composition for immune enhancement containing the *L. plantarum* IMB19 strain of the present invention or a culture solution thereof as an active ingredient.

In addition, yet another aspect of the present invention pertains to the use of the strain and/or the culture solution thereof for the manufacture of a food composition for immune enhancement.

The food composition of the present invention is capable of maintaining immune function homeostasis by enhancing or improving immune activity.

The food composition of the present invention may be a functional health food exhibiting an effect of preventing or ameliorating a tumor or an infectious disease.

As used herein, the term "food" refers to meat, sausages, bread, chocolate, candy, snacks, confectioneries, pizza, ramen, other noodles, gum, dairy products including ice cream, various soups, beverages, tea, drinks, alcoholic beverages, vitamin complexes, prebiotics, probiotics, postbiotics, functional health foods, and health foods, and includes all foods in a typical sense.

The term "functional health food" has the same meaning as the term "food for special health use (FoSHU)", and refers to a food having high pharmaceutical and medical effects processed in order to efficiently show bioregulatory functions, in addition to nutritional supply. Here, "functional" means obtaining useful effects for health purposes, such as nutrient regulation or physiological activity with regard to the structure and function of the human body. The food of the present invention may be manufactured using a method commonly used in the art, and at the time of manufacture, raw materials and components commonly used in the art may be added. Moreover, any food form may be provided without limitation, so long as it is a formulation recognized as a food, and the functional health food according to the present invention may take the form of a powder, granule, tablet, capsule, or beverage.

Health food is a food having an active effect on health maintenance or promotion beyond that of a general food, and health supplement food is a food for health supplement purposes. In some cases, the terms "functional health food", "health food", and "health supplement food" are used interchangeably.

The food composition may further include a physiologically acceptable carrier, the type of which is not particularly limited, and any carrier commonly used in the art may be used.

Moreover, the composition may include additional ingredients that are commonly used in food compositions to improve smell, taste, visual appearance, and the like. For example, it may include vitamins A, C, D, E, B1, B2, B6, B12, niacin, biotin, folate, pantothenic acid, and the like. Also, it may include minerals such as zinc (Zn), iron (Fe), calcium (Ca), chromium (Cr), magnesium (Mg), manganese (Mn), copper (Cu), chromium (Cr), and the like. Also, it may include amino acids such as lysine, tryptophan, cysteine, valine, and the like.

Also, the composition may include food additives, such as preservatives (potassium sorbate, sodium benzoate, salicylic acid, sodium dehydroacetate, etc.), disinfectants (bleaching powder, high bleaching powder, sodium hypochlorite, etc.), antioxidants (butylhydroxyanisole (BHA), butylhydroxy toluene (BHT), etc.), colorants (tar pigment, etc.), color development agents (sodium nitrite, sodium nitrite, etc.), bleaches (sodium sulfite), seasonings (MSG, etc.), sweeteners (dulcin, cyclamate, saccharin, sodium, etc.), flavorings (vanillin, lactones, etc.), expansion agents (alum, D-potassium hydrogen tartrate, etc.), strengthening agents, emulsifiers, thickening agents (thickeners), film-forming agents, gum base agents, foam inhibitors, solvents, improving agents, and the like. These additives may be selected depending on the type of food, and may be used in appropriate amounts.

The food composition may further include a food supplement additive that is acceptable for human consumption, in addition to the *L. plantarum* IMB19 strain of the present invention or the culture solution thereof, and may be used along with other foods or food ingredients, and may be used appropriately according to a typical method. The amount of the active ingredient that is included therein may be appropriately determined according to the purpose of use thereof (prevention, health, or therapeutic treatment).

In an embodiment of the present invention, it has been confirmed that the capsular polysaccharide is an active ingredient showing the immune-enhancing activity of *L. plantarum* IMB19 of the present invention.

In another embodiment of the present invention, it has been confirmed that the isolated capsular polysaccharide exhibits excellent immune-enhancing activity and anti-tumor activity through various mechanisms such as i) induction of T-cell differentiation to an inflammatory phenotype such as induction of helper T cells and inhibition of Treg cell differentiation, ii) stimulation of CD8+ T cells, enhancement of activity, and improvement of intratumoral infiltration, iii) inhibition of Treg cell activity, iv) increased macrophage infiltration in tumors, and v) activation of macrophages to inflammatory cells and reprogramming from M2 to M1 macrophages, as in the *L. plantarum* IMB19 strain.

In still another embodiment of the present invention, the capsular polysaccharide was structurally analyzed through NMR.

Accordingly, still yet another aspect of the present invention pertains to a capsular polysaccharide (CPS) derived from the *L. plantarum* IMB19 strain having immune-enhancing activity.

In the present invention, the capsular polysaccharide may include a polysaccharide of Formula I below.

$$-[\text{-D-B-I-F-G-C-E-H-A-}]_n- \quad \text{[Formula I]}$$

Here, A and D are galactose,

B, C, E, G, and H are rhamnose,

F is N-acetylglucosamine,

I is glucose, and n is an integer of 1 or more.

In the present invention, the polysaccharide of Formula I is a polymer structure of a repeating unit represented by [-D-B-I-F-G-C-E-H-A-] in Formula I.

In the present invention, when n in Formula I is 2 or more, the repeating units may be connected without limitation in various ways, in addition to direct covalent bonding. For example, the repeating units may be connected through chemical bonding, such as a glycosidic linkage or a phosphodiester linkage, or may be connected via a linker.

In the present invention, when n in Formula I is 2 or more, the repeating units ([-D-B-I-F-G-C-E-H-A-]) may be connected through a glycosidic linkage (—O—) between A and D.

In the present invention, when n in Formula I is 2 or more, the repeating units ([-D-B-I-F-G-C-E-H-A-]) may be connected through a phosphodiester linkage between A and D.

In the present invention, when n in Formula I is 2 or more, carbon at position 1 in A of a repeating unit and carbon at position 6 in D of another repeating unit may be connected through a phosphodiester linkage.

In the present invention, at least one of A and D of Formula I may be phosphorylated, and preferably, in the case of A, the hydroxyl group of carbon at position 1 is phosphorylated, and in the case of D, the hydroxyl group of carbon at position 6 is phosphorylated.

In the present invention, the galactose that is used includes galactose or derivatives thereof, which are generally present in nature. For example, in the present invention, the galactose may be provided in the form of an isomer in an α configuration or β configuration, or a D configuration or L configuration, preferably α-galactose, and more preferably α-D-galactose, but is not limited thereto.

In the present invention, the rhamnose that is used includes all of rhamnose or derivatives thereof, which are generally present in nature. For example, in the present invention, the rhamnose may be provided in the form of an isomer in an α configuration or β configuration, or a D configuration or L configuration, preferably α-rhamnose, and more preferably α-L-rhamnose, but is not limited thereto.

In the present invention, the N-acetylglucosamine that is used includes all of N-acetylglucosamine and derivatives thereof.

In the present invention, the glucose that is used includes all of typical glucose or derivatives thereof. For example, in the present invention, the glucose may be provided in the form of an isomer in an α configuration or β configuration, or a D configuration or L configuration, preferably glucose having a β configuration, and more preferably D-glucose, but is not limited thereto.

In the present invention, D and B (D-B) and B and I (B-I) may be connected through an α-1,3-glycosidic linkage.

In the present invention, I and F (I-F) may be connected through a β-1,6-glycosidic linkage.

In the present invention, F and G (F-G), G and C (G-C), C and E (C-E), and E and H (E-H) may be connected through an α-1,2-glycosidic linkage.

In the present invention, H and A (H-A) may be connected through an α-1,6-glycosidic linkage.

In the present specification, the glycosidic linkage is represented as α or β depending on the linkage orientation, and the numbers adjacent thereto refer to respective carbon numbers connected through a glycosidic linkage (—O—) in two monosaccharides. For example, "I and F (I-F) are connected through a β-1,6-glycosidic linkage" means that carbon at position 1 of I and carbon at position 6 of F are connected through a glycosidic linkage in β configuration with respect to I.

In the present invention, the capsular polysaccharide may include a polysaccharide of Formula I in which n is an integer of 1 or more, and may include a plurality of polysaccharides of Formula I polymerized with various n values. Preferably, the polysaccharide of Formula I is characterized in that n is a value ranging from 1 to 10.

In an embodiment of the present invention, it has been confirmed that the average degree of polymerization of the polysaccharide of Formula I included in the capsular polysaccharide was about 4, and also that the average molecular weight thereof was about 6.0 kDa. Each repeating unit ([-D-B-I-F-G-C-E-H-A-]) was confirmed to have a molecular weight (MW) of about 1.5 kDa.

In the present invention, the 'average degree of polymerization (average of n)' of the polysaccharide of Formula I included in the capsular polysaccharide is preferably 1 to 10, and most preferably about 4.

In the present invention, the average molecular weight of the polysaccharide of Formula I included in the capsular polysaccharide may be 1.5 to 15 kDa, and preferably about 6.0 kDa.

In an embodiment of the present invention, for the polysaccharide of Formula I included in the capsular polysaccharide, the capsular polysaccharide (CPS) derived from the *L. plantarum* IMB19 strain was separated through ion exchange chromatography using about 100 mM of NaCl as an eluent. The separation method is described in detail in Examples, but the present invention is not limited thereto. The polysaccharide may be obtained through a variety of conventionally known purification methods based on the structure and characteristics of the polysaccharide of Formula I described in the present invention.

In the present invention, the capsular polysaccharide may further include teichoic acid.

As confirmed in an embodiment of the present invention, in the present invention, the capsular polysaccharide may further include two or more teichoic acids.

In the present invention, the teichoic acid may be of a Gro-type or Rbo-type, and when the capsular polysaccharide additionally includes two or more teichoic acids, the teichoic acids may be included in the form of a single type or a mixture of two types.

In the present invention, the capsular polysaccharide may further include other polysaccharides or biomolecules such as lipids, in addition to the polysaccharide of Formula I and/or teichoic acid.

Even still another aspect of the present invention pertains to a method of producing a polysaccharide having immune-enhancing activity, including:

(a) culturing the strain described above; and (b) obtaining a capsular polysaccharide from the cultured strain.

In the present invention, the method may further include (c) obtaining an effective polysaccharide fraction having immune-enhancing activity by subjecting the obtained capsular polysaccharide to ion exchange chromatography.

The method of producing the capsular polysaccharide of the present invention and the step of obtaining the effective polysaccharide fraction having immune-enhancing activity are exemplarily described in detail in Examples of the present invention, but are not limited thereto.

In an embodiment of the present invention, the capsular polysaccharide (CPS) derived from the *L. plantarum* IMB19 strain was fractionated through ion exchange chromatography using a NaCl eluent at various concentrations, and the structure of the polysaccharide contained in each fraction was analyzed through NMR.

In another embodiment of the present invention, significant levels of IFN-γ, TNF-α, IL-6, and IL-12, and negligible levels of IL-10, IL-17, and IL1-β were produced only in CPS-100 purified using 100 mM NaCl among various fractions of the capsular polysaccharide (CPS) derived from the *L. plantarum* IMB19 strain, whereas no significant cytokine production was detected in other fractions (CPS-400 (including teichoic acid), etc.), indicating that the effective molecule exhibiting the immune-enhancing activity of the *L. plantarum* IMB19 strain was a polysaccharide (Formula I) having a polymer structure of a specific repeating unit included in CPS-100.

Accordingly, even yet another aspect of the present invention pertains to a polysaccharide represented by Formula I below:

$$-[\text{D-B-I-F-G-C-E-H-A-}]_n- \qquad \text{[Formula I]}$$

in Formula I,

A and D are galactose,

B, C, E, G, and H are rhamnose,

F is N-acetylglucosamine,

I is glucose, and n is an integer of 1 or more.

In the present invention, the polysaccharide of Formula I is a polymer structure of a repeating unit represented by [-D-B-I-F-G-C-E-H-A-] in Formula I.

In the present invention, when n in Formula I is 2 or more, the repeating units may be connected without limitation in various ways, in addition to direct covalent bonding. For example, the repeating units may be connected through chemical bonding, such as a glycosidic linkage or a phosphodiester linkage, or may be connected via a linker.

In the present invention, when n in Formula I is 2 or more, the repeating units ([-D-B-I-F-G-C-E-H-A-]) may be connected through a glycosidic linkage (—O—) between A and D.

In the present invention, when n in Formula I is 2 or more, the repeating units ([-D-B-I-F-G-C-E-H-A-]) may be connected through a phosphodiester linkage between A and D.

In the present invention, when n in Formula I is 2 or more, carbon at position 1 in A of a repeating unit and carbon at position 6 in D of another repeating unit may be connected through a phosphodiester linkage.

In the present invention, at least one of A and D of Formula I may be phosphorylated, and preferably, in the case of A, the hydroxyl group of carbon at position 1 is phosphorylated, and in the case of D, the hydroxyl group of carbon at position 6 is phosphorylated.

In the present invention, the galactose that is used includes galactose or derivatives thereof, which are generally present in nature. For example, in the present invention, the galactose may be provided in the form of an isomer in an α configuration or β configuration, or a D configuration or L configuration, preferably α-galactose, and more preferably α-D-galactose, but is not limited thereto.

In the present invention, the rhamnose that is used includes all of rhamnose or derivatives thereof, which are generally present in nature. For example, in the present invention, the rhamnose may be provided in the form of an isomer in an α configuration or β configuration, or a D configuration or L configuration, preferably α-rhamnose, and more preferably α-L-rhamnose, but is not limited thereto.

In the present invention, the N-acetylglucosamine that is used includes all of N-acetylglucosamine or derivatives thereof, which are generally present in nature.

In the present invention, the glucose that is used includes all of typical glucose or derivatives thereof. For example, in the present invention, the glucose may be provided in the form of an isomer in an α configuration or β configuration, or a D configuration or L configuration, preferably glucose having a β configuration, and more preferably D-glucose, but is not limited thereto.

As used herein, the term "derivative" refers to a compound, the structure of which is sufficiently similar to the structure of the compound disclosed herein and which, based on the similarity therebetween, exhibits an activity and end use identical or similar to the claimed compound, or, as a precursor, a compound having a structure derived from the structure of the parent compound (e.g. the compound described herein, the polysaccharide of Formula I), which is expected to elicit an activity and end use identical or similar to the claimed compound. Examples of the derivative may include, but are not limited to, salts, isomers, esters, amides, salts of esters or amides, N-oxides, and the like of the parent compound.

In the present invention, D and B (D-B) and B and I (B-I) of Formula I may be connected through an α-1,3-glycosidic linkage.

In the present invention, I and F (I-F) of Formula I may be connected through a β-1,6-glycosidic linkage.

In the present invention, F and G (F-G), G and C (G-C), C and E (C-E), and E and H (E-H) of Formula I may be connected through an α-1,2-glycosidic linkage.

In the present invention, H and A (H-A) of Formula I may be connected through an α-1,6-glycosidic linkage.

In the present specification, the connection is represented as α or β depending on the linkage orientation, and the numbers adjacent thereto refer to respective carbon numbers linked (—O—) in two monosaccharides.

In the present invention, n in Formula I is an integer of 1 or more, preferably an integer of 1 to 10, and more preferably 4.

In the present invention, the polysaccharide may have the structure of Formula II below.

In the present invention, the polysaccharide of Formula I is capable of inhibiting tumor growth.

[Formula II]

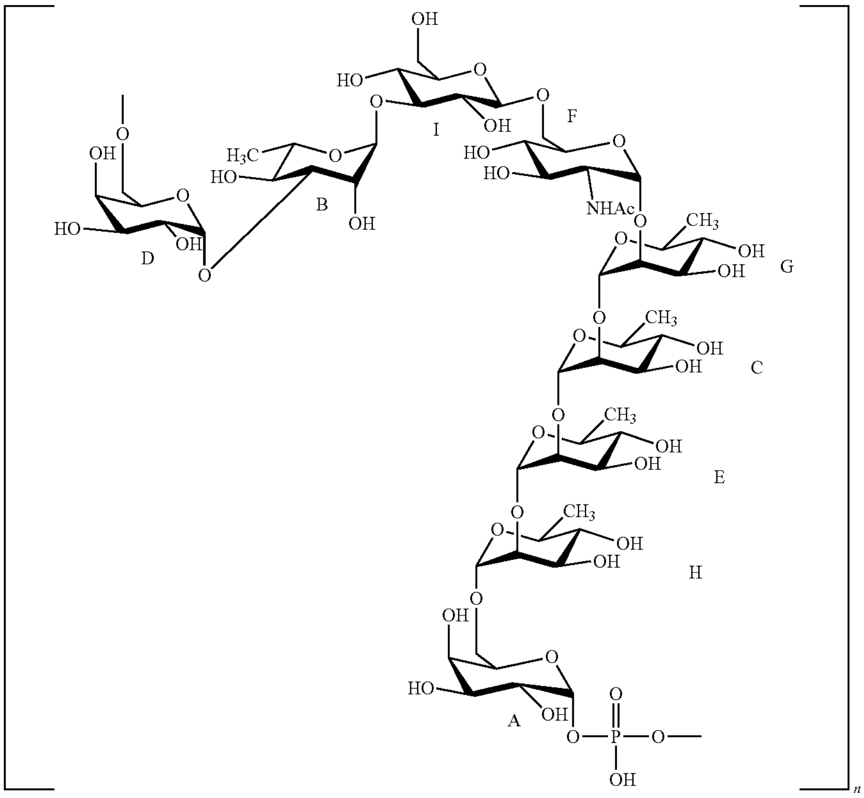

n being an integer of 1 or more.

In the present invention, n in Formula II is preferably an integer of 1 to 10, and more preferably, n is 4.

In an embodiment of the present invention, it has been confirmed that the average degree of polymerization of the polysaccharide of Formula I included in CPS-100, which is an effective fraction of the capsular polysaccharide, was about 4, and also that the average molecular weight thereof was about 6.0 kDa. Each repeating unit ([-D-B-I-F-G-C-E-H-A-]) was confirmed to have a molecular weight (MW) of about 1.5 kDa.

In the present invention, the polysaccharide of Formula I may have a molecular weight of at least about 1.5 kDa, preferably about 1.5 kDa to about 15 kDa, and more preferably about 4 kDa, depending on the degree of polymerization, the extent of phosphorylation, etc.

In the present invention, the polysaccharide may be derived from a *Lactobacillus plantarum* IMB19 strain having accession number KCTC 14337BP.

In the present invention, the polysaccharide of Formula I may have immune-enhancing activity and/or anti-tumor activity. More specifically, the *L. plantarum* IMB19 strain may have various immune-enhancing and anti-tumor activities such as i) induction of T-cell differentiation to an inflammatory phenotype such as induction of helper T cells and inhibition of Treg cell differentiation, ii) stimulation of CD8+ T cells, enhancement of activity, and improvement of intratumoral infiltration, iii) inhibition of Treg cell activity, iv) increased macrophage infiltration in tumors, and v) activation of macrophages to inflammatory cells and reprogramming from M2 to M1 macrophages, but is not limited to such mechanisms.

In the present invention, the polysaccharide may be produced/separated using the strain of the present invention by those skilled in the art, and the polysaccharide of the present invention may be induced or synthesized through other chemical or biological methods.

Furthermore, it is apparent that modification of the structure of CPS for improvement of pharmacokinetic and/or pharmacodynamic properties of the polysaccharide of the present invention or for clinical formulation thereof (e.g. solubility) may be performed. For example, i) addition of at least one functional group, ii) modification of a carbon chain, iii) addition of at least one hydrogen or hydroxyl group, iv) modification of an end group (e.g. addition of a signal molecule such as a dye, etc.), and v) binding to other known sugar molecules (e.g. formulation for oral or systemic delivery, etc.) may be performed, but the present invention is not limited thereto.

Therefore, the polysaccharide of the present invention is not limited to the polysaccharide of Formula I or Formula II, and is to be conceptually understood as including all variants, derivatives, analogues, and the like of Formula I or Formula II, so long as it exhibits the immunostimulatory and immune-enhancing effects of the present invention.

Accordingly, a further aspect of the present invention pertains to a composition for immune modulation containing the polysaccharide of Formula I as an active ingredient.

In addition, a further aspect of the present invention pertains to an immunomodulation method including administering the polysaccharide to a subject.

In addition, a further aspect of the present invention pertains to the use of the polysaccharide for immune modulation.

In addition, a further aspect of the present invention pertains to the use of the polysaccharide for the manufacture of a composition for immune modulation.

Below, unless special definitions of terms are provided, the terms are to be understood as having meanings understood by those skilled in the art or meanings defined according to other aspects of the present invention.

In the present invention, the composition for immune modulation may be used for immune stimulation or immune enhancement.

In the present invention, the composition for immune modulation may be a composition for immune stimulation or immune enhancement.

In the present invention, the composition for immune modulation may be prepared and used in the form of a pharmaceutical composition or a food composition for the purpose of preventing, ameliorating, or treating not only tumors and infectious diseases, but also immune diseases caused by or symptomatic of immune reduction/suppression. Here, the amount and form of use may be appropriately adjusted depending on the purpose.

In an embodiment of the present invention, the half-maximal effective concentration (EC50) of the polysaccharide was confirmed to be 3.16 μM. Therefore, it is preferred that the composition for immune modulation of the present invention contain the polysaccharide in an amount of 3.16 μM or more.

In the present invention, the composition for immune modulation may be used in combination with other pharmaceutical compositions or food compositions, or may be used as an adjuvant. Examples of the other pharmaceutical compositions include, but are not limited to, immunotherapy-related immunotherapeutic agents, immune-cell therapeutic agents, and the like. Examples of the other food compositions may include, but are not limited to, fermented foods, functional health foods such as nutritional supplements, and the like.

In the present invention, the composition for immune modulation may further include other probiotic strains, compounds, adjuvants, additives, carriers, excipients, etc., in addition to the polysaccharide of the present invention.

Still a further aspect of the present invention pertains to a pharmaceutical composition for preventing or treating a tumor or an infectious disease containing the polysaccharide of Formula I of the present invention as an active ingredient.

In addition, still a further aspect of the present invention pertains to a method of preventing or treating a tumor or an infectious disease including administering the polysaccharide to a subject.

In addition, still a further aspect of the present invention pertains to the use of the polysaccharide for the prevention, amelioration, or treatment of a tumor or an infectious disease.

In addition, the present invention pertains to the use of the polysaccharide for the manufacture of a pharmaceutical composition for the prevention or treatment of a tumor or an infectious disease.

As used herein, the term "tumor" refers to a phenomenon by which cells become autonomous and excessively proliferate by deviating from the body's regulatory mechanisms, or neoplasms or hyperplasia generated thereby. The tumor includes, for example, all of benign, premalignant, and malignant tumors, and more specific examples thereof include histiocytoma, glioma, astrocytoma, osteoma, various types of cancer, for example, lung cancer, small-cell lung cancer, gastric cancer, gastrointestinal cancer, bowel cancer, colon cancer, rectal cancer, pancreatic cancer, breast cancer, skin cancer, ovarian cancer, prostate cancer, testicular cancer, liver cancer, kidney cancer, bladder cancer, pancreatic cancer, brain cancer, sarcoma, osteosarcoma, melanoma, lymphoma (Hodgkin's lymphoma, FL, MCL, MZBL, CLL, T-ALL, AML, ALL, etc.), blood cancer, leukemia, psoriasis, bone disease, fibroproliferative disorder, atherosclerosis, etc., but the present invention is not limited thereto.

As used herein, the term "infectious disease" refers to a pathogen-associated disease induced or exacerbated by infection with various pathogens. For example, the infectious disease may be a disease induced or aggravated by infection with a virus, bacterium, fungus, protozoan, parasite, prion, or protein aggregate, but the present invention is not limited thereto.

The pharmaceutical composition of the present invention exhibits preventive or therapeutic effects and anti-inflammatory effects on various diseases through the aforementioned immune-enhancing effect and/or anti-tumor effect of the polysaccharide of Formula I, which is an active ingredient thereof.

The pharmaceutical composition may further include suitable carriers, excipients, and diluents commonly used in pharmaceutical compositions, in addition to containing the polysaccharide of Formula I as an active ingredient thereof.

The carriers, excipients and diluents that may be included in the composition include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. When formulating the composition, it is usually prepared using a diluent or excipient such as a filler, an extender, a binder, a wetting agent, a disintegrant, a surfactant, etc.

The pharmaceutical composition according to the present invention may be formulated and used in various forms according to a typical method. Suitable formulations include tablets, pills, powders, granules, sugar-coated tablets, hard or soft capsules, solutions, suspensions, emulsions, injections, oral formulations such as aerosols, external preparations, suppositories, and sterile injection solutions, but the present invention is not limited thereto.

The pharmaceutical composition according to the present invention may be formulated in a suitable dosage form using a pharmaceutically inert organic or inorganic carrier. Specifically, when the formulation is a tablet, coated tablet, sugar-coated tablet, or hard capsule, it may include lactose, sucrose, starch or derivatives thereof, talc, calcium carbonate, gelatin, stearic acid, or salts thereof. Also, when the formulation is a soft capsule, it may include vegetable oils, waxes, fats, and semi-solid and liquid polyols. Also, when the formulation is in the form of a solution or syrup, it may include water, polyol, glycerol, and vegetable oil.

The pharmaceutical composition according to the present invention may further include a preservative, a stabilizer, a wetting agent, an emulsifier, a solubilizing agent, a sweetener, a colorant, an osmotic pressure adjuster, an antioxidant, and the like, in addition to the carrier described above.

The pharmaceutical composition according to the present invention is administered in a pharmaceutically effective amount. In the present invention, "pharmaceutically effective amount" means an amount sufficient to treat a disease at a reasonable benefit/risk ratio applicable to medical treatment, and the effective dose level is determined depending on various factors including the type of patient's disease, severity of disease, drug activity, sensitivity to drugs, administration time, administration route, excretion rate, treatment period, and drugs used simultaneously therewith, and other factors well-known in the medical field. The pharmaceutical composition according to the present invention may be administered as an individual therapeutic agent or in combination with other therapeutic agents, may be administered sequentially or simultaneously with conventional therapeutic agents, and may be administered one or multiple times. In consideration of all of the above factors, it is important to administer the composition in the minimum amount capable of obtaining the maximum effect without side effects, which may be easily determined by those skilled in the art.

The pharmaceutical composition of the present invention may be administered to a subject through any of various routes. The mode of administration may be, for example, subcutaneous, intravenous, intramuscular, intrauterine dural, or intracerebrovascular injection. The pharmaceutical composition of the present invention is determined depending on the type of drug as an active ingredient, in consideration of various factors such as the disease to be treated, the route of administration, the patient's age, gender, and body weight, and the severity of disease.

The mode of administration of the pharmaceutical composition according to the present invention may be easily selected depending on the dosage form, and oral or parenteral administration or topical or systemic administration is possible. The dosage thereof may vary depending on the patient's age, gender, and body weight, the severity of disease, and the route of administration.

The composition of the present invention may be administered in combination with other therapeutic regimens or therapeutic agents. When used for the prevention or treatment of tumors, the other therapy or therapeutic agent is preferably an immunotherapy or immune-cell therapeutic agent, but is not limited thereto, and may be used in various combinations according to the judgment of a clinician.

Even still a further aspect of the present invention pertains to a food composition for immune enhancement containing the polysaccharide of Formula I as an active ingredient.

In addition, even still a further aspect of the present invention pertains to the use of the polysaccharide for the manufacture of a food composition for immune enhancement.

The food composition of the present invention is capable of maintaining immune function homeostasis by enhancing or improving immune activity.

The food composition of the present invention may be a functional health food exhibiting an effect of preventing or ameliorating a tumor or an infectious disease.

The food composition may further include a physiologically acceptable carrier, the type of which is not particularly limited, and any carrier commonly used in the art may be used.

Moreover, the composition may include additional ingredients that are commonly used in food compositions to improve smell, taste, visual appearance, and the like. For example, it may include vitamins A, C, D, E, B1, B2, B6, B12, niacin, biotin, folate, pantothenic acid, and the like. Also, it may include minerals such as zinc (Zn), iron (Fe), calcium (Ca), chromium (Cr), magnesium (Mg), manganese (Mn), copper (Cu), chromium (Cr), and the like. Also, it may include amino acids such as lysine, tryptophan, cysteine, valine, and the like.

Also, the composition may include food additives, such as preservatives (potassium sorbate, sodium benzoate, salicylic acid, sodium dehydroacetate, etc.), disinfectants (bleaching powder, high bleaching powder, sodium hypochlorite, etc.), antioxidants (butylhydroxyanisole (BHA), butylhydroxy toluene (BHT), etc.), colorants (tar pigment, etc.), color development agents (sodium nitrite, sodium nitrite, etc.), bleaches (sodium sulfite), seasonings (MSG, etc.), sweeteners (dulcin, cyclamate, saccharin, sodium, etc.), flavorings (vanillin, lactones, etc.), expansion agents (alum, D-potassium hydrogen tartrate, etc.), strengthening agents, emulsifiers, thickening agents (thickeners), film-forming agents, gum base agents, foam inhibitors, solvents, improving agents, and the like. These additives may be selected depending on the type of food, and may be used in appropriate amounts.

The food composition may further include a food supplement additive that is acceptable for human consumption, in addition to the polysaccharide of Formula I as an active ingredient thereof, and may be used along with other foods or food ingredients, and may be used appropriately according to a typical method. The amount of the active ingredient that is included therein may be appropriately determined according to the purpose of use thereof (prevention, health, or therapeutic treatment).

In an embodiment of the present invention, it has been confirmed that the strain and the strain-derived polysaccharide according to the present invention induced expression of IFN-γ in cells and suppressed expression of IL-10, both in vivo and in vitro, thereby stimulating and enhancing an immune response.

In another embodiment of the present invention, it has been confirmed that the strain and the strain-derived polysaccharide were capable of activating CD8+ T cells via DCs and also that activation of CD+8 T cells was significantly reduced in the absence of the MyD88 signaling system.

In still another embodiment of the present invention, it has been confirmed that Th17 cells were capable of being induced through co-culture of DCs primed with the strain and the strain-derived polysaccharide and naive CD4+ T cells.

Therefore, yet a further aspect of the present invention pertains to a method of producing inflammatory T cells, including:

(a) priming antigen-presenting cells with the *L. plantarum* IMB19 strain and/or the polysaccharide of Formula I; and (b) co-culturing the primed antigen-presenting cells with T cells.

As used herein, the term "antigen-presenting cell" refers to a cell inducing differentiation by receiving an antigen, processing the same, and presenting the antigen-derived fragment along with an antigen-presenting molecule such as an MHC class±molecule to T cells. Examples of the antigen-presenting cells include, but are not limited to, macrophages, B cells, dendritic cells (DCs), Langerhans cells, and the like.

In the present invention, the T cells in step (b) are preferably naive T cells, more preferably naive CD8+ T cells or naive CD4+ T cells, but are not limited thereto.

As used herein, the term "inflammatory T cell" refers to a T cell that induces or boosts an immune response, either directly or in the pre-inflammatory stage. Preferably, the inflammatory T cells are cytotoxic T cells or helper T cells (Th cells), more preferably IFN-γ+ CD8+ T cells or CD4+ RORγ+ Th17 cells.

Accordingly, still yet a further aspect of the present invention pertains to a cell therapeutic agent for preventing or treating a tumor or an infectious disease containing the inflammatory T cells produced through the above method as an active ingredient.

In an embodiment of the present invention, it has been confirmed that MHC I, MHC II, CD68, iNOS2, and CD40 were significantly upregulated when splenic macrophages or M2-phenotype macrophages were exposed to CPS, enabling reprogramming from immune-suppressing M2-phenotype macrophages to M1-phenotype macrophages in the tumor microenvironment.

Accordingly, even yet a further aspect of the present invention pertains to a method of producing M1-phenotype macrophages including differentiating macrophages into M1-phenotype macrophages by treating macrophages with the *L. plantarum* IMB19 strain and/or the polysaccharide of Formula I and obtaining the activated M1-phenotype macrophages.

As used herein, the term “macrophage” refers to a type of white blood cell that is capable of phagocytosis by swallowing and digesting pathogens, foreign substances, microorganisms, cancer cells, abnormal proteins, etc., and also functions as an antigen-presenting cell for adaptive immunity, in addition to innate immune responses.

Macrophages are classified as either M1-phenotype macrophages, which are inflammatory macrophages, or M2-phenotype macrophages, which are anti-inflammatory macrophages, and are involved in the balance of immune stimulation and suppression. In particular, it has been reported that M2-phenotype macrophages contribute to tumor growth (Ann. Oncol. 28, xii18-xii32 (2017); Front Oncol. 9, 421 (2019)). The M1-phenotype macrophages collectively refer to macrophages that are activated through IFN-γ secreted by NK cells or Th1, MyD88 pathways through PAMP recognition of TLR, etc. and thus stimulate and induce immune responses such as antigen presentation, induction of inflammatory gene and inflammatory chemokine secretion, and the like. The M2-phenotype macrophages (immunosuppressive macrophages) are macrophages differentiated by IL-4, IL-13, etc., exhibit immunosuppressive activity, and are involved in tissue reconstruction and wound healing.

In the present invention, the macrophages in step (a) may be naive macrophages or M2-phenotype macrophages.

In the present invention, the M1-phenotype macrophages include, without limitation, macrophages activated to an inflammatory phenotype to stimulate or induce an immune response. The M1-phenotype macrophages may be classified depending on a change in the gene expression profile; for example, the M1-phenotype macrophages may be characterized in that expression of at least one selected from the group consisting of MHC I, MHC II, CD68, iNOS2, and CD40 is upregulated, but the present invention is not limited thereto.

As used herein, the expression “differentiation of macrophages” refers to activation or conversion of macrophages from an existing gene expression profile to a phenotype exhibiting another gene expression profile. The term “differentiation” is used with a meaning including not only activation or polarization of naive macrophages, but also reprogramming of macrophages that have already been activated and exhibit a specific phenotype (e.g. M1 phenotype or M2 phenotype).

As used herein, the term “upregulated” means that the expression of a specific gene or protein is improved compared to the phenotype before conversion of macrophages.

Accordingly, even still yet a further aspect of the present invention pertains to a cell therapeutic agent for preventing or treating a tumor or an infectious disease containing the inflammatory macrophages produced through the above method as an active ingredient.

EXAMPLES

A better understanding of the present invention may be obtained through the following examples. These examples are merely set forth to illustrate the present invention, and are not to be construed as limiting the scope of the present invention, as will be apparent to those skilled in the art.

Example 1: Materials and Methods

1. Bacterial Culture and Identification

Kimchi was homogenized, and a suspension thereof was obtained. Thereafter, serial dilution, streaking on MRS broth and agar, and culture at 37° C. for 48 hours were performed, so colonies were isolated, followed by further culture for various analyses.

*L. plantarum* IMB19 was cultured in MRS broth at 37° C. for 24-36 hours. For TEM (transmission electron microscopy), the bacteria were cultured, streaked on MRS-1.5% agar (Neogen Corp., USA), and cultured for 24-30 hours. Bacterial colonies were dropped onto 2000 mesh graphene-coated copper grids. TEM imaging was performed at 80 kV using a JEOL1220 and a Hitachi HT7700.

For identification, the cell morphology of the selected isolated strain was observed using a microscope, genetic characteristics thereof were analyzed using genomic DNA, and 16s rRNA sequencing was performed by Macrogen (Korea).

The 16S rRNA gene was amplified through direct PCR using universal primers of forward (27F primer) 5'-AGAGTTTGATCMTGGCTCAG-3' and reverse (1492R primer) 5'-TACGGYTACCTTGTTACGACTT-3'.

2. Primary Cell-Based Testing 2-1. In-Vitro Splenocyte Stimulation

All animal experiments and procedures were performed in accordance with the ethical regulations and with the approval of the Institutional Animal Care and Use Committee of Pohang University of Science and Technology (POSTECH). C57BL/6 mice were housed and bred in a pathogen-free animal barrier facility and used at 6-8 weeks of age. The spleens were harvested therefrom and gently ground to release splenocytes. The cells were suspended, subjected to RBC lysis with ammonium chloride buffer, and resuspended in a complete RPMI medium (Welgene, S. Korea) containing 10% FBS (Hy-Clone, Australia). The cells were plated at a density of 200 k/well in 200 μL of medium/well containing 10 ng/mL of anti-CD3 (Bio-xCell, USA) and 2.5 ng/mL of GM-CSF (Peprotech, USA) in a 96-well plate. Fractionated CPS-100, unfractionated total CPS (tCPS), LPS (liposaccharide derived from *E. coli* 0111:B4, Invivogen, USA), and medium were added as needed, followed by culture at 37° C. and 5% $CO_2$ for 48 hours. In accordance with the manufacturer’s instructions, the supernatant was collected after centrifugation and frozen for cytokine estimation through enzyme-linked immunosorbent assay (ELISA, e-Bioscience, Ready-SET-Go! ELISA kits).

2-2. Immune Cell Co-Culture System

Isolation of splenocytes was performed as described above. CD11c+ APC (Miltenyi Biotec) and naive CD4+ T cells (Stem Cell Technologies) were isolated according to the manufacturer’s protocol. APCs were cultured with a probiotic strain at 37° C. and 5% $CO_2$ for 18 to 20 hours. Then, the probiotic strain was washed, and primed APC and CD4+ T cells were co-cultured therewith under specific conditions.

3. Safety Evaluation 3-1. Hemolysis Test

*L. plantarum* IMB19 was grown under optimal growth conditions, streaked on 5% sheep blood agar (Hanil, Komed), and then cultured for 48 hours. Alpha (α) 2 hemolysis was regarded as partial degradation of hemoglobin in red blood cells (did not represent actual hemolysis), beta (β) hemolysis, observed as a clear area on the agar plate, was regarded as complete degradation of hemoglobin in red blood cells, and gamma (γ) hemolysis was regarded as lack of hemolysis. *Bacillus cereus* ATCC 27348 was used as a positive control.

3-2. Gelatin Degradation Test

The basic protocol was performed according to ASM Science Recommendation (Dela Cru et al., 2012). *L. plantarum* IMB19 grown under optimal growth conditions was inoculated in a gelatin medium with an inoculation loop and cultured at 30° C. for up to 5 days, and gelatin liquefaction and bacterial growth were checked daily. Gelatin is generally liquefied at a temperature equal to or higher than 28° C. The tube was stored in a refrigerator for 30 minutes to determine whether the liquefaction was due to gelatinase activity. Thereafter, the tube was tilted to observe whether the gelatin was degraded. When the gelatin is degraded, it remains in a liquid state even after exposure to low temperatures. *Bacillus cereus* ATCC 11778 was used as a positive control.

3-3. Biogenic Amine Analysis

*L. plantarum* IMB19 was grown under optimal conditions and streaked on a special medium containing precursors of histamine, cadaverine, tyramine, and putrescine according to Bover-Cid and Holzapfel (Bover-Cid et al., 1999), followed by culture at 37° C., 30° C., and 23° C. for 4 days. Thereafter, whether the analysis results were positive or negative was determined by observing changes in the color of the medium. *E. coli* ATCC 25922 was used as a positive control. Culture was performed on agar using a basic culture medium containing any one of ornithine, lysine, tyrosine, and histidine together with a bromocresol purple indicator.

3-4. Antibiotic Resistance Test

The basic protocol was performed according to ISO recommendations (ISO-10932, 2010). The broth dilution method was used to evaluate the minimum inhibitory concentration (MIC) of the strain against antibiotics.

In culture microdilution, test organisms were cultured alone in a culture medium, and all organisms were washed with 1×PBS. Bacterial solutions washed with PBS were adjusted at optical density (OD) of 0.01-0.02 at 600 nm. 10 μL (1-2×$10^5$ CFU) of the strain was inoculated into a 96-well plate containing 200 μL of an LSM broth medium along with antibiotics.

The strain was considered susceptible when inhibited at a specific antibiotic concentration equal to or lower than a cut-off value according to a parameter set by the European Food Safety Authority (EFSA, 2018), and was considered resistant when not inhibited at a specific antibiotic concentration higher than a cut-off value established by regulations.

4. Isolation of Crude Capsular Polysaccharide (CPS)

Isolation of crude CPS was performed with a modification of the conventionally described method (Verma et al., 2018). Bacterial cultures were centrifuged and sonicated using a Branson digital sonicator for 15 minutes at 10% amplitude and a pulse of 10 sec. The supernatant was treated with trichloroacetic acid (0.5% w/v) at 4° C. overnight. The sample was centrifuged at 6000 rpm for 20 minutes, and 100% ethanol was added to the supernatant at a ratio of 3:1 to precipitate the crude polysaccharide at −20° C. The precipitate was resuspended in a Tris buffer (100 mM, Sigma Aldrich, USA) containing magnesium chloride (20 mM, Sigma Aldrich) and calcium chloride (20 mM, Sigma Aldrich) in distilled water without endotoxins, and was then treated with DNAse (0.1 mg/mL, Roche, Germany) and RNAse (0.4 mg/mL, Sigma Aldrich, USA) at 37° C. for 4-6 hours. Pronase (0.3 mg/mL, Sigma-Aldrich, USA) was added thereto to degrade protein contaminants, followed by culture overnight at 4° C. The sample was treated with trichloroacetic acid (1-2% w/v) at 37° C. for 30 minutes, thus removing total protein including the added enzyme. All of the polysaccharides in the sample from which the protein was removed were reprecipitated through ethanol precipitation. The pellets were resuspended in endotoxin-free water and dialyzed at 4° C. for 48 hours while water was exchanged twice a day (MW cut-off 12,000 Da). The total CPS fraction was obtained through freeze-drying at a final yield of 20 mg per liter of culture.

5. GC-MS Analysis Conditions

All chemical derivatives were analyzed through gas-liquid chromatography (GLC-MS) using an Agilent 7820A (Santa Clara, Calif., USA) equipped with a mass selective detector 5973N and a Zebron ZB-5 capillary column (Phenomenex, 30 m×0.25 mm i.d., film thickness: 0.25 μm, flow rate: 1 mL/min, and He as carrier gas). Electron impact mass spectra were recorded with ionization energy of 70 eV and ionization current of 0.2 mA. The temperature program that was used was as follows: 150° C. for 5 min, from 150° C. to 300° C. at 10° C./min, and 300° C. for 12 min.

6. NMR Acquisition Parameters

For structural analysis of the isolated polysaccharide, NMR spectra were recorded in $D_2O$ using a Bruker 600 MHz spectrometer equipped with a reverse cryo-probe inclined along the Z-axis. Spectra were measured at 298K or 310K, corrected with acetone ($^1$H 2.225 ppm; $^{13}$C 31.45 ppm) as an internal standard, acquired using Topspin 2.0 software (Bruker), and processed and studied with Topspin 3.6. $^1$H-$^1$H DQ-COSY (dual quantum COZY spectrum, hereafter referred to as COSY), TOCSY, and NOESY spectra were collected with a data set of 2048×512 points (t1×t2), and TOCSY and NOESY spectra were collected through 24 scans with mixing times of 100 ms and 200 ms, respectively. Heteronuclear $^1$H-$^{13}$C HSQC, HMBC, and HSQC-TOCSY spectra were performed in $^1$H-detection mode using a data set of 2048×512 points. HSQC and HSQC-TOCSY were performed with multiple edits in the selection step in order to distinguish the density of $CH_2$ from other densities. HMBC was optimized for long-distance coupling constants using a low-pass J filter to suppress one-bond correlations, and a 60 ms delay was used for the evolution of long-range correlations. For HSQC-TOCSY, the mixing time was set to 100 ms. In all two-dimensional tests, the data matrix was expanded to 4092×2048 points and transformed by applying a qsine or sine window function.

7. Animal and Mouse Tumor Models

C57BL/6 & Balb/c mice were purchased and maintained at a POSTECH animal facility. Pmel-1 TCR transgenic, MyD88−/− and IL-6−/− mice were purchased from Jackson Lab and maintained at the POSTECH animal facility. The C57BL/6-derived melanoma cell line B16.F10 and the Balb/c-derived breast cancer cell line EMT-6 were obtained from ATCC and maintained according to the provided protocol. Syngeneic tumor models were obtained through subcutaneous injection of 200,000 B16.F10 tumor cells or 500,000 EMT-6 cells. The tumor size was measured every other day until the endpoint, and the tumor volume was calculated using length×width2×0.5. For the initial infiltration analysis of innate immune cells, tumor cells were injected subcutaneously at 5 ml/mouse, and tumor cells were analyzed 40 hours later. All experimental animal procedures were performed with the approval of the Institutional Animal Care and Use Committee (IACUC) of POSTECH.

8. Cell-Based In-Vitro Assay Method

Total cells harvested from spleens and/or lymph nodes were used for whole spleen cell culture or subjected to magnetic bead isolation (Miltenyi Biotec) so that CD11c+ dendritic cells, naive CD8+ T cells, or naive CD4+ T cells were enriched. Total splenocytes (200,000 cells/well) were cultured with bacteria at a 1:1 ratio in 96 plates, and the supernatant was harvested at 48 hours and used for ELISA (eBioscience Ready-SET-Go! kits). CD11c+ dendritic cells (200,000 cells/well) were primed with bacteria at an appropriate ratio for 18 to 20 hours, washed, added with T cells (200,000 cells/well), and cultured for 72 hours. As indicated, anti-CD3 at 0.01 μg/ml (BioXCell) and GM-CSF at 2.5 ng/ml (Peprotech) were added for stimulation of CD8+ T cells, and anti-CD3 at 0.1 μg/ml, GM-CSF at 10 ng/ml, IL2 at 100 U/ml, and TGFβ (Peprotech) were added for stimulation of CD4+ T cells.

For peritoneal macrophages, cells were harvested 5 days after intraperitoneal injection of 2% Biogel (Bio-Rad) and then cultured in vitro with 10 ng/ml of recombinant murine MCSF (Peprotech). For polarization of selectively activated macrophages, the cells were added with IL-4 (Peprotech) for 24 hours and then treated with CPS, LPS (lipopolysaccharide derived from *E. coli* 0111:B4, Invivogen), or Pam3CSk4 (Sigma).

9. Metagenomic Analysis and Whole-Genome Sequencing

Metagenomic analysis of fecal pellets of tumor-bearing SPF mice was outsourced (Macrogen, S. Korea). Whole-gene sequencing of bacteria was performed on the Illumina platform (Macrogen, S. Korea), and bacterial culture samples were sent directly for analysis. Bioinformatic analysis was also outsourced to Macrogen.

10. Classification of Tumor-Infiltrating Macrophages and Analysis of Gene Expression Profiles 500 μg of CPS was injected into mice twice at 24-hour intervals, after which $5\times10^6$ B16.F10 tumor cells were subcutaneously inoculated thereto. 40 hours after tumor inoculation, whole tumors, including infiltrating immune cells, were digested into single-cell suspensions in Liberase. Samples of 5-10 mice were collected from the same treatment group and stained with Fixable Viability-ef506 (eBioscience), CD45-AF488 (BioLegend, 30-F11), CD3-ef450 (eBioscience, 145-2C11), CD19-PB (eBioscience, 1D3), IA/IE-PECy7 (BioLegend, M5/114.15.2), CD11c-PE (eBioscience, N418), and CD11b-PerCpCy5.5 (BD, M1/70). Live $CD45^+CD3^-$ $CD19^-MHCII^{hi}CD11c^+$ $CD11b^+$ macrophages were placed in a medium supplemented with FBS, centrifuged, and stored in TRIzol (Sigma). The samples were analyzed for a gene expression profile in Macrogen, the average fold change of gene transcript levels between treatment groups was calculated, and genes with a fold change of 1.5 or more in the two comparisons were input to DAVID v6.7 (The Database for Annotation, Visualization and Integrated Discovery v6.7) for pathway analysis. Genes determined to have significantly enhanced immune function were displayed on a heatmap (p<0.05).

11. *Listeria monocytogenes* In-Vivo Cytotoxicity Assay

Analysis was performed through a conventionally known method. Specifically, *Listeria monocytogenes* expressing OVA peptide (LM-OVA) was injected at 5000 CFU/mouse into C57/B16 mice. Mice were fed with an *L. plantarum* IMB19 strain every other day. On day 6, splenocytes of naive C57/b16 mice were pulsed with OVA peptide, and cells pulsed or not pulsed with peptide were stained with CFSE or CTV, mixed at a 1:1 ratio, and administered intravenously to the infected mice. Mice infected with LM-OVA were sacrificed 2 hours later, splenocytes/lymph nodes were harvested, and the cell death rate of peptide-pulsed splenocytes was detected using flow cytometry.

12. Purification Using Chromatography

Isolated total capsular polysaccharides (tCPS: 28 mg) were purified through an anion exchange Q-Sepharose fast flow method (GE Healthcare; V=4.4 mL, flow: 16 mL/h). The resin was packed, washed in 1 M NaCl, and equilibrated with volumes of 10 mM NaCl. Then, total capsular polysaccharide (tCPS) was dissolved in 10 mM NaCl (5 mL) and adsorbed to the resin. Elution was performed stepwise by sequentially adding 16 mL of NaCl (10, 100, 200, 400, 700, and 1000 mM). The eluate eluted using NaCl at each concentration was collected, desalted through dialysis (cut-off 1 kDa), and freeze-dried. Six fractions eluted at respective NaCl concentrations were labeled as CPS-X (X being the NaCl concentration used for elution, mM).

Molecular weight measurements were extrapolated for CPS-100 using an Agilent 1100 HPLC system and a TSK G-5000 PWXL size exclusion column (30 cm×7.8 mm), equilibrated with 50 mM $NH_4HCO_3$ as an eluent (flow=0.8 mL/min), and the eluate was monitored using a refractive index detector. The column was calibrated by injecting dextran standards (50 μL of 1 mg/mL solution) having known molecular weights (12, 50, 150, and 670 kDa, respectively). The logarithm of the molecular weight was plotted against the elution volume, and the MW of the polysaccharide was calculated using the established linear relationship (Log PM=−0.811 mL+11.7; R2=0.98).

13. Statistical Analysis

Tumor growth curves were analyzed through two-way ANOVA using Sidak's multiple comparison post-test for comparison of two groups, Dunnett's multiple comparison post-test for comparison between multiple groups and controls, or Tukey's multiple comparison post-test for comparison of two or more groups. For other comparisons, an unpaired Student's t-test was used when comparing two groups, and Bonferroni correction for multiple tests and one-way ANOVA were used when comparing two or more groups. P<0.05 was considered statistically significant (*P<0.05, P<0.01, *P<0.001, ****P<0.0001). Statistical analysis was performed using GraphPad PRISM v8.0. Flow cytometry data were analyzed using Flow-jo software v10.1.

Example 2: Isolation and Identification of *L. plantarum* IMB19

*L. plantarum* IMB19 was isolated from homemade kimchi fermented using microorganisms derived from raw materials. In order to form colonies of *Lactobacillus* sp., serially diluted kimchi suspensions were streaked on MRS broth plates (De Man, Rogosa and Sharpe broth, Becton-Dickinson, USA). Cultured single colonies were isolated and further cultured in MRS broth. Because strains could not be distinguished from each other based on colony morphology, 14 isolated bacteria were subjected to PCR and 16s rRNA sequencing, and sequence similarity was confirmed using BLAST from NCBI. All of the isolated bacteria were found to be lactic acid bacteria (LAB). Among the isolated bacteria, a strain having at least 99% similarity to *L. plantarum* was identified, and also, many isolated bacteria were confirmed to have 99% similarity to *Weissella koreensis*. These results are consistent with conventional reports that the dominant species in kimchi are *L. plantarum* and *Weissella koreensis*.

The analyzed 16S rRNA sequence information of *L. plantarum* IMB19 is as follows.

*L. plantarum* IMB19 16S rRNA (785 Forward)
(SEQ ID NO: 3)

```
AGCGCTGGGATGATGCTAGTGTTGGAGGGTTTCCGCCCTTCAGTGCTGC
AGCTAACGCATTAAGCATTCCGCCTGGGGAGTACGGCCGCAAGGCTGAA
ACTCAAAGGAATTGACGGGGGCCCGCACAAGCGGTGGAGCATGTGGTTT
AATTCGAAGCTACGCGAAGAACCTTACCAGGTCTTGACATACTATGCAA
ATCTAAGAGATTAGACGTTCCCTTCGGGGACATGGATACAGGTGGTGCA
TGGTTGTCGTCAGCTCGTGTCGTGAGATGTTGGGTTAAGTCCCGCAACG
AGCGCA
ACCCTTATTATCAGTTGCCAGCATTAAGTTGGGCACTCTGGTGAGACTG
CCGGTGACAAACCGGAGGAAGGTGGGGATGACGTCAAATCATCATGCCC
CTTATGACCTGGGCTACACACGTGCTACAATGGATGGTACAACGAGTTG
CGAACTCGCGAGAGTAAGCTAATCTCTTAAAGCCATTCTCAGTTCGGAT
TGTAGGCTGCAACTCGCCTACATGAAGTCGGAATCGCTAGTAATCGCGG
ATCAGCATGCCGCGGTGAATACGTTCCCGGGCCTTGTACACACCGCCCG
TCACACCATGAGAGTTTGTAACACCCAAAGTCGGTGGGGTAACCTTTTA
GGAACCAGCCGCCTAAGGTGGGACAGATGATTAGGGTGAAGTCGTAACA
GGGTAAAACCGTAAAGATGTTCAACCCGCCACATCTGTCGCGTCTCCGT
CGTAGATATAAGAAAGCCAAAGGGCCTTTCTTCCATGGCTGGGTGTTCA
TGCAATAACATCGACCGGTTATCCACGACACAAGAAAGGATTACGTTGG
TCCTGGTTGTGCGCTCAGGTTTTATAGTGACAGCGGGCCTATTTGTATG
GTGTAAACCGGAGTGCTAACAATCTTCTACAAGAAACAGCCTGTACATA
AATTTACGGCATATATATACCGGAACGTGGCTTGGCCACGTATGTTATT
AACGCGGGCTGGCAGGAACTTACTAGGCCGTGCCATTCCGGTGTCAAAT
CCGACCGAATCCGGGGACTCGTCTCGCGGAAATGTGTTTCTTTTTAGAG
ACATGGATTCTTACAAACCGAGACCCTGTCATGCCCGGGATGAGGGTCT
GCCACTAACAACTTTCCGAACATGATGGGAAGAACCCCCTAACGGGCGC
CCACCTGGAGGAATTTGGGCCGGGGCACCACCGCCCGAGGTGGGGCGGA
AAACCCCCTCCAGGGGTCCCATCCTCAATTTTTCCGGGGGGGACCCCCC
TCCCCCCCAAAATGAGGGAAAACCCCCGGGGGGGCACCCCCAAAAGAAG
GAGAGCCCCCCACCCTCACTCTTCCCGCCCGGCGTGCGGGGGCGGGTTT
TTTTTTCTGTCAAAATAAATTTTGTGTTGTTTGTGTGTTCCTCCCCCCC
CCGCCGCGGGGGCGGGGTTGTACTTTTTTCCCTCTCCATCCCCCCCCCA
CCACAAAAGAAAAGGAGGGGACGACACCCACAGTGGGTGTGTTTTT
```

*L. plantarum* IMB19 16S rRNA (907 Reverse)
(SEQ ID NO: 4)

```
TTGACGGGGGGGTCTCCAGGCGGAATGCTTAATGCGTTAGCTGCAGCAC
TGAAGGGCGGAAACCCCCCAACACTTAGCATTCATCGTTTACGGTATGG
ACTACCAGGGTATCTAATCCTGTTTGCTACCCATACTTTCGAGGOTGAG
CGTCAGTTAGAGACCAGACAGCCGCCTTCGCCACTGGTGTTCTTCCATA
TATCTACGCATTTCACCGCTACACATGGAGTTCCACTGTCCTCTTCTGC
```

-continued

```
ACTCAAGTTTCCCAGTTTCCGATGCACTTCTTCGGTTGAGCCGAAGGCT
TTCACATCAGACTTAAAAAACCGCCTGCGCTCGCTTTACGCCCAATAAA
TCCGGACAACGCTTGCCACCTACGTATTACCGCGGCTGCTGGCACGTAG
TTAGCCGTGGCTTTCTGGTTAAATACCGTCAATACCTGAACAGTTACTC
TCAGATATGTTCTTCTTTAACAACAGAGTTTTACGAGCCGAAACCCTTC
TTCACTCACGCGGCGTTGCTCCATCAGACTTTCGTCCATTGTGGAAGAT
TCCCTACTGCTGCCTCCCGTAGGAGTTTGGGCCGTGTCTCAGTCCCAAT
GTGGCCGATTACCCTCTCAGGTCGGCTACGTATCATTGCCATGGTGAGC
CGTTACCCCACCATCTAGCTAATACGCCGCGGGACCATCCAAAAGTGAT
AGCCGAAGCCATCTTTCAAACTCGGACCATGCGGTCCAAGTTGTTATGC
GGTATTAGCATCTGTTTCCAGGTGTTATCCCCCGCTTCTGGGCAGGTTT
CCCACGTGTTACTCACCAGTTCGCCACTCACTCAAATGTAAATCATGAT
GCAAGCACCAATCAATACCAGAGTTCGTTCGACTTGCATGTATTAGGCA
CGCCGCCAGCGTTCGTCCTGACAGAGAGAAAAAAAAAAAAAAAAAAAGGG
CCGGGGGGATCGGGGGGGGGGGGGGGGGGGGTGAGGGGTTGAGGGGGGG
GGGGGGGGGGGGGGGGGGGGGGGGGGGGGGGGGGGGGGGGGGGGGGGGG
GGGGGGGGGGGGGGGGGGGGGGGGGGGGGGGGGGGGGGGGGGGGGGGGG
GGGGGGGGGGGGGGGGTGTGTGGGGGGGGGGGGGTTGTTGTTTTTGTTT
GGGGGGGGGGTTGTTTTTTGTGTGTGTTTTGTTGTTTGTTTGGGGGTGT
GTTTTGTTGTGGGGTGGGGTGTTGGGGGGGTTGGGGGGGGGGTGTTGTT
TGGGGGGGGTGGGGGGGGGGGTTTTTTTGTTGTTGTGTGGTTGTGTGTT
GTGTGGTGGGTGGGGGGGGTGGTGTGTGTGTGGGGGTGGGGGGTGTTTG
GTGGGGGGGGGGTTGTTGTGGGGGGGTGGTGTTTGTTTTTTGTTTTTTT
TTGTGTGTGGGGGGGGGGGGTGGGGGGTGGTTTGTGGGGTGTTGTTTGT
GTGTGGTTGGTGGTGGTGTGTGGGGGGGTTGGGGGGGGGGGGGTTGTCT
TTTTTGTTGGTGTTGGGTGTTTGTTGGTGTTGGTGTGTGGTGGGGTGGT
GTGGTGGGTGGGTGCTTGTTGTGTGTGTGGTGTGT
```

Example 3: Selection of *L. plantarum* IMB19

Figure 1:
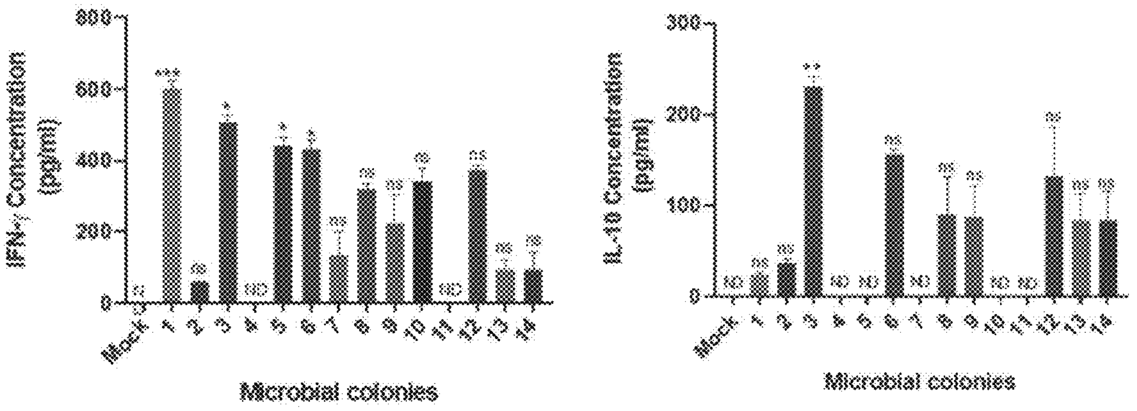
FIG. 1 shows the levels of inflammatory or anti-inflammatory cytokines in splenocytes upon treatment with a strain derived from kimchi, in which stepwise dilutions of the kimchi suspension were made, streaked on MRS-agar plates, and cultured at 37° C. for 48 hours, after which strains were obtained from 14 colonies and further cultured in MRS broth for 24 hours, and splenocytes were mixed with each strain at a ratio of 1:10 and cultured at 37° C. and 5% $CO_2$ for 48 hours, activation of splenocytes being evaluated by measuring cytokine levels in the culture supernatants through ELISA, data being mean±SEM values (n=2), and statistical significance being calculated for Mock through one-way ANOVA, *p<0.5, **p<0.01, *p<0.001.

In order to confirm the immunostimulatory effect of the isolated bacteria on immune cells, the effect of the bacterial culture isolate on murine splenocytes was tested, so bacteria having a stimulatory effect on immune cells were identified. After total splenocytes were cultured with the isolated bacteria for 48 hours, cytokine levels were measured in the culture supernatant. The effect of the isolated bacteria on immune cells was evaluated using IFN-γ as a well-known inflammatory marker and IL-10 as an anti-inflammatory cytokine. Among all of the isolated bacteria, a novel *Lactobacillus plantarum* strain that induces a negligible level of IL-10 and a very high level of IFN-γ was selected and named *L. plantarum* IMB19 (FIG. 1, colony 1).

Example 4: Analysis of Microbiological and Biochemical Properties of *L. plantarum* IMB19

Figure 2:
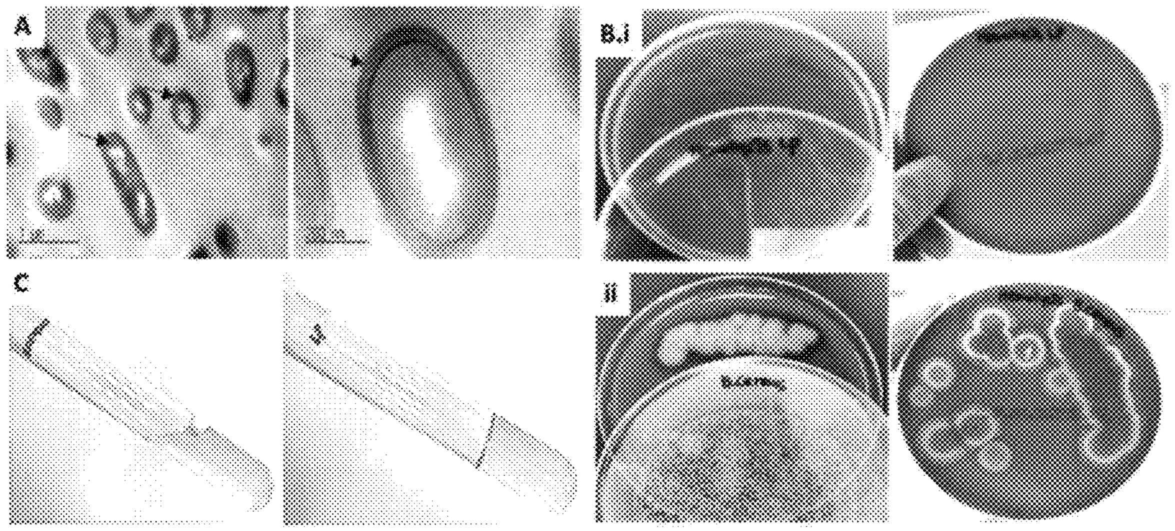
FIG. 2 shows the microbiological and biological characteristics of the *L. plantarum* IMB19 strain, in which A shows TEM images of the *L. plantarum* IMB19 strain, arrows indicating the capsular layer around the cell wall, B.i shows hemolytic activity of the *L. plantarum* IMB19 strain after 48 hours of culture in 5% sheep blood agar, B.ii shows a positive control being *Bacillus cereus* ATCC 27348, and C shows a gelatin hydrolysis test against the *L. plantarum* IMB19 strain, a positive control being *B. cereus* ATCC11778.

The colony morphology of *L. plantarum* is small, smooth, circular, and translucent. Cryosection TEM confirmed non-flagellated and rod-shaped microbial colonies of *L. plantarum* (A in FIG. 2). A thick capsular layer of individual bacteria was clearly observed. When cultured on sheep blood agar, neither transparent nor green areas formed, and thus the corresponding strain was confirmed to be non-hemolytic or γ-hemolytic, like other Lactobacilli (B in FIG. 2). The gelatinase activity was negative for up to 5 days against *Bacillus cereus* ATCC 11778 used as a positive control (C in FIG. 2). In addition, production of four biogenic amines of the strain was tested in a specialized medium (histamine, cadaverine, tyramine, and putrescine). It was found that *L. plantarum* IMB19 did not produce biogenic amines, unlike *E. coli* ATCC 25922 (Table 1).

TABLE 1

Biogenic amine production activity of *L. plantarum* IMB19 and *E. coli* ATCC 25922

| Strain | Histamine | Cadaverine | Tyramine | Putrescine |
|---|---|---|---|---|
| *L. plantarum* IMB19 | Negative | Negative | Negative | Negative |
| *E. coli* ATCC 25922 (Positive control) | Positive | Positive | Positive | Positive |

Antibiotic susceptibility test results, as shown in Table 2 below, were confirmed to exhibit susceptibility to most clinically relevant antibiotics, except for kanamycin, like most *Lactobacillus* species (Appl. Environ. Microbiol. 85, (2019)).

TABLE 2

Antibiotic resistance test of *L. plantarum* IMB19

| Strain | Minimum inhibitory concentration (mg/L) of antibiotics | | | | | | | | |
|---|---|---|---|---|---|---|---|---|---|
| | Amp | Ery | Gen | Tet | Str | Chl | Cli | Kan | Van |
| *L. plantarum* IMB19 | 0.5 | 0.5 | 8 | 2 | n.r | 8 | 2 | 128 | n.r |
| EFSA breakpoint | 2 | 1 | 16 | 32 | n.r | 8 | 4 | 64 | n.r |
| *L. plantarum* ATCC14917 (Q.C strain) | 0.25 | 0.5 | 16 | 16 | n.r | 8 | 1 | 256 | n.r |

*EFSA = European Food Safety Authority,
Amp = Ampicillin,
Ery = Erythromycin,
Gen = Gentamicin,
Tet = Tetracycline,
Str = Streptomycin,
Chl = Chloramphenicol,
Cli = Clindamycin,
Kan = Kanamycin,
Van = Vancomycin,
n.r = not required,
Q.C = Quality Control.

Example 5: Analysis of Genetic Properties of *L. plantarum* IMB19

Sequence similarity comparison based on 16S rRNA sequencing confirmed identification as *L. plantarum*. In addition, the same was distinguished from other genetically closely related species such as *L. pentosus* and *L. paraplantarum* through recA gene analysis using PCR (Appl. Environ. Microbiol. 67, 3450-3454 (2001)).

Analysis based on DNA isolation, Pac-Bio & Illumina Hi-seq sequencing, and bioinformatics was performed (Macrogen, Korea).

Figure 3:
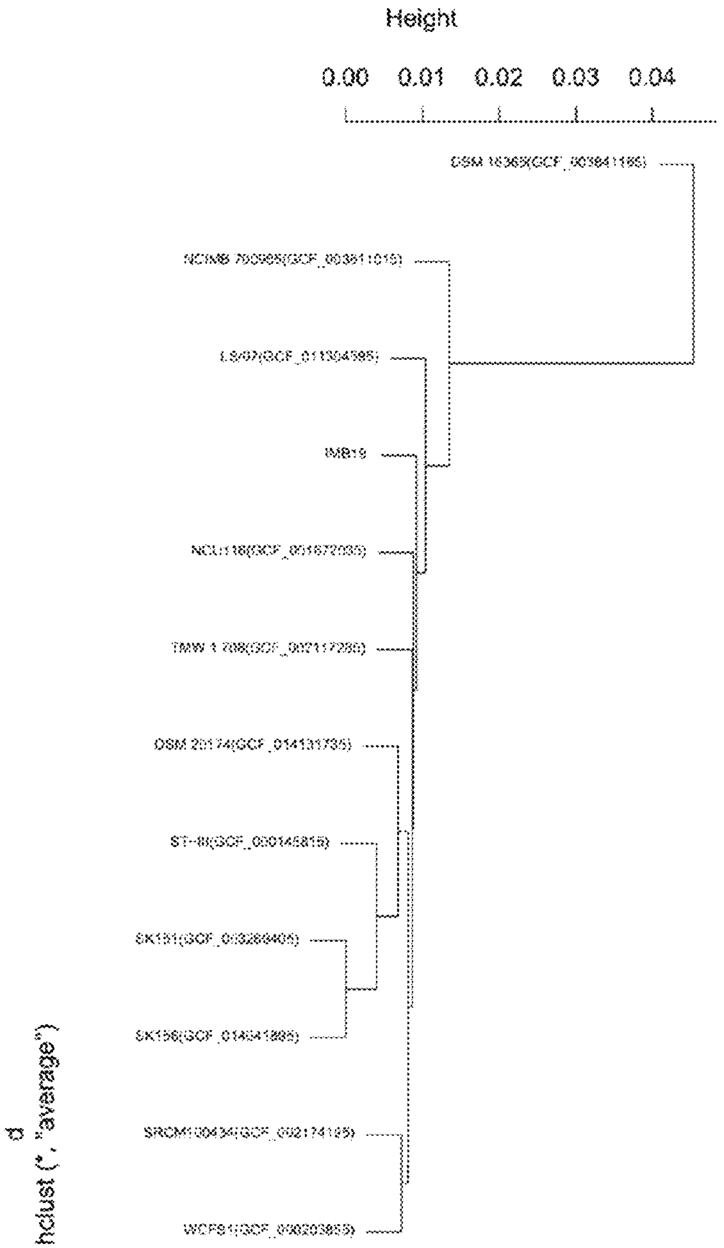
FIG. 3 shows the cluster dendrogram of *L. plantarum* IMB19, in which a phylogenetic tree was constructed based on the differences between *L. plantarum* strains, an average nucleotide index (ANI) being calculated using an OrthANI algorithm, and distance being directly proportional to the difference in genomes.

*L. plantarum* IMB19 was distinguished from other genetically closely related species by amplifying the recA gene and comparing the bands thereof using recA gene-derived primers. Since several *L. plantarum* strains are known to have similarities in the whole genome, phylogenetic analysis was performed based on the average nucleotide index (OrthoANI), and *L. plantarum* IMB19 was identified as a unique strain (FIG. 3). The presence of the putative virulent gene was confirmed using Virulence Finder 2.0 based on the homology of the virulent gene sequence to four known strains. No significant hits were found for virulent genes using a 90% nucleotide cut-off. As can be seen from ResFinder (J. Clin. Microbiol. 52, 1501-1510 (2014)), it was confirmed that there was no antibiotic resistance gene in the whole genome of *L. plantarum* IMB19.

As disclosed in Examples above, *L. plantarum* IMB19 was found to be a novel strain having characteristics different from those of the conventionally reported *L. plantarum* strain, and was deposited with accession number KCTC 14337BP at the Biological Resource Center of Korea Research Institute of Bioscience and Biotechnology on Oct. 21, 2020.

Figure 4:
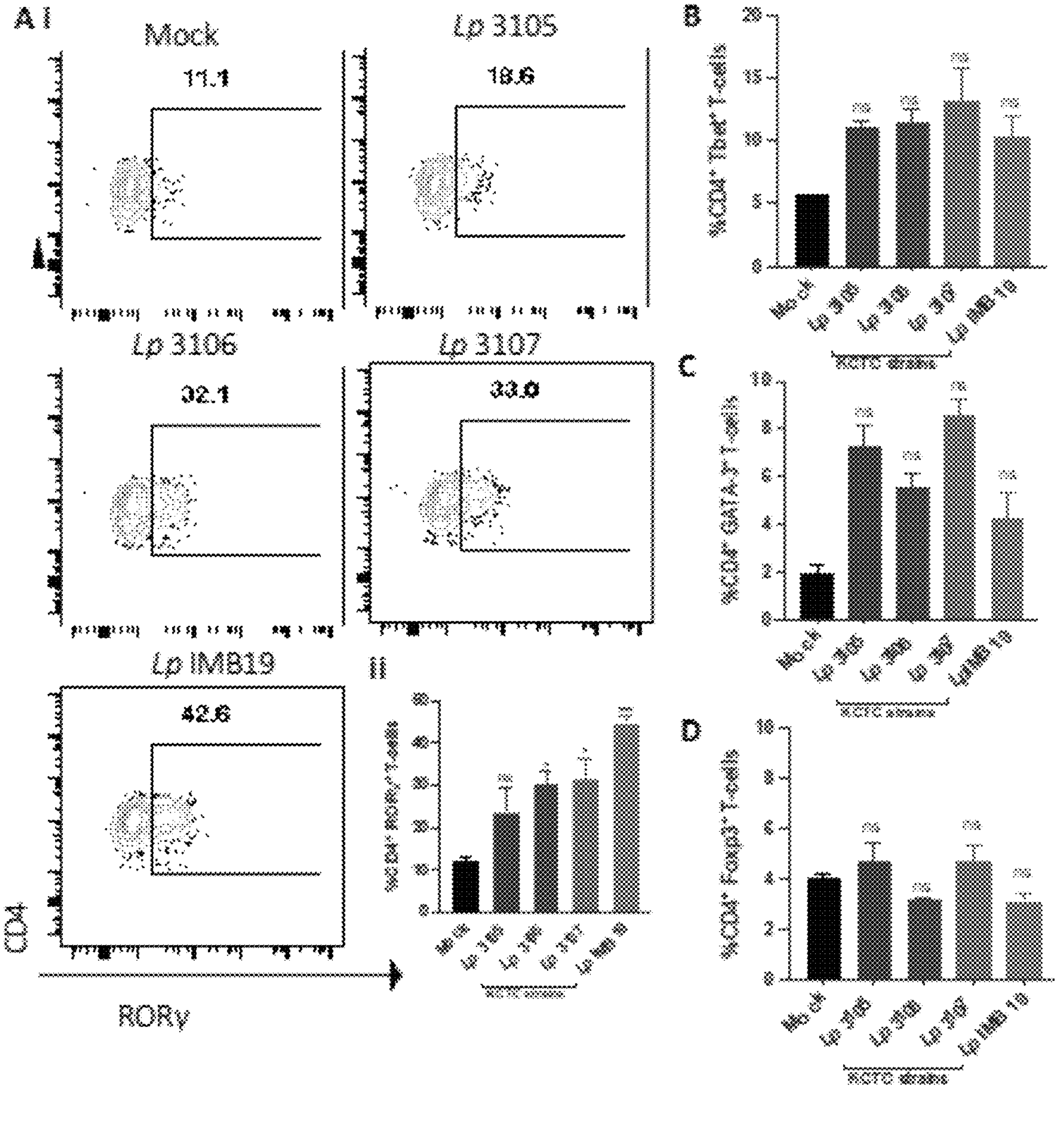
FIG. 4 shows results confirming production of Th 17 cells using various *Lactobacillus plantarum* strains, in which flow cytometry data showing the effects of *L. plantarum* IMB19, *L. plantarum* 3105, *L. plantarum* 3106, and *L. plantarum* 3107 on naive CD4+ T cells are represented, and dendritic cells primed with *L. plantarum* IMB19 were cultured with naive CD4+ T cells, anti-CD3 (10 ng/ml), and IL-2 (100 U/ml), wherein A i shows a FACS plot depicting production of Th17 cells, in which the cells were gated with live CD4+ RORγ+ T cells, A ii shows a bar graph depicting the average cell number for Th17 cells gated with live CD4+ RORγ+ T cells, B shows Th1 cells gated with live CD4+ T-bet+ T cells, C shows Th2 cells gated with live CD4+ GATA3+ T cells, and D shows Treg gated with live CD4+ Foxp3+ regulatory T cells, the data being presented as mean±SD, and statistical significance being calculated for Mock through one-way ANOVA, **p<0.01.

Example 6: Immunostimulatory Effect of *L. plantarum* IMB19 on Murine T Cells The beneficial effects on host immunity and health of several strains belonging to *L. plantarum* are well known (Biomed. Res. Int. 2018, U.S. Pat. No. 9,361,614 (2018)), and the direct effect of *L. plantarum* IMB19 of the present invention on murine immune cells was confirmed. The present inventors predicted that the uptake of bacterial antigens by antigen-presenting cells (APCs) made it possible to change the activation state, thereby priming other immune cells and consequently regulating the immune system. Therefore, a co-culture system containing both APCs and CD4+ T cells, which respectively represent the innate and adaptive immune systems, was designed. CD11c+ APCs were exposed to bacteria for 20 hours (APC:bacteria=1:100). These APCs were co-cultured with naive CD4+ T cells under suboptimal external stimulation without skewing the immune phenotype. In order to confirm the differentiation of T cells into Th1, Th2, Th17, or regulatory T cells (Treg), other transcription factors, for example Tbet, GATA3, RORγ, and Foxp3, were analyzed. Without special external influence, *L. plantarum* IMB19 significantly induced the production of CD4+ RORγ+ Th17 cells compared to the other three strains (A in FIG. 4). Significant production of other Th cell subtypes was uncertain, and appeared similar to other *L. plantarum* strains (B in FIG. 4).

Figure 5:
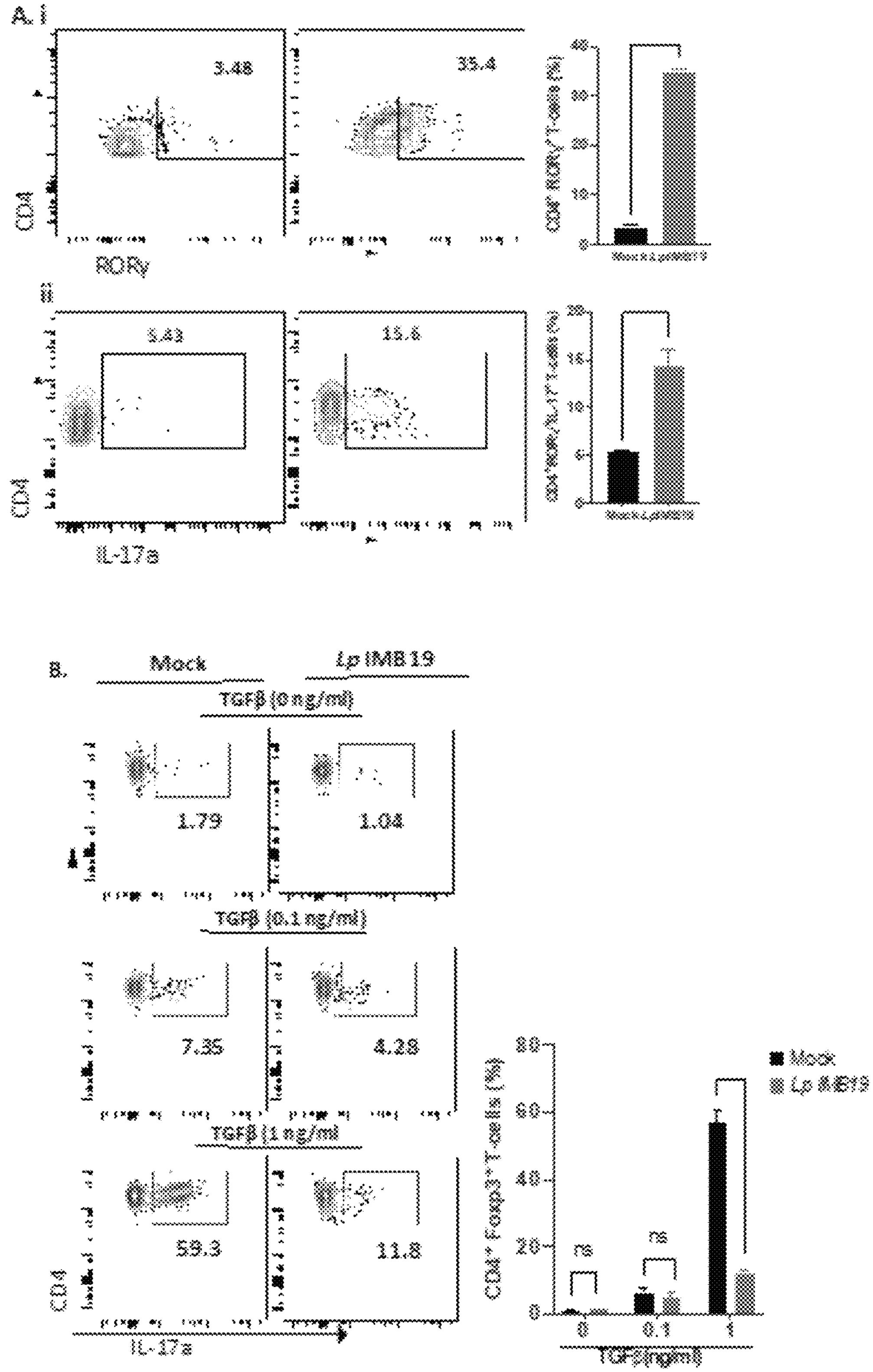
FIG. 5 shows the ability of *L. plantarum* IMB19 to inhibit Treg and induce Th17 cells, in which A I shows a representative FACS plot and bar graph showing the effect of *L. plantarum* IMB19 on the production of Th17 cells, in which dendritic cells primed with *L. plantarum* IMB19 were co-cultured with naive CD4+ T cells, anti-CD3 (0.1 μg/ml), TGF-β (0.5 ng/ml), IL-6 (2 ng/ml), IL1-β (2 ng/ml), IL-2 (100 U/ml), anti-IL4 (10 μg/ml), and anti-IFNγ (10 μg/ml), the cells being gated with live CD4+ RORγ+ T cells, A ii shows a representative FACS plot and bar graph showing the level of interleukin-17 in Th17 cells produced by *L. plantarum* IMB19, the cells being gated with live CD4+ RORγ+ IL-17+ T cells, and B shows a representative FACS plot and bar graph showing the inhibitory effect of *L. plantarum* IMB19 on Treg cell production in vitro, in which dendritic cells primed with *L. plantarum* IMB19 were co-cultured with naive CD4+ T cells, anti-CD3 (0.1 μg/ml), IL-2 (100 U/ml), and TGF-β at various concentrations, data being presented as mean±SEM, and statistical significance being analyzed through general one-way ANOVA, p<0.01, *p<0.001.

In order to verify the above results, production of Th17 cells by *L. plantarum* IMB19 was tested under conditions of minimal production of Th17 cells. *L. plantarum* IMB19 greatly increased the production of CD4+ RORγ+ Th17, which produced a significant amount of IL-17 (A in FIG. 5).

On the other hand, *L. plantarum* IMB19 did not induce a significant amount of Foxp3 under neutral conditions (B in FIG. 5), and thus, based on results confirming whether *L. plantarum* IMB19 was able to produce Tregs from naive CD4+ T cells at a sufficient concentration of TGF-β, production of Tregs was significantly inhibited at an increased concentration of TGF-β.

Example 7: Confirmation of Anti-Tumor Immune Response Promotion Effect of *L. plantarum* IMB19 In Vivo The *L. plantarum* IMB19 strain and various *Lactobacillus* strains (14 types) as controls were cultured with splenocytes to compare whether cytokine production was altered by immune cells. As a result, compared to other *Lactobacillus* strains, *L. plantarum* IMB19 showed significantly high IFN-γ levels and significantly low IL-10 levels (A in FIG. 6). For reference, another strain, *Lactobacillus murinus*, exhibited the highest ability to induce IL-10 and low ability to produce IFN-γ (A in FIG. 6).

Because CD8+ T cells are major anti-tumor effector cells, the ability of the two isolated strains to stimulate CD8+ T cells was confirmed. In co-culture of dendritic cells (DC) primed with bacteria and CD8+ T cells, IFN-γ levels were increased upon treatment with *L. plantarum* IMB19, and in particular, were remarkably increased compared to the case of treatment with *Lactobacillus murinus* (B in FIG. 6). Upon co-culture with splenic and mesenteric lymph node antigen-presenting cells, activation of CD8+ T cells was changed in a bacterial-concentration-dependent manner (A and B in FIG. 7).

*L. plantarum* IMB19 did not directly stimulate CD8+ T cells in the absence of dendritic cells. TCR-carrying CD8+ T cells against mouse melanoma-specific antigen Pmel-1 was similarly activated in the presence of antigen gp-100 (C in FIG. 7). In addition to DCs, macrophages are APCs known to play an important role in tumor growth and inhibition, so the effect of *L. plantarum* IMB19 on CD8+ T-cell stimulation through CD11b+ F4/80+ peritoneal macrophages was checked. Similar to dendritic cells, *L. plantarum* IMB19 greatly increased the proportion of IFN-γ+ CD8+ T cells during co-culture of macrophages and CD8+ T cells (C in FIG. 6).

Figure 8:
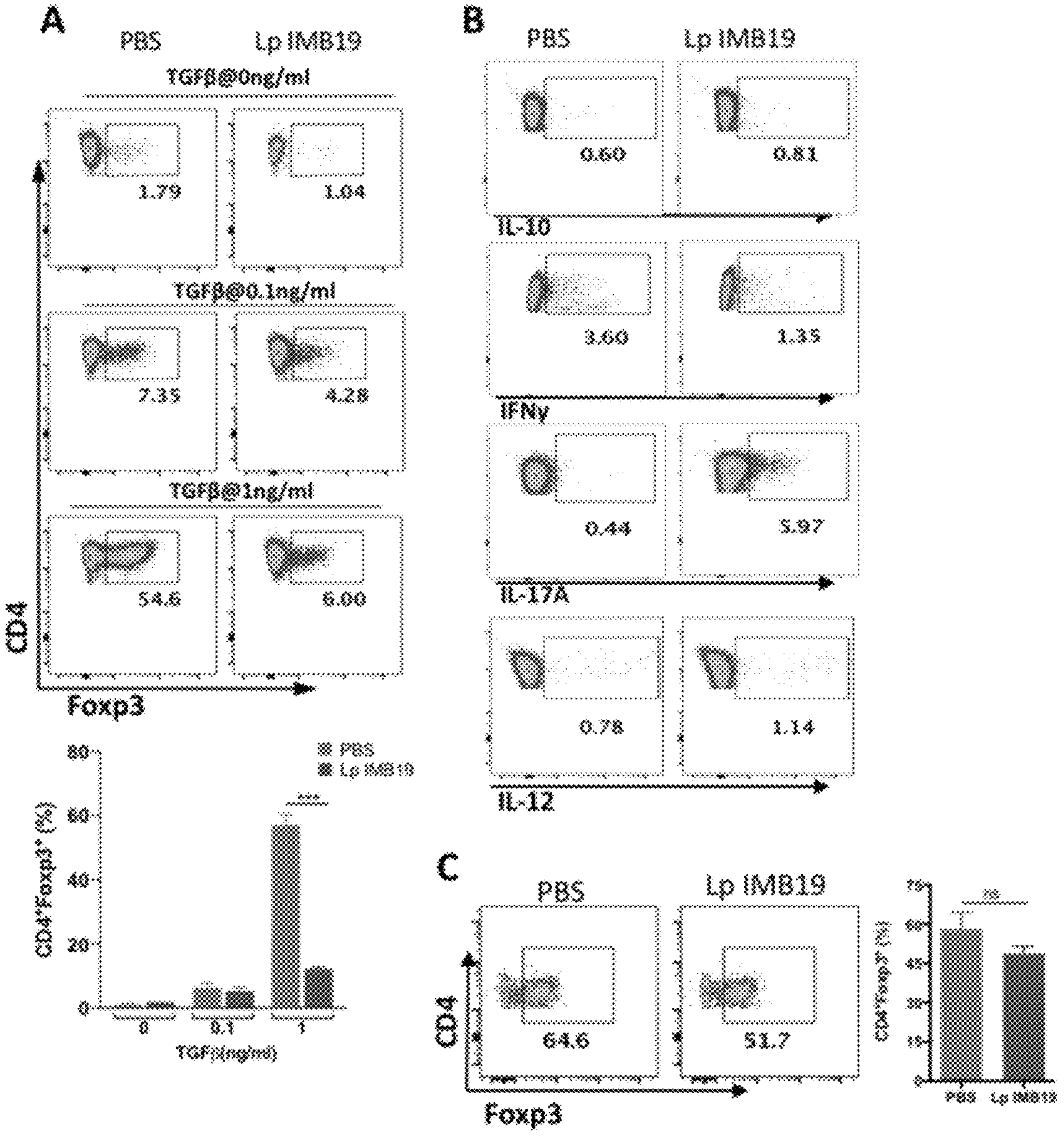
FIG. 8 shows inhibition of growth of regulatory T cells through interleukin-6 production of *L. plantarum* IMB19, in which A shows the results of quantification of Foxp3+ CD4+ T cells in co-cultures of splenic CD11c+ dendritic cells primed with *L. plantarum* IMB19 at different TGF-β concentrations and naive CD4+ T cells, B shows the results of quantification of cytokines in co-cultures of splenic CD11c+ dendritic cells primed with *L. plantarum* IMB19 at a TGF-β concentration of 2 ng/ml and naive CD4+ T cells, the cells being gated with total CD4+ T cells, and C showing the results of quantification of Foxp3+ CD4+ T cells in IL-6−/− splenic DCs and co-cultures of splenic CD11c+ dendritic cells primed with *L. plantarum* IMB19 at a TGFβ concentration of 0.01 ng/ml and naive CD4+ T cells, with the data being presented as mean±SEM and being analyzed through typical one-way ANOVA with Tukey's multiple comparisons, ***p<0.001, ns: not significant.

CD4+ Foxp3+ regulatory T cells (Tregs) accumulate in tumors and increase tumor progression by inhibiting effector functions of CD8+ T cells and other immune cells. In addition, several bacteria that promote Treg production have been reported (Nature 453, 620-625 (2008); Sci. Immunol. 3, (2018)). Therefore, the present inventors confirmed whether *L. plantarum* IMB19 affects induction of Treg during co-culture of CD11c+ DC and CD4+ T cells. *L. plantarum* IMB19 remarkably inhibited the production of Treg in the presence of TGF-β under strong Treg skewing culture conditions (D in FIG. 6). This effect persisted even at lower levels of TGF-β, and no Treg production was observed in any of the conditions tested (A in FIG. 8). On the other hand, the level of interleukin-17A (IL-17A) was increased (B in FIG. 8), indicating the production of T-helper-17 cells (Th17). Interleukin-6 (IL-6) is essential for Th17 production, and inhibits Treg production in the presence of TGF-β (Eur. J. Immunol. 40, 1830-1835 (2010)). Accordingly, IL-6-deficient DCs produced Tregs during co-culture with CD4+ T cells. Therefore, IL-6 production by DCs primed with *L. plantarum* IMB19 suppressed Treg production under Treg skewing culture conditions.

Figure 6:
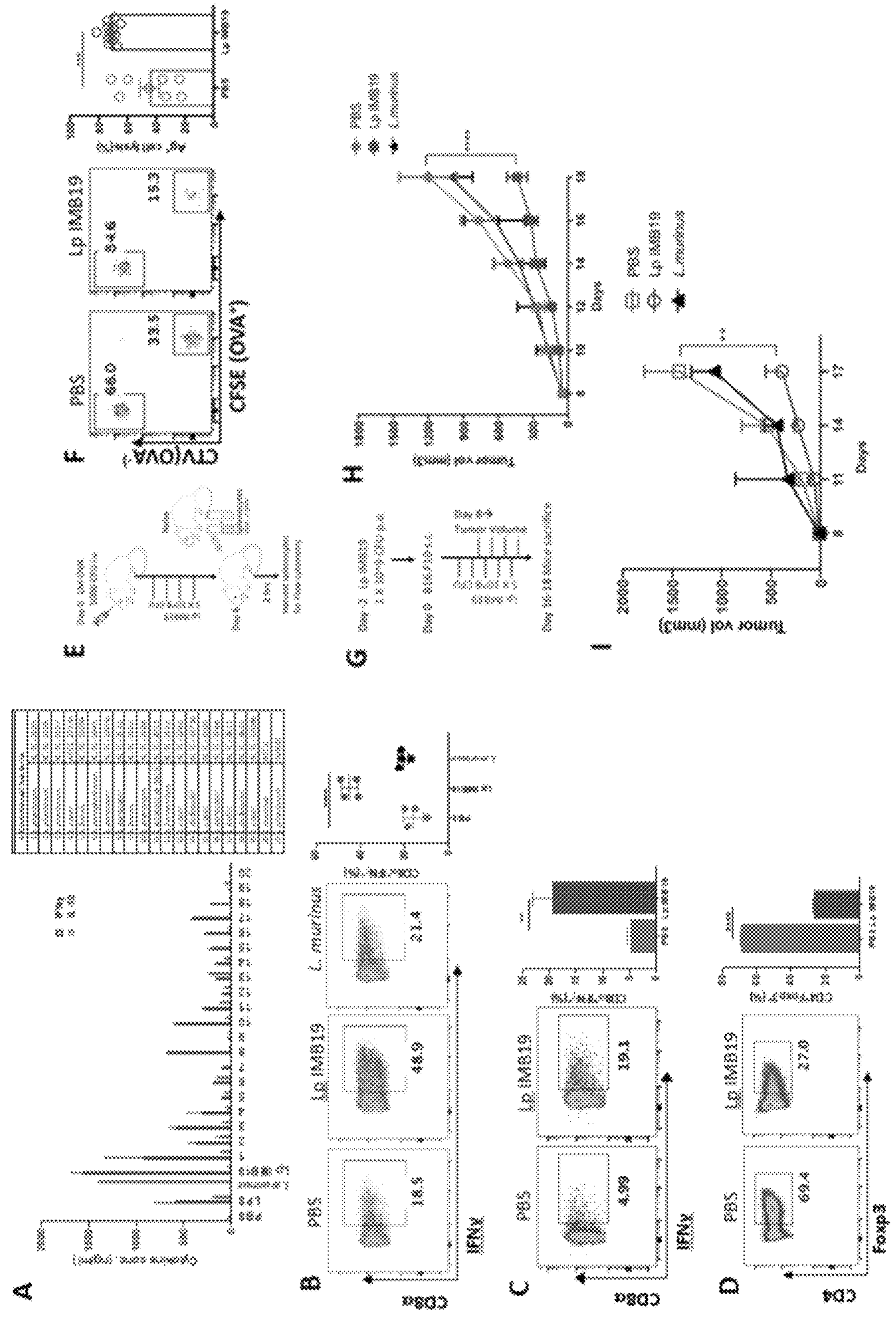
FIG. 6 shows an anti-tumor immune response achieved through CD8+ T cell activation enhanced by *L. plantarum* IMB19, in which A shows the results of analysis of cytokine level in the splenocyte-bacteria co-culture supernatant through ELISA, B shows the results of quantification of IFNγ+ CD8+ T cells from co-cultures of splenic CD11c+ dendritic cells primed with *L. plantarum* IMB19 or *L. murinus* and naive CD8+ T cells, C shows the results of quantification of IFNγ+ CD8+ T cells from co-cultures of CD11b+F4/80+ peritoneal macrophages primed with *L. plantarum* IMB19 and naive CD8+ T cells, D shows the results of quantification of Foxp3+ CD4+ T cells from co-cultures of splenic CD11c+ dendritic cells primed with *L. plantarum* IMB19, naive CD4+ T cells, and 2 ng/ml of TGF-β, the data being mean±SEM values and B being analyzed through general one-way ANOVA with Tukey's multiple comparisons, p<0.01, **p<0.0001, E schematically shows an in-vivo OVA expression *Listeria monocytogenes* (LM-OVA) cytotoxicity assay, F shows *L. plantarum* IMB19-mediated CD8+ T cell-specific cytotoxicity against OVA+ splenocytes in mice infected with LM-OVA, G schematically shows an in-vivo B16.F10 melanoma mouse model, H shows B16.F10 melanoma growth kinetics in C57/BI6 germ-free mice treated or not treated with *L. plantarum* IMB19 or *L. murinus*, and I shows B16.F10 melanoma growth kinetics in C57/BI6 SPF mice treated or not treated with *L. plantarum* IMB19 or *L. murinus*, the data being mean±SEM values, with F showing the results of a non-parametric two-tailed t-test, and H and I showing results of two-way ANOVA with Dunnett's multiple comparisons, P<0.01, *P<0.001, ****P<0.0001.
Figure 7:
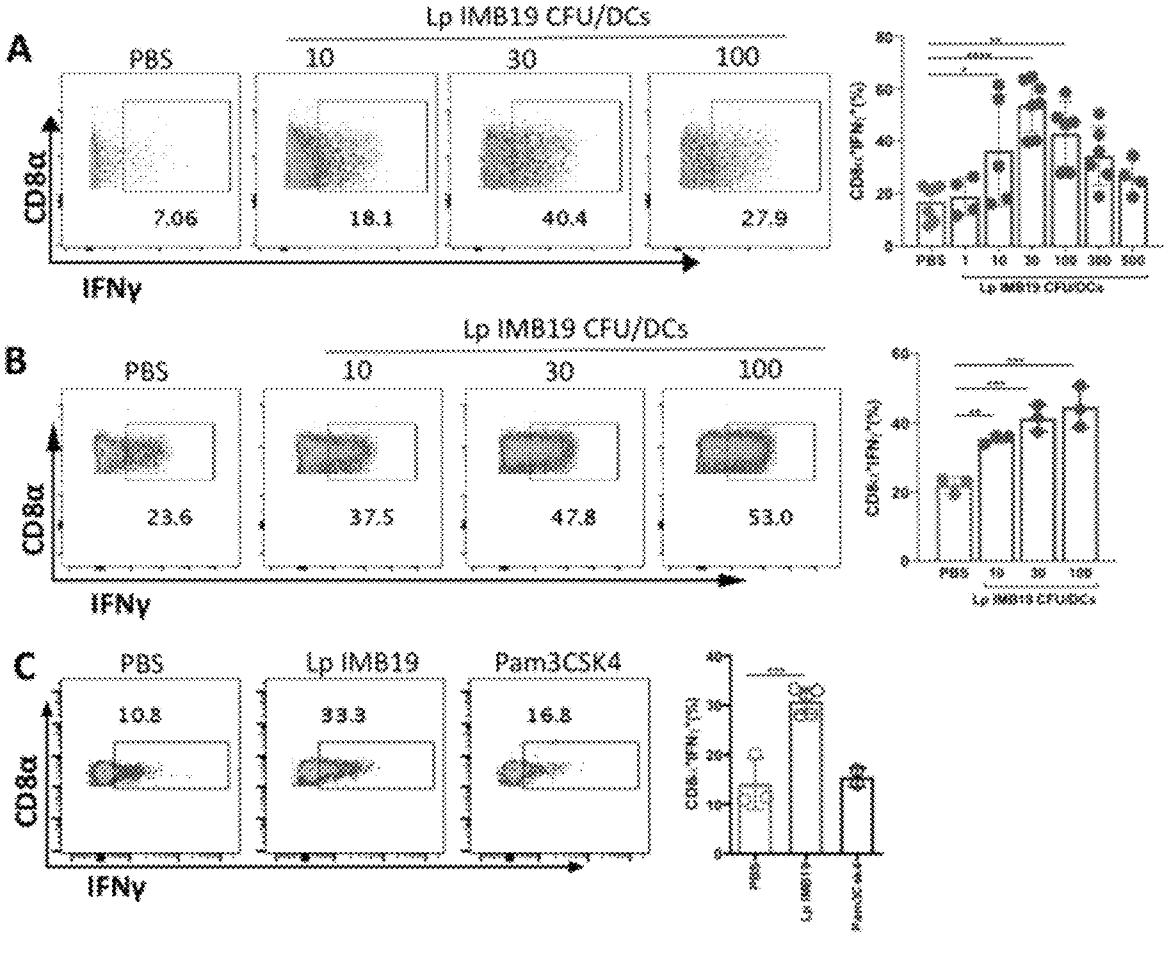
FIG. 7 shows the dose-dependent effect of *L. plantarum* IMB19 on CD8+ T cells, in which A and B show the results of quantification of IFNγ+ CD8+ T cells in co-cultures of splenic (A) or mLN (B) CD11c+ dendritic cells primed with *L. plantarum* IMB19 at different ratios and naive CD8+ T cells, with C showing the results of quantification of IFNγ+ CD8+ T cells in co-cultures of splenic CD11c+ dendritic cells primed with *L. plantarum* IMB19 at different ratios and naive pmel TCR-inoculated CD8+ T cells in the presence of 100 ng/ml of gp-100, data being presented as mean±SEM and being analyzed through typical one-way ANOVA with Tukey's multiple comparisons, p<0.01, *p<0.001, ****p<0.0001.
Figure 9:
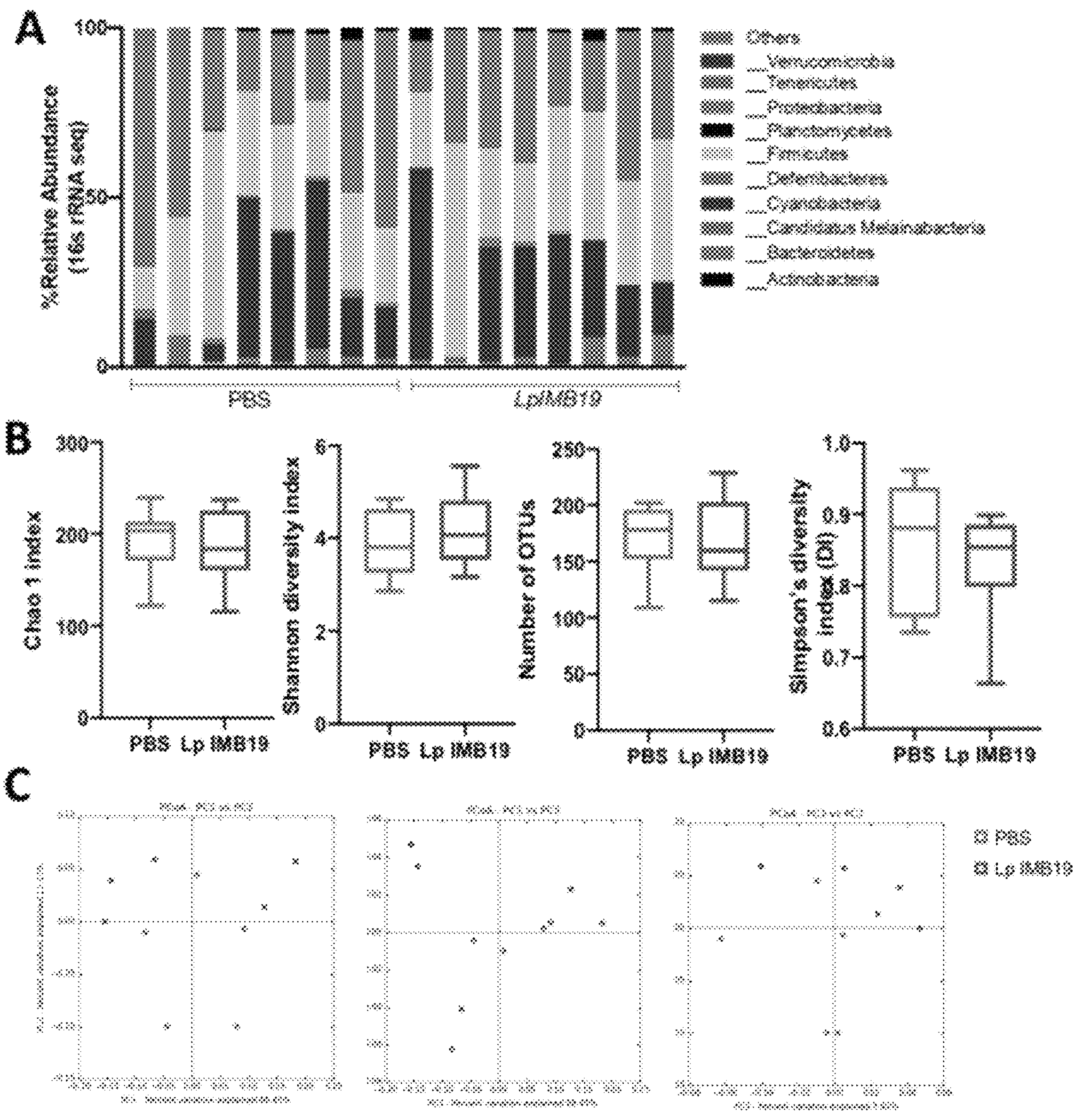
FIG. 9 shows the effect of *L. plantarum* IMB19 on tumor immunity without change in microbial diversity, in which A shows the results of phylogenetic analysis of phyla (%) in fecal samples of tumor-bearing mice fed with *L. plantarum* IMB19 in H in FIG. 6, and B and C show the results of alpha diversity analysis and principal coordinate analysis of bacterial β-diversity in fecal samples of tumor-bearing mice fed with *L. plantarum* IMB19 in H of FIG. 6, the data indicating values from two independent experiments.

In order to test whether CD8+ T cells activated by *L. plantarum* IMB19 are functionally cytotoxic, cytotoxicity was tested using an acute *Listeria monocytogenes* infection model expressing the OVA antigen (LM-OVA) (E in FIG. 6). LM-OVA-infected mice fed with *L. plantarum* IMB19 showed a significant increase in lysis of target cells loaded with OVA-pulsed CFSE in vivo (F in FIG. 6). In addition, the effect of *L. plantarum* IMB19 on B16.F10 melanoma subcutaneously inoculated to both SPF (specific pathogen-free) and GF (germ-free) mice was evaluated (G in FIG. 6). *L. plantarum* IMB19 showed significant inhibition of melanoma growth in both SPF and GF mice compared to *L. murinus* (H and I in FIG. 6). In order to evaluate whether *L. plantarum* IMB19 induces any dysbiosis resulting in anti-tumor effects, 16s ribosomal RNA sequencing was performed on fetal samples from tumor-bearing animals fed with *L. plantarum* IMB19. However, there were no significant changes in microbial diversity in the feces of *L. plantarum* IMB19-fed mice compared to the PBS control (A to C in FIG. 9). This means that *L. plantarum* IMB19-mediated regulation of anti-tumor immunity corresponds to *L. plantarum* IMB19-specific effects and is not a result of dysbiosis. Consequently, the data in this Example indicate that *L. plantarum* IMB19 is a positive regulator of cytotoxic T cell-mediated anti-tumor immune responses in vivo.

Example 8: Analysis of Chemical Properties of Crude Polysaccharide Fraction Derived from *L. plantarum* IMB19

Figure 10:
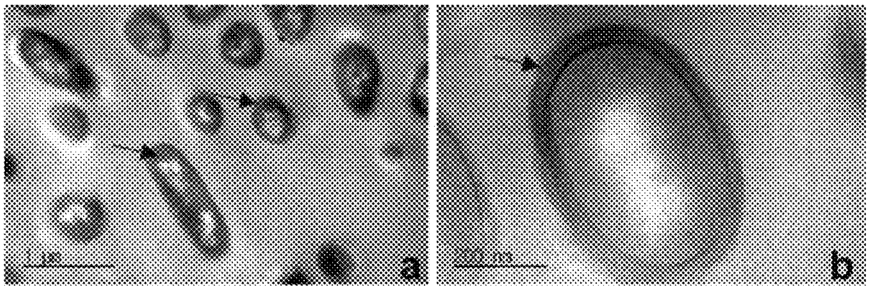
FIG. 10 shows transmission electron microscopy (TEM) images of *L. plantarum* IMB19, in which a shows an *L. plantarum* IMB19 bacterial community, the arrows indicating individual bacteria, and in which b shows *L. plantarum* IMB19, the arrow indicating a thick capsular layer around the cell wall.
Figure 11:
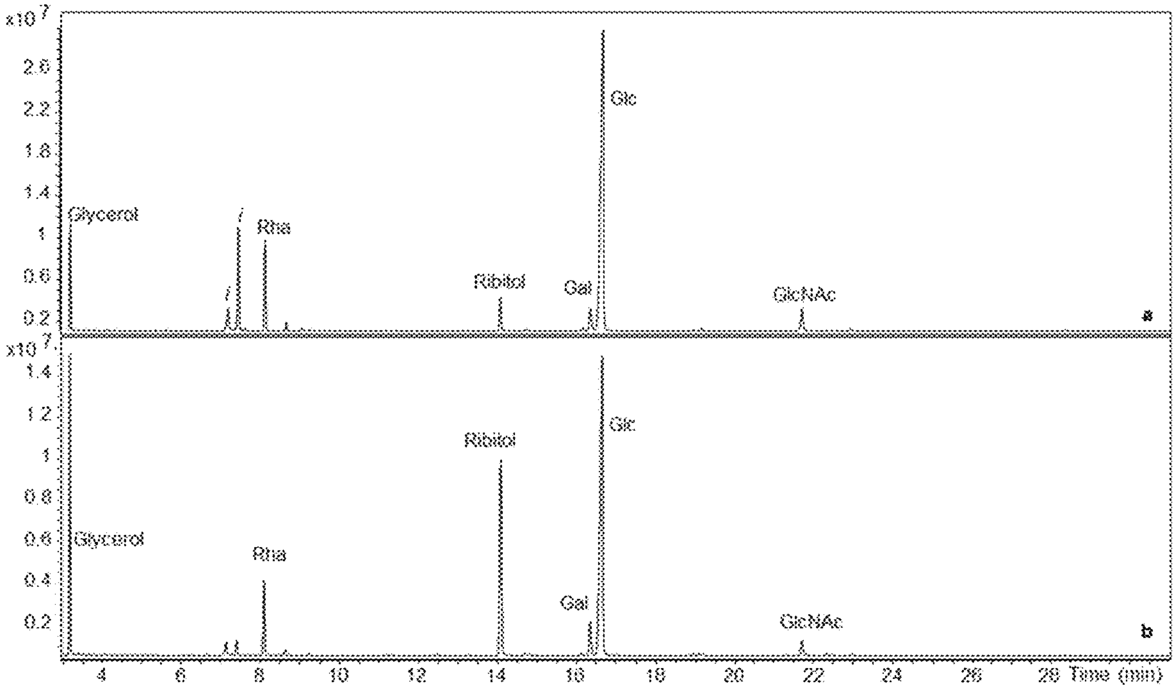
FIG. 11 shows the GC-MS profile of CPS-derived acetylated methylglycoside extracted from *L. plantarum* IMB19 in which the sample was dephosphorylated without HF treatment (a) or through HF treatment (b), "i" denoting impurities.
Figure 12:
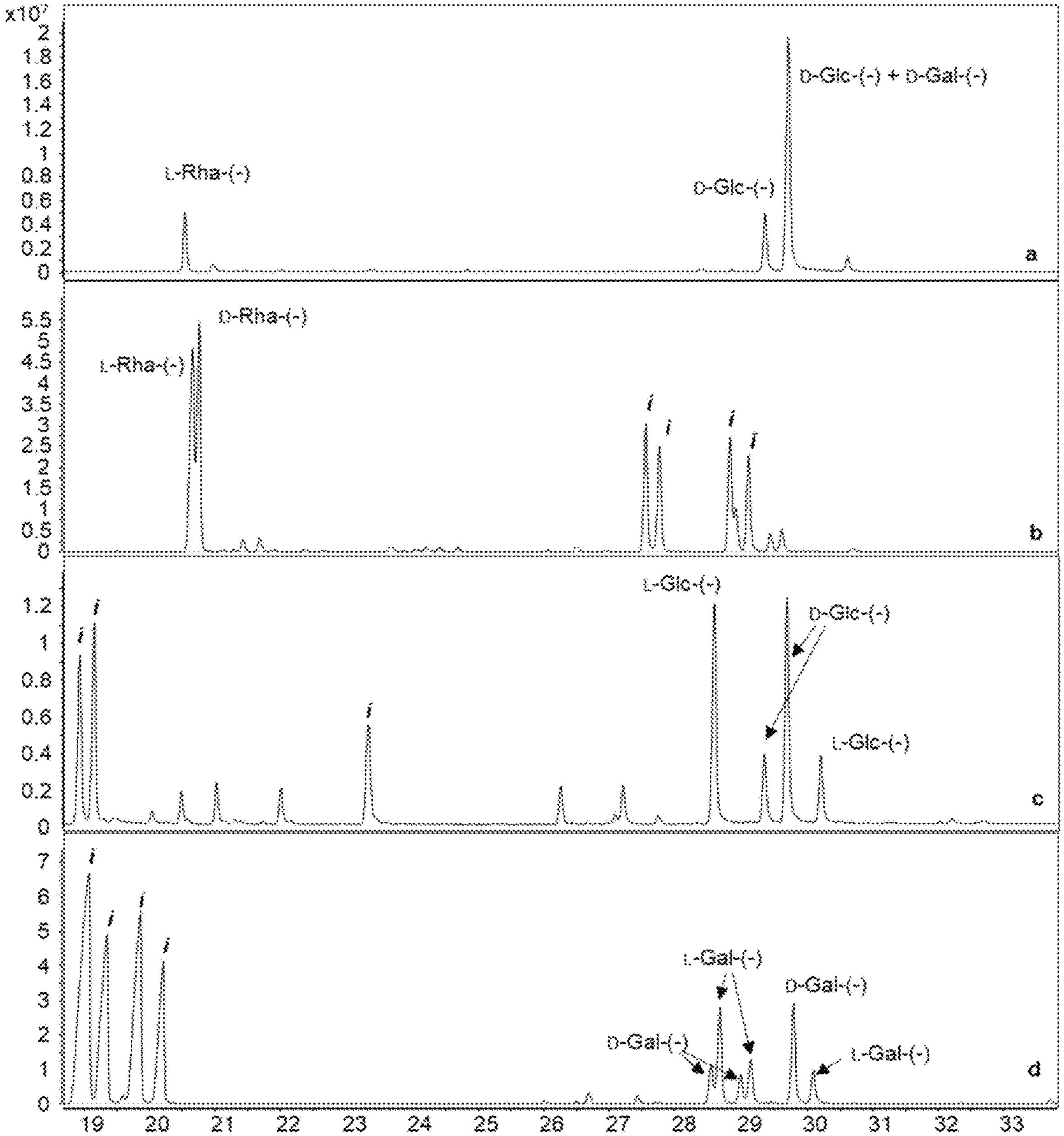
FIG. 12 shows GC-MS profiles of acetylated 2-(−)-octyl derivatives (a), rhamnose (b), glucose (c), and galactose acetylated 2-(−)-octyl glycoside standard (d) of CPS extracted from *L. plantarum* IMB19, "i" denoting impurities.

Based on the results of analysis using transmission electron microscopy (TEM), it was confirmed that the cells of *L. plantarum* IMB19 were surrounded by a layer of capsular material containing a carbohydrate composition composed of rhamnose, galactose, glucose, and glucosamine, along with small amounts of glycerol and ribitol (FIG. 10, and a in FIG. 11). The two polyols are typically associated with the presence of teichoic acids, which are interconnected via phosphodiester linkage (Tomita, Tanaka, & Okada, 2017). In general, detection of these polyols is very difficult, because methanolysis is incapable of completely cleaving a phosphodiester linkage. Therefore, GC-MS analysis was repeated by dephosphorylating the sample with aqueous HF before methanolysis and acetylation, and the presence of teichoic acid was confirmed based on the increase in the amounts of both polyols. For monosaccharides, rhamnose has an absolute L configuration, and glucose and galactose have a D configuration (FIG. 12). On the other hand, for glucosamine, the D configuration was assumed based on the exclusive presence of a stereoisomer.

Example 9: Purification of Crude Polysaccharide

Chemical analysis of the carbohydrate component suggested that CPS could be a mixture of polymers. Accordingly, six fractions obtained by purifying CPS using ion exchange chromatography were denoted as CPS-X, "X" indicating the concentration of the eluent that was used. The yields obtained through purification were as follows: CPS-10 11%, CPS-100 13%, CPS-200 9.0%, CPS-400 51%, CPS-700 7.0%, and CPS-1000 7.9%. Each fraction was compared with the spectral profile of the original mixture (CPS) using $^{1}$H NMR analysis (FIG. 13).

Figure 13:
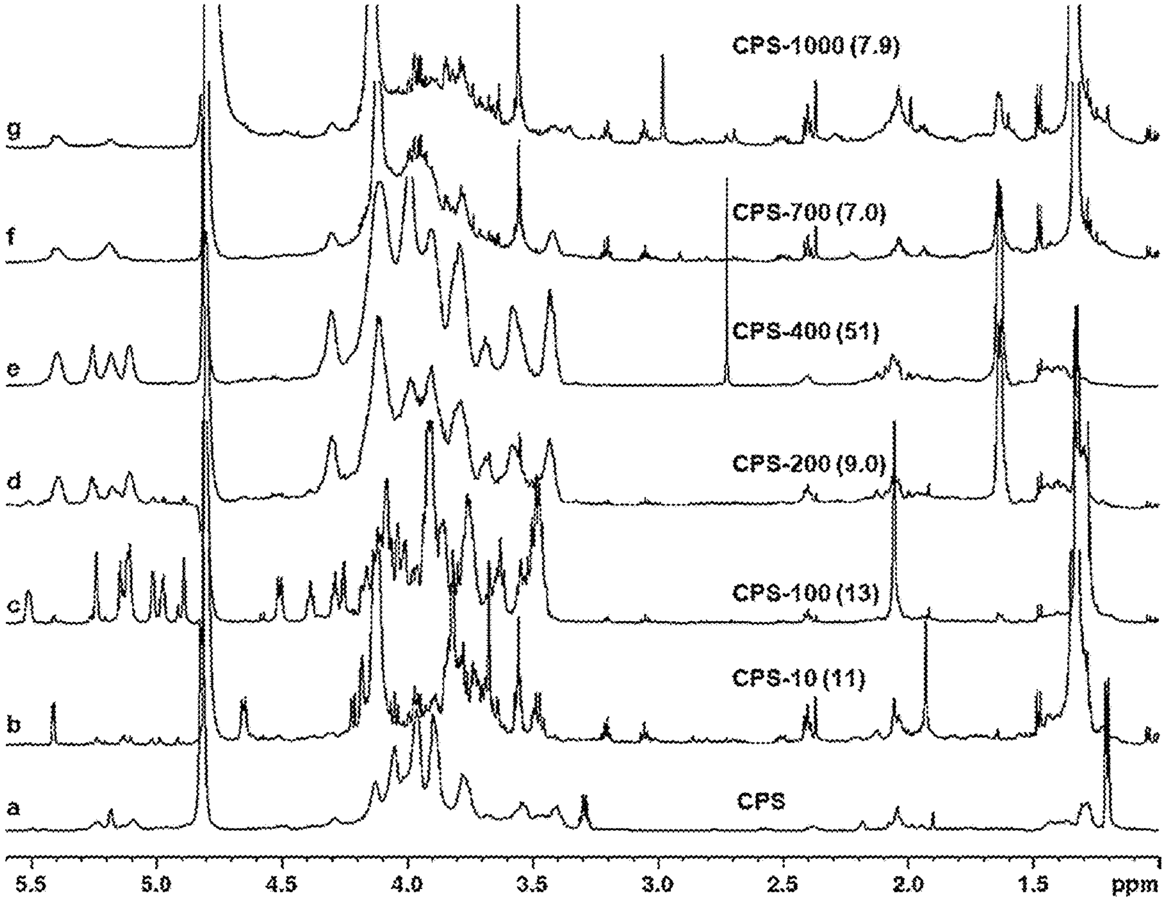
FIG. 13 shows proton spectra of fractions obtained by purifying crude CPS through ion exchange chromatography (600 MHz, 298K): CPS (a), CPS-10 (b), CPS-100 (c), CPS-200 (d), CPS-400 (e), CPS-700 (f), and CPS7-1000 (g), with the numbers in parentheses denoting the yield (mg/mg) of each fraction in comparison with 28 mg of crude CPS.

Specifically, individual fractions were as follows (FIG. 13).

CPS-10 (b in FIG. 13): CPS-10 showed a rather heterogeneous spectrum. The anomeric region of CPS-10 includes two main intense signals of 4.2 and 1.3 ppm, associated with materials different from carbohydrates.

Figure 14:
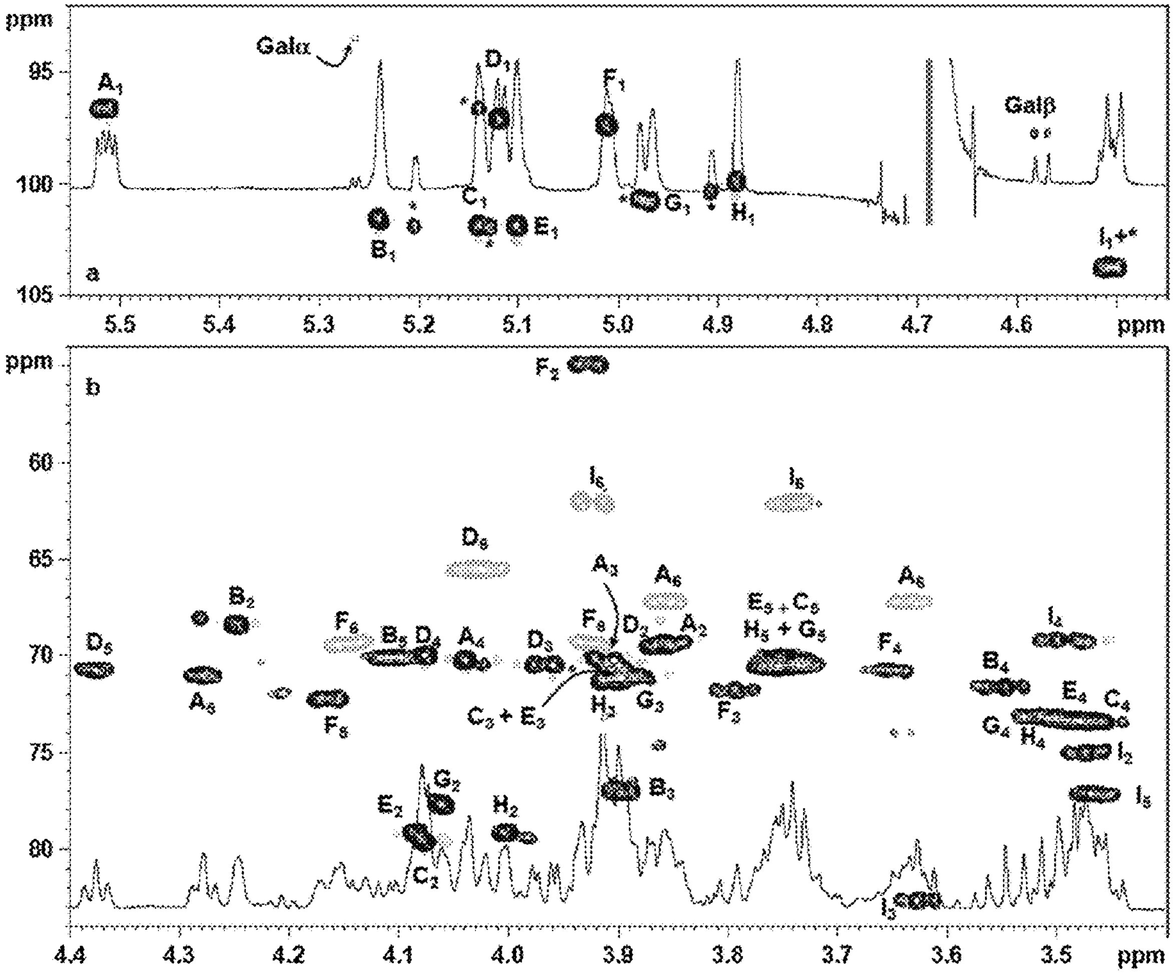
FIG. 14 shows the expansion of the recorded HSQC spectrum for the capsular polysaccharide of *L. plantarum* IMB19 (600 MHz, 310K): (a) expansion of the anomeric region, (b) expansion of the carbinolic region, the grey density corresponding to the "$CH_2$" carbon, and "*" indicating the minor anomeric signals of the repeating unit sugar attached to galactose in reduced forms (Galα and Galβ), with reference to FIG. 20 for the structure of the repeating unit and to Table 3 for labels.

CPS-100 (c in FIG. 13): The anomeric region (5.6-4.5 ppm) of CPS-100 includes 9 major signals having doublets at 5.5 ppm, indicating residues in an α configuration ($^{3}J_{H1,H2}$=3.4 Hz) and phosphorylation ($^{3}J_{H1,P}$=7.0 Hz) (FIG. 14). Also, an acetyl group (methyl group at 2.06 ppm) and an intense signal including several methyl groups of deoxy residues (1.3 ppm), respectively consistent with the presence of N-acetylglucosamine and rhamnose units, were observed.

CPS-200 (d in FIG. 13): CPS-200 appeared as a mixture with CPS-100 and CPS-400, showing four rather broad signals in the anomeric region, and an intense methyl signal at 1.6 ppm (a value inconsistent with methyl in rhamnose) and in a congested carbinolic region (4.4-3.2 ppm).

Figure 15:
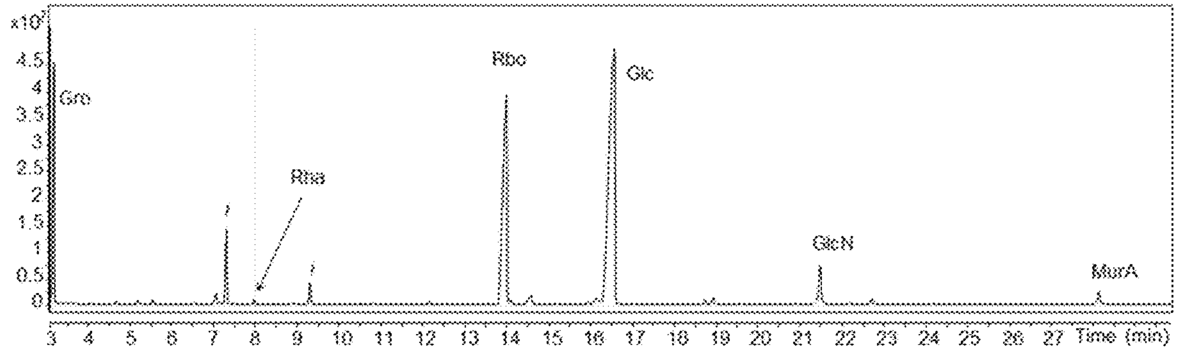
FIG. 15 shows a GC-MS profile of the acetylated methylglycoside of CPS-400 extracted from *L. plantarum* IMB19 after dephosphorylation of the sample through HF treatment, "i" denoting impurities, and MurA denoting muramic acid, which is a component of bacterial peptidoglycan.

Integration showed that the ratio of anomeric protons to carbinolic protons was 1.0:12, and the generally expected ratio was 1:6 or less, indicating that CPS-400 does not have the typical structure of polysaccharide and the increase in the ratio is due to the presence of ribitol and glycerol units, as confirmed through chemical analysis (FIG. 15). Also, glucose was the most abundant monosaccharide, followed by two monosaccharides in small amounts, namely glucosamine (GlcN) and muramic acid (MurA), as the characteristics of peptidoglycan.

This observation suggests that CPS-400 is teichoic acid (TA).

CPS-700 and CPS-1000 (f and g in FIG. 13): The anomeric region included only some signals found in CPS-400, and the ratio of anomeric protons to carbinolic protons in both fractions was atypical. Signals of non-carbohydrate materials were also further observed.

CPS-10, CPS-700, and CPS-1000 were not abundant in CPS, so only small amounts thereof were obtained.

Example 10: NMR Analysis of CPS-100

The structure of the capsular polysaccharide was determined by analyzing the complete set of $^{1}$H-$^{1}$H homonuclear (COSY, TOCSY, NOESY) and $^{1}$H-$^{13}$C heteronuclear (HSQC, HMBC, HSQC-TOCSY) 2D NMR spectra recorded at 310K (Table 3).

TABLE 3

Proton ($^{1}$H, static) and carbon ($^{13}$C, italic) NMR chemical shifts of repeating units of CPS-100

| | 1 | 2 | 3 | 4 | 5 | 6 |
|---|---|---|---|---|---|---|
| A | 5.51 | 3.85 | 3.91 | 4.04 | 4.28 | 3.86;3.63 |
| 6-α-Gal-1 | 96.6 | 69.3 | 70.2 | 70.2 | 71.1 | 67.1 |
| B | 5.24 | 4.25 | 3.90 | 3.55 | 4.11 | 1.29 |
| 3-α-Rha | 101.6 | 68.4 | 77.1 | 71.7 | 70.2 | 18.1 |
| c | 5.14 | 4.08 | 3.90 | 3.46 | 3.73 | 1.29 |
| 2-α-Rha | 101.9 | 79.6 | ca71* | 73.4 | ca 70.5** | 18.1 |
| D | 5.12 | 3.86 | 3.97 | 4.08 | 4.38 | 4.04;4.02 |
| 6P-α-Gal | 97.1 | 69.5 | 70.4 | 70.0 | 70.8 | 65.6 |
| E | 5.10 | 4.08 | 3.90 | 3.48 | 3.76 | 1.29 |
| 2-α-Rha | 101.9 | 79.2 | ca71* | 73.4 | ca 70.5 | 18.1 |
| F | 5.01 | 3.93 | 3.79 | 3.65 | 4.17 | 4.14;3.92 |
| 6-α-GlcNAc | 97.4 | 54.9 | 71.8 | 70.7 | 72.3 | 69.5 |
| G | 4.97 | 4.06 | 3.89 | 3.52 | 3.76 | 1.29 |
| 2-α-Rha | 100.8 | 77.8 | 71.1 | 73.2 | ca 70.5** | 18.1 |
| H | 4.88 | 4.00 | 3.91 | 3.48 | 3.75 | 1.31 |
| 2-α-Rha | 99.9 | 79.2 | 71.4 | 73.3 | ca 70.5** | 181 |
| I | 4.50 | 3.47 | 3.63 | 3.50 | 3.46 | 3.92;3.74 |
| 3-β-Glc | 103.7 | 75.0 | 82.8 | 69.1 | 77.2 | 62.1 |

*C-3 of C and E overlapping, and exact chemical shift thereof not being determined with certainty

C-5 of C, E, G and H overlapping, and exact chemical shift thereof not being determined with certainty The temperature elevation from 297K (c in FIG. 13) to 310K (FIG. 14**) reduced the overlap between three anomeric signals at about 5.15 ppm and simplified the NMR properties of the relevant residues.

Figure 16:
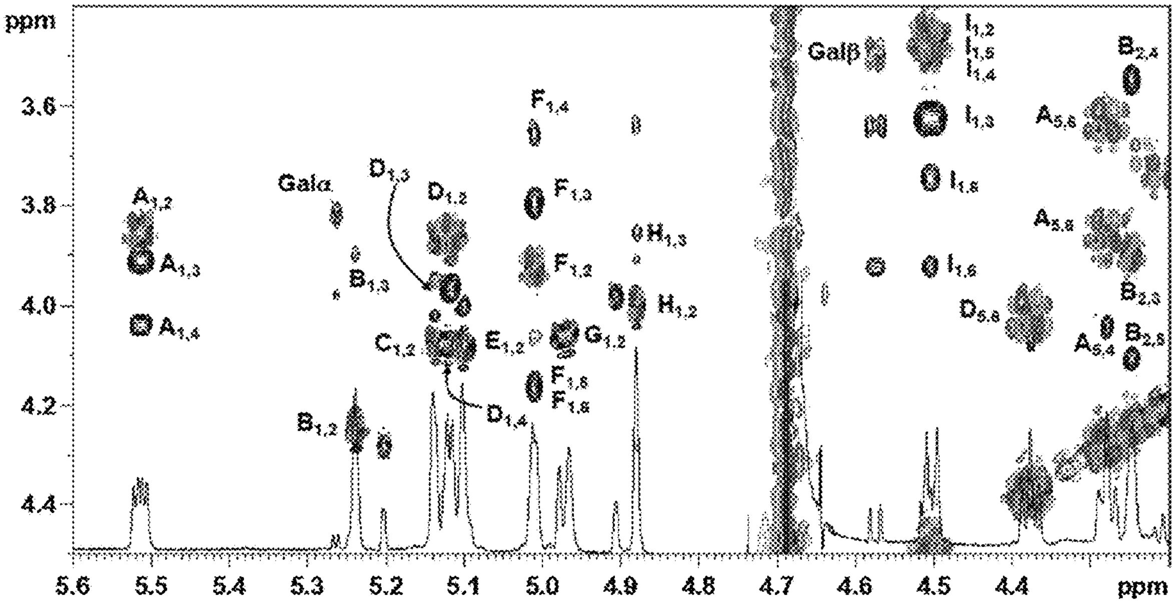
FIG. 16 shows the expansion of TOCSU (black) and COZY (cyan/red) spectra recorded for the capsular polysaccharide, CPS-100, of *L. plantarum* IMB19 (600 MHz, 310K), with reference to FIG. 20 for the structure of the repeating unit and to Table 3 for labels.
Figure 17:
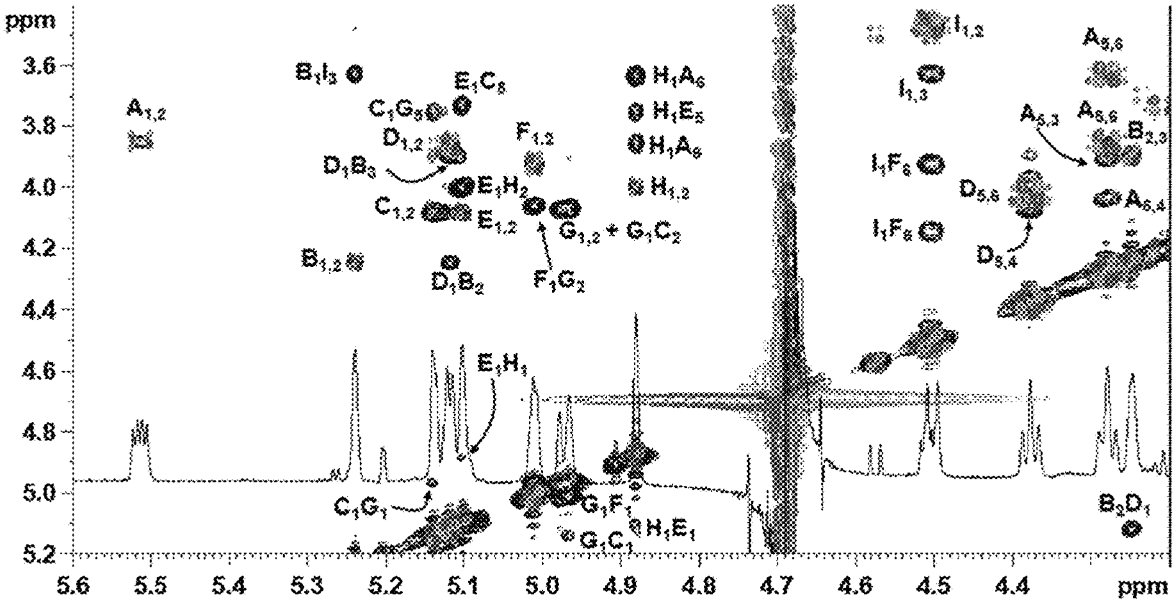
FIG. 17 shows the expansion of NOESY (black) and COZY (cyan/red) spectra recorded for the capsular polysaccharide, CPS-100, of *L. plantarum* IMB19 (600 MHz, 310K), with reference to FIG. 20 for the structure of the repeating unit and to Table 3 for labels.

The HSQC spectrum (FIG. 14) showed 9 major anomeric densities at $^{1}$H 5.6-4.5 indicated by the uppercase letters A-I in a in FIG. 14 and in Table 3, and the corresponding protons were all present in similar proportions. The NMR analysis started at H-1 (5.51 ppm) of A, which shows three correlations in the TOCSY spectrum, in common with 3.85 ppm of the COSY spectrum (FIG. 16). Thus, this density was assigned to H-2, and H-3 (3.91 ppm) and H-4 (4.04 ppm) were also assigned in a similar approach. Since there was no additional correlation with H-1, A was identified as a galactose unit. H-5 was identified in the NOESY spectrum due to the strong H-4/H-5 correlation (FIG. 17), and two H-6 were identified through the corresponding COZY correlation (FIGS. 16 and 17).

The HSQC and HSQC-TOCSY spectra (a in FIG. 18) defined all carbon chemical shifts of A (Table 3), which is the α-galactose unit linked to O-6, based on the high chemical shift of C-6 (67.1 ppm). Since the correlation of the TOCSY spectrum originating from H-1 (5.12 ppm) of D had the same pattern as A, D was galactose, a configured based on the $^{3}J_{H1,H2}$ (3.9 Hz) value, and chemical shift of H-6s/C-6 (4.04-4.02/65.6 ppm) implies phosphorylation at this position, consistent with data from the literature (Sechenkova et al., 2004). Therefore, D was 6P-α-Gal, and was determined not to be branched anymore based on the high field values of all other carbon chemical shifts.

For B, H-1 (5.24 ppm) showed the two strongest TOCSY correlations to H-2 (4.25 ppm), which was consistent with the COZY density (FIG. 16). As a result of reading TOCSY from this second proton (FIG. 16), all other protons of the unit containing methyl were confirmed at 1.28 ppm, which is the overall diagnosis of the pattern of a rhamnose residue. Thus, B was rhamnose α-configured at the anomeric center based on the similarity of the C-5 value thereof (about 70.5 ppm) and the reference glycoside (69.4 or 73.6 ppm for a or β methylglycoside, Bock & Pedersen, 1983), and 3-substituted as defined from the glycosylation shift experienced at the corresponding carbon. The TOCSY pattern of residues C, E, G, and H (H-1 at 5.14, 5.10, 4.97, and 4.88 ppm, respectively) was similar to that of B, and thus they were α-rhamnose units, and the low field value of C-2 (77.8-79.6 ppm) compared to the reference value (71.0 ppm, Bock & Pedersen, 1983) means a substitution at O-2.

For F, H-1 (5.01 ppm) had four TOCSY correlations (FIG. 16), which were attributed to H-2 to H-5 in the COSY spectrum, and is a pattern of a gluco-configured residue. HSQC-TOCSY analysis of H-5 confirmed the correlation with density at 69.5 ppm, which was attributed to C-6 and was in turn related to H-6s (4.14 and 3.96 ppm). Thus, F was determined to be N-acetylglucosamine based on the C-2

(54.9 ppm) and H-2 (3.93 ppm) values and substituted at C-6 (69.4 ppm). The α configuration was inferred by the shape of the anomeric signal (broad singlet) and by the C-3 value (71.8 ppm), which is very similar to the reference α-glycoside (72.0 ppm, Bock & Pedersen, 1983). Finally, H-1 of I (4.50 ppm) had a TOCSY pattern representing all protons of the unit. Thus, based on the $^{13}C$ chemical shifts, I was determined to be glucose substituted at C-3 (82.8 ppm) and R-configured based on the $^3J_{H1,H2}$ value (7.9 Hz).

Figure 18:
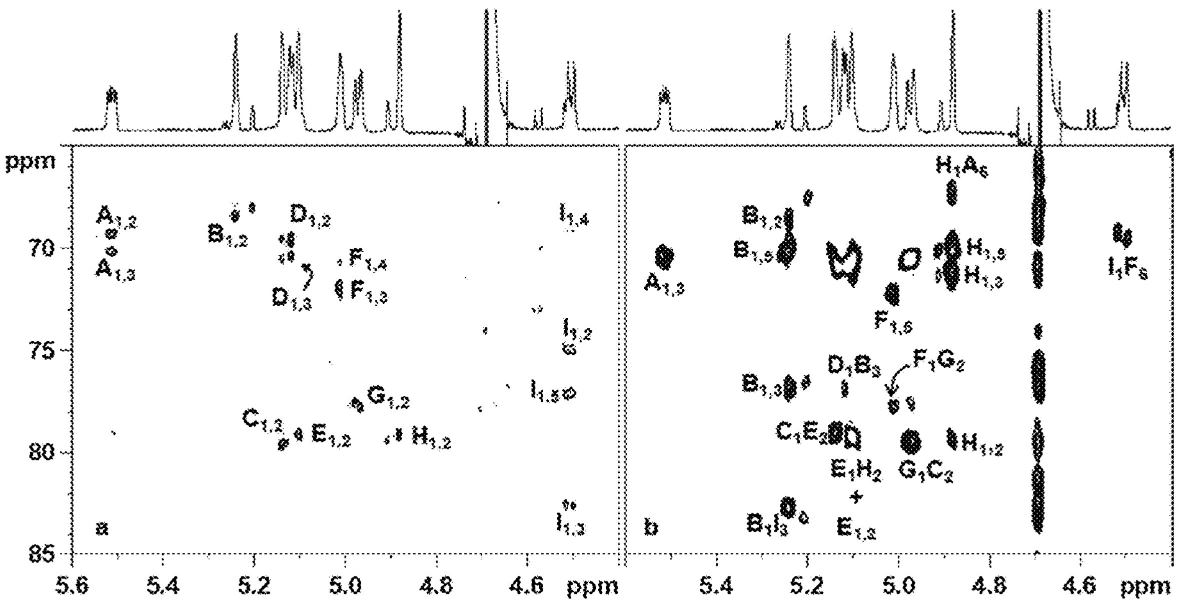
FIG. 18 shows the expansion of HSQC-TOCSY (a) and HMBC (b) NMR spectra recorded for the capsular polysaccharide of *L. plantarum* IMB19 (600 MHz, 310K), with reference to FIG. 20 for the structure of the repeating unit and to Table 3 for labels.
Figure 19:
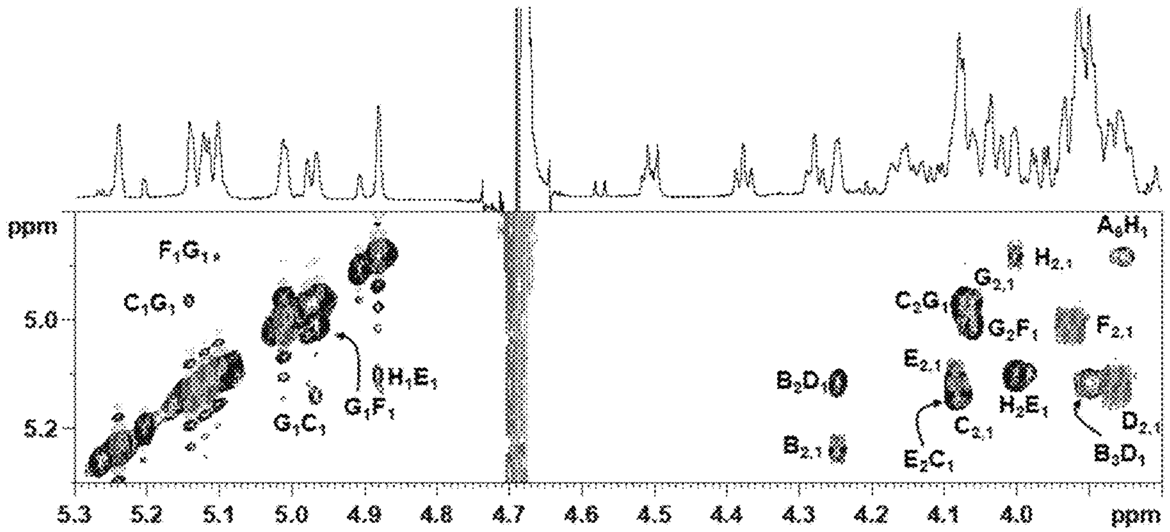
FIG. 19 shows the expansion of NESY (black) and COZY (cyan/red) spectra detailing the H-2 proton region of the residue B-G, which is a part of the capsular polysaccharide, CPS-100, of *L. plantarum* IMB19 (600 MHz, 310K), with reference to FIG. 20 for the structure of the repeating unit and to Table 3 for labels.

The sequences between residues were deduced by analyzing the HMBC (b in FIG. 5) and NOESY (FIG. 4) spectra. First, the correlation of HMBC in which H-1 of B and C-3 of I are connected and the corresponding density were represented as $B_1I_3$ (b in FIG. 18). Other correlations such as $C_1E_2$, $D_1B_3$, $F_1G_2$, $H_1A_6$, and $I_1F_6$ were found in the same manner. In addition, H-1 of E and H-1 of G showed a long-range correlation with carbon at about 79 ppm, which is a value similar to C-2 of C and H. The exact assignment of these densities to $E_1H_2$ and $G_1C_2$ was inferred by analyzing the NOESY spectra associated with H-1 of E and H-2 of H and with H-1 of G and H-2 of C (FIG. 17). These properties were confirmed by observing the reverse correlations detailed in the expansion of H-2 protons of different rhamnose units (FIG. 19).

Figure 20:
FIG. 20 shows the structure of the repeating unit of the capsular polysaccharide, CPS-100, of *L. plantarum* IMB19, in which the number 4 represents the calculated average degree of polymerization, the phosphate group (P) substituted for the oxygen of the 6' carbon residue of D being linked to the 1' carbon of A to indicate a phosphodiester linkage of A and D between the repeating units of the polymerized polysaccharide.

Finally, information that A and D were phosphorylated via a phosphodiester linkage at O-1 and O-6, respectively, explains why HMBC connection did not appear between H-1 of A and C-6 of D, or between H-6 of D and C-1 of A, or why these protons did not have an NOE correlation between the residues. Actually, the HMBC spectrum could not detect any correlation between the two units because the number of linkages between H-1 (or C-1) of A and C-6 (or H-6) of D (5 connections) exceeds the limit of this sequence (3 connections). Similarly, the density of the phosphate moiety between A and D keeps the protons of these units very far apart in order to provide a detectable NOE effect. Therefore, the repeating unit structure of CPS-100 is a nonasaccharide, as reported in FIG. 20.

Figure 21:
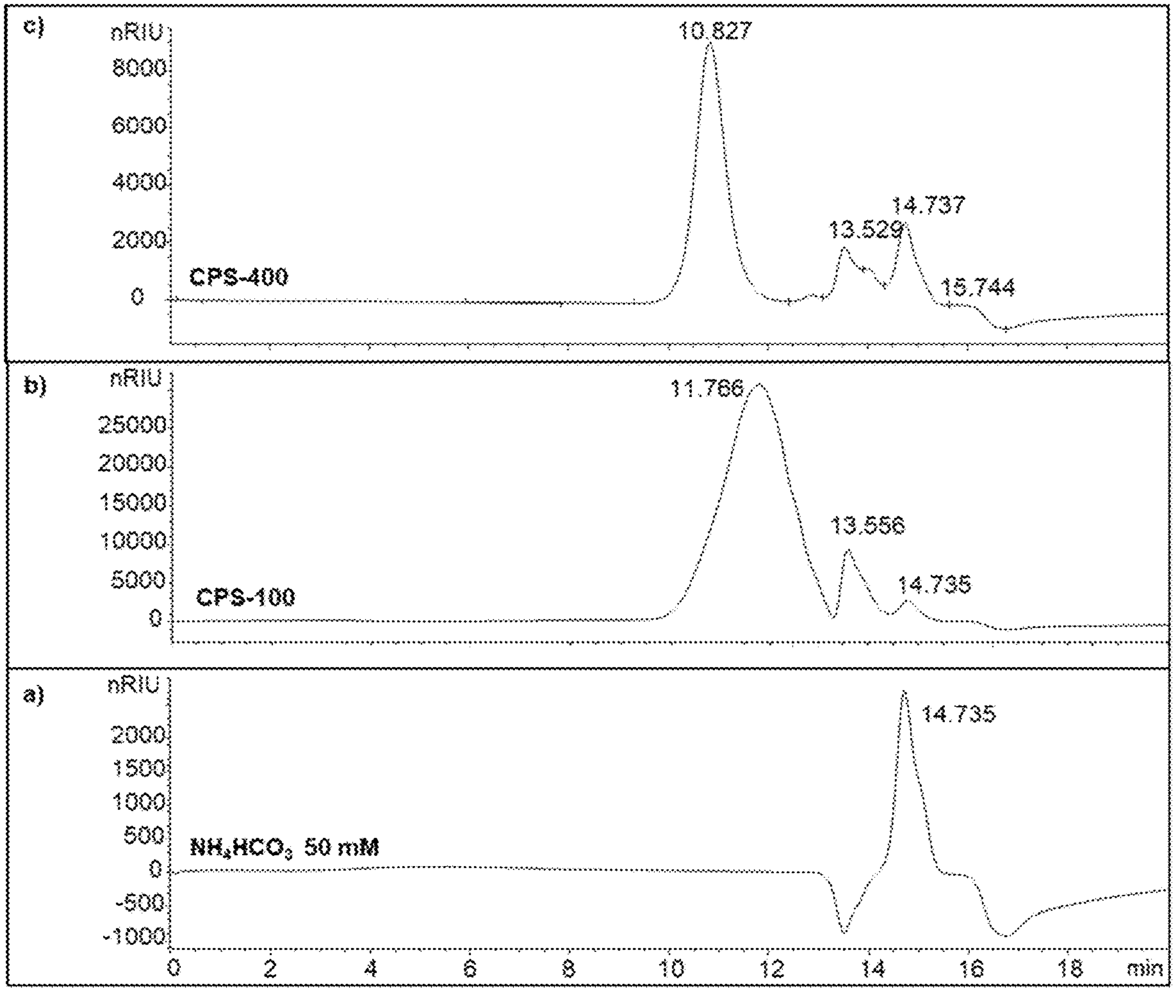
FIG. 21 shows the HPSEC profiles of injection of solvent alone (a), CPS-100 (b), and CPS-400 (c), peaks at 13.6 and 14.74 min being solvent-induced artifacts, as seen in profile (a) of the solvent injected alone.

In addition, minor NMR signals were investigated in order to understand the characteristics thereof. In the HSQC spectrum (FIG. 14), carbon chemical shifts at the indicated densities as Galα and Galβ ($^1H/^{13}C$ 5.26/93.5 and 4.57/97.8 ppm, respectively) show a or β residues in free reduced form. The TOCSY spectrum at H-1 (FIG. 16) showed a typical pattern of galacto-configured sugars (i.e. for Gala, the third density almost overlaps the COZY density). These findings were explained by considering that the procedure used to isolate CPS included sonication and trichloroacetic acid treatment, both able to induce some cleavage of the phosphodiester linkage, especially in the anomeric phosphate of galactose A because of the extreme lability of this linkage. Therefore, it was expected that the minor signal next to the intense signal (FIG. 14, indicated by "*") belongs to the first repeating residue and is linked to galactose in a free reduced form. However, the low intensity and dense carbinolic region thereof prevented accurate identification of the properties thereof. Finally, in the HSQC spectrum (a in FIG. 14), integrating the anomeric density, the sample has an average degree of polymerization of 4 and an average MW of about 6 kDa (the MW of the repeating unit is 1500 Da), in which 11 kDa, calculated based on HPSEC, appears to be a somewhat high estimate (FIG. 21).

Example 11: NMR Analysis of CPS-400

Structural characteristics of CPS-400 were analyzed in a manner similar to the description of the above example (Table 4).

TABLE 4

(600 MHz, 310K) NMR data of CPS-400. Position 1 of ribitol (or glycerol) points to the right; the "motif" column depicts the structure of the unit and, in case of substituted Rbo or Gro units, it indicates the nature of the substituent and specifies its position.

| Residue | motif | 1 | 2 | 3 | 4 | 5 | 6 |
|---|---|---|---|---|---|---|---|
| A | 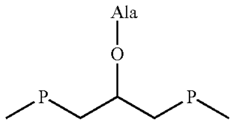 | 4.11 × 2 | 5.39 | 4.11 × 2 | — | — | — |
| Gro | Ala | 65.0 | 75.5 | 65.0 | — | — | — |
| B | 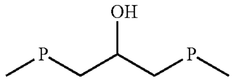 | 3.96; 3.89 | 4.05 | 3.89; 3.96 | — | — | — |
| Gro | | 67.5 | 70.8 | 67.5 | — | — | — |
| C | 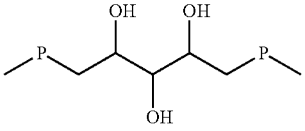 | 4.09; 4.00 | 3.99 | 3.81 | 3.99 | 4.09; 4.00 | — |
| Rbo | | 67.8 | 72.2 | 72.5 | 72.1 | 67.8 | — |
| D* | 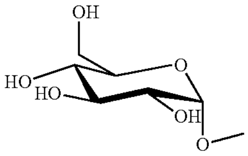 | 5.17 | 3.57 | 3.80 | 3.43 | 4.00 | 3.90; 3.78 |
| t-α-Glc | | 98.4 | 72.8 | 74.2 | 70.8 | 72.8 | 61.8 |

TABLE 4-continued (600 MHz, 310K) NMR data of CPS-400. Position 1 of ribitol (or glycerol) points to the right; the "motif" column depicts the structure of the unit and, in case of substituted Rbo or Gro units, it indicates the nature of the substituent and specifies its position.

| Residue | motif | 1 | 2 | 3 | 4 | 5 | 6 |
|---|---|---|---|---|---|---|---|
| E*<br>t-α-Glc | 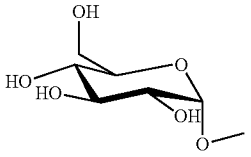 | 5.17<br>99.0 | 3.54<br>72.7 | 3.76<br>74.2 | 3.42<br>71.0 | 3.92<br>73.1 | 3.90; 3.78<br>61.8 |
| F*<br>t-α-Glc | 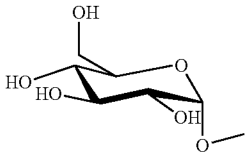 | 5.10<br>101.5 | 3.58<br>72.8 | 3.69<br>73.8 | 3.43<br>70.9 | 3.89<br>74.0 | 3.90; 3.78<br>61.8 |
| F'* | 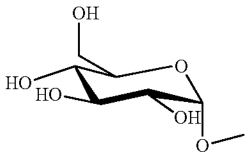 | 5.11<br>98.7 | 3.58<br>72.8 | 3.79<br>74.2 | 3.43<br>70.9 | 4.00<br>72.8 | 3.90; 3.78<br>61.8 |
| G | 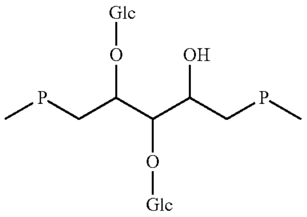 | 4.16 x 2 | 4.15 | 3.97 | 4.30 | 4.14 x 2 | |
| Rbo | (3F; 4D) | 67.7 | 70.5 | 80.6 | 78.3 | 66.9 | |
| H | 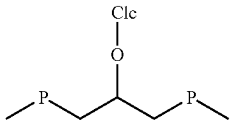 | 4.02** | 4.11 | 4.05; 4.00** | | | |
| Gro | 2E | 67.7 | 76.6 | 66.4 | | | |
| I | 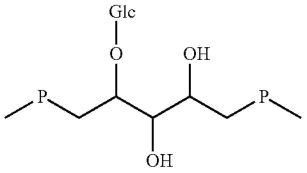 | 4.09; 4.00 | 3.92 | 3.99 | 4.12 | 4.15; 4.12 | |
| Rbo | 4F' | 67.8 | 71.2 | 70.9 | 79.0 | 65.8 | |
| Ala | | —<br>171.3 | 4.30<br>50.2 | 1.64<br>16.5 | | | |

*For all these residues, the H-6/C-6 are coincident.

**attributions can be reserved.

Figure 22:
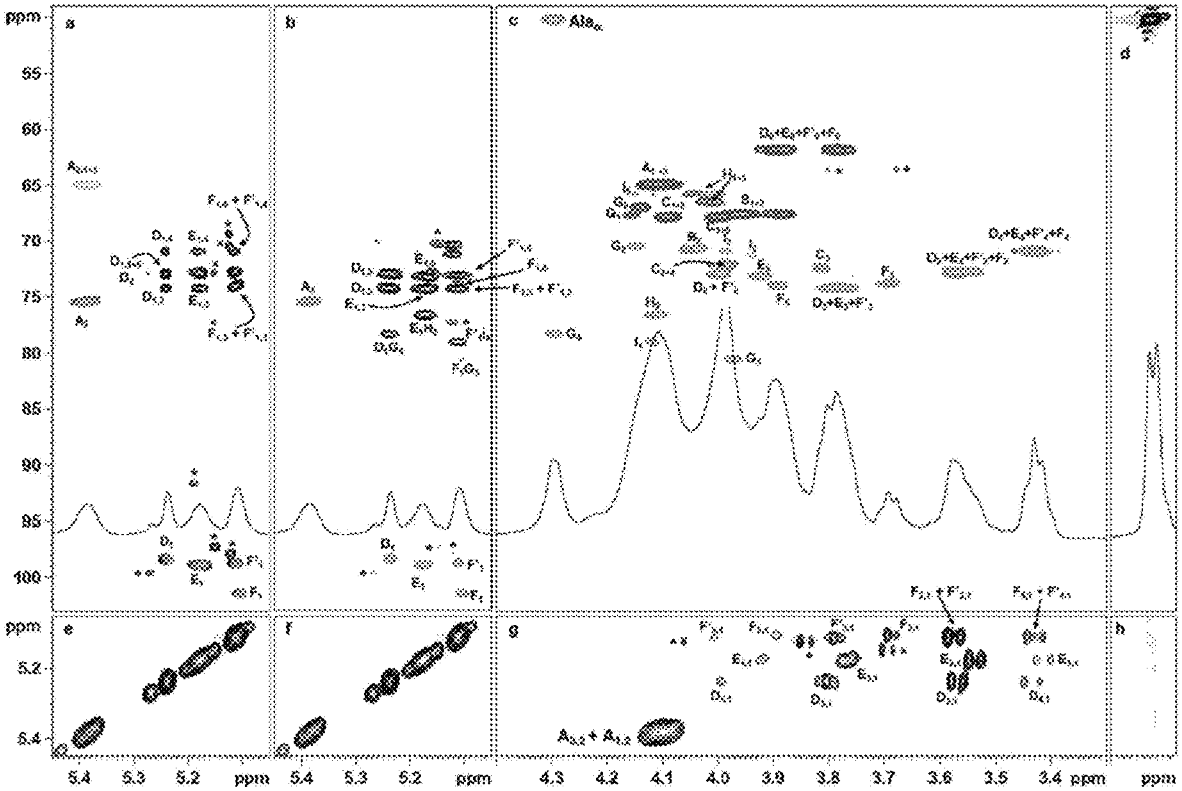
FIG. 22 shows the NMR spectra recorded for the CPS-400 (600 MHz, 310K): (a) overlay of HSQC-TOCSY (black) and HSQC (cyan), (b) overlay of HMBC (black) and HSQC (cyan), (c) HSQC, (d) HSQC-TOCSY, and (e) to (h) TOCSY spectra of different regions, "*" denoting the density belonging to an unidentified minor motif, and labels and depictions of structural units being shown in Table 4.

First, the anomeric region of the HSQC spectrum (a and b in FIG. 22) showed several residues, in which the signals at $^{1}$H 5.3-5.1 ppm occurred at monosaccharide residues, whereas the signals at $^{1}$H/$^{13}$C 5.39/75.5 ppm were not anomeric but were C-2 of the glycerol unit (Gro), denoted as A, and were shifted to the lower field due to acylation. The substituent at O-2 was alanine (Ala), identified by methyl at $^{1}$H/$^{13}$C 1.64/16.5 ppm and Ha/Ca at 4.30/50.2 ppm. In addition, H-1/C-1 and H-3/C-3 of A were equivalent, and identified at 4.11/65.0 ppm based on the corresponding HSQC-TOCSY (a in FIG. 22) and TOCSY (g in FIG. 22) correlations.

Finally, the C-1 (or C-3) value indicates that a second 1,3-diphosphorylated Gro unit (B) and a 1,5-diphosphorylated ribitol unit (Rbo, C) were identified in HSQC analysis, for which reference may be made to Gerlach et al., 2018, which showed that A was phosphorylated at both ends, as in the case of Gro-type teichoic acid, and this last residue implies the presence of another teichoic acid based on the ribitol-phosphate backbone. For monosaccharide units, the analysis focused on the most intense signals (D, E, F' and F) identified as α-glucose units based on the efficient propagation of magnetization up to H-6 in the anomeric signal of the TOCSY spectrum. These Glc units were no longer substituted based on the similarity of $^{13}C$ chemical shifts (Bock & Pedersen, 1983).

Figure 23:
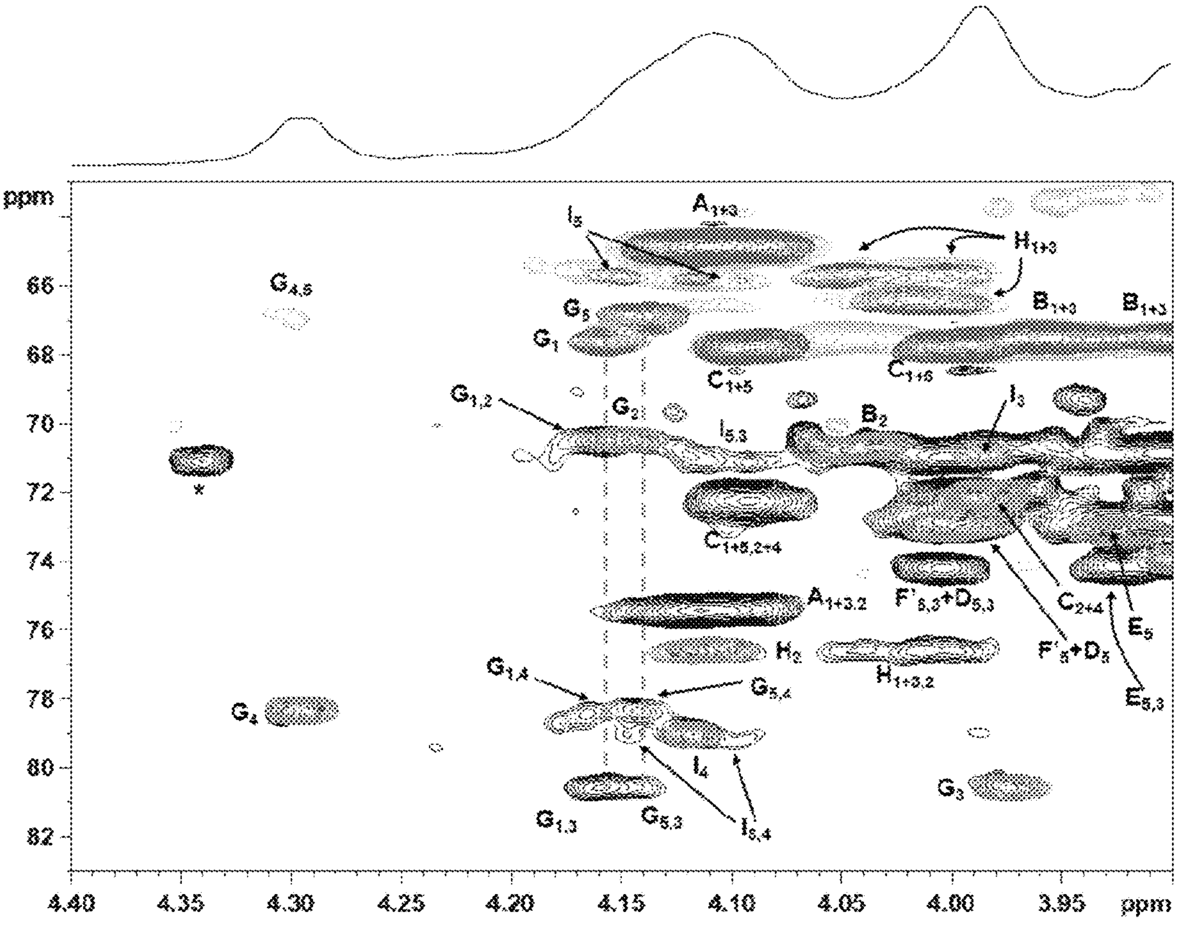
FIG. 23 shows the expansion of HSQC-TOCSY (black/grey) and HSQC (cyan/red) depicting the density of ribitol G, in which the HSQC-TOCSY correlation from G1 and G5 is indicated by the grey dashed line, and labels and depictions of structural units are shown in Table 4 (600 MHz, 310K)

The location of these units was deduced through HMBC spectral analysis and comparison with data from references. Indeed, E was linked to O-2 of the Gro unit (H) (Shashkov, Potekina, Senchenkova, & Kudryashova, 2009), whereas F' was linked to O-4 of the Rbo unit (I) (Streshinskaya et al., 2011). For D, H-1 had a long-range correlation with carbon at 78.3 ppm (b in FIG. 18) in which the proton (4.30 ppm) was linked to "$CH_2$" at 69.9 ppm in the HSQC-TOCSY spectrum (FIG. 23). This new unit was denoted as G, and densities at $^1H/^{13}C$ 4.30/78.3 and 4.14/66.9 ppm were assigned to G4 and G5 (c in FIG. 18; FIG. 23). G was identified as ribitol, and other signals were found through HSQC-TOCSY spectral analysis. Actually, the "$CH_2$" density at $^1H/^{13}C$ 4.16/67.7 ppm had three correlations with the signal indicating G4, and this density was denoted as G1. In addition, C-1 of G (67.7 ppm) represents carbon that is not glycosylated but is phosphorylated at the adjacent position, as reported for I. This information led to the assignment of the remaining two HSQC-TOCSY correlations to C-2 (70.5 ppm) and C-3 (80.6 ppm), and the corresponding H-2 (4.15 ppm) and H-3 (3.97 ppm) were identified in turn in the HSQC spectrum (FIG. 18, FIG. 23, and Table 4). Thus, G is Rbo glycosylated at O-3 and O-4, with the two units, F and D (HMBC in b in FIG. 22), attached thereto.

This type of substitution was identified in other *Lactobacillus plantarum* strains, but NMR data thereof reported phosphate-free Rbo units, so these chemical shifts could not be compared with the data of the present invention (Tomita et al., 2017). However, the results of the present invention were similar to those of teichoic acids of *Bifidobacterium* (Valueva et al., 2013), which suggested a reverse substitution pattern of ribitol having glucose units linked at C-2 and C-3 (Valueva et al., 2013). Interestingly, NMR data of the dephosphorylated form, reported by Valueva et al. (2013), coincided with the NMR data of 3,4-diglucosylated ribitol reported by Tomita et al. (2009). Accordingly, the substitution pattern (2,3 or 3,4) of ribitol units has not yet been clearly defined. Therefore, the NMR data of the present invention indicate that CPS-400 is a mixture of two teichoic acids of Gro- and Rbo-type, each showing the presence of several substituents in a non-stoichiometric manner. For Gro-type TA, the non-stoichiometric substituents were alanine and α-glucose. For Rbo-type TA, α-glucose did not occur at both 03 and 04 of ribitol, at 04 alone, or at any position. An attempt was made to separate the two TAs through size exclusion chromatography, but CPS-400 appeared as a symmetrical peak of about 45 kDa (FIG. 21), and was not separable any further.

Example 12: Immunostimulatory Activity of CPS-100 and CPS-400

The activity of CPS-100 and CPS-400 on the immune response was confirmed.

Figure 24:
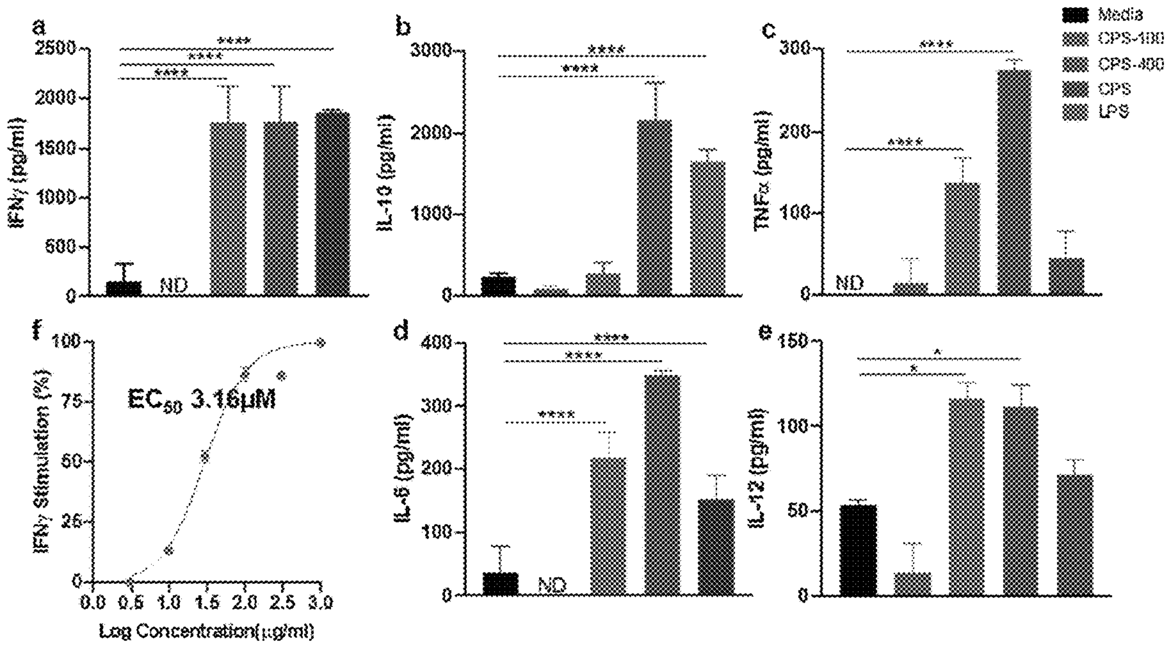
FIG. 24 shows results confirming the levels of cytokines in order to confirm immunostimulatory activity of the capsular polysaccharide in the purified fraction, in which splenocytes were cultured in the presence of medium (control), CPS fractions (CPS-400 and CPS-100, 50 μg/mL), total CPS (50 μg/mL), and lipopolysaccharide (LPS from *E. coli* 0111:B4, 0.1 μg/mL), as shown in FIG. 24, and the cell culture supernatants were analyzed through ELISA for evaluation of cytokine production, with dose response curves of CPS-100 for the production of (a) IFNγ, (b) IL-10, (c) TNF-α, (d) IL-6, (e) IL-12, and (f) IFNγ, in which, in (f), EC50 (half-maximal effective concentration) was calculated to be 3.16 μM, data being values from two to three independent experiments with similar results, all bar graphs indicating mean±SD, *p<0.05, ****p<0.0001 (one-way ANOVA with post hoc Dunnett's test for multiple comparisons) and ND, not detected.

The effect of CPS on the immune system was confirmed using splenocytes in which all immune cells were mixed at a physiological ratio. Endpoint analysis was performed by testing different cytokines through ELISA. Cytokines are a group of secretory peptides/glycoproteins involved in cell signaling that mediates and modulates inflammatory or tolerant immune responses in vivo. Thus, when exposed to CPS, skewing of cytokines in the immune cell pool implies a similar role in vivo. In order to confirm the immune response generated by CPS-100 and CPS-400, analysis was performed using interferon-gamma (IFN-γ) as an inflammatory marker and interleukin-10 (IL-10) as a regulatory cytokine. The study results indicate that CPS-100 is immunostimulatory, as shown by high IFN-γ and negligible IL-10 production (a and b in FIG. 24). On the other hand, IFN-γ was not detected at any level in CPS-400, which is the TA fraction (a in FIG. 24). Under similar conditions, other cytokines including TNF-α (tumor necrosis factor-α), IL-6 (interleukin 6), IL-12 (interleukin 12), IL-17 (interleukin 17), and IL1-β (interleukin 1β) were assessed.

CPS-100 stimulated cells to produce very high levels of TNF-α, IL-6, and IL-12 (c to e in FIG. 24), whereas IL-17 and IL1-β were not detected. On the other hand, CPS-400 did not show a significant increase in any of the measured cytokines (c and e in FIG. 24). Since IFN-γ is a primary immunostimulatory marker produced by various types of immune cells, in order to confirm the specificity of the immunostimulatory response of CPS, whether production of IFN-γ was dependent on the concentration of CPS-100 was evaluated. During induction of IFN-γ for 48 hours, the half-maximal effective concentration (EC50) of CPS-100 was 3.16 μM (f in FIG. 24), indicating that CPS-100 can be used as an effective immune stimulant.

Consequently, CPS-100 exhibits immunostimulatory properties similar to those of the *L. plantarum* IMB19 strain, which means that the effective molecule exhibiting the immune-enhancing activity of the *L. plantarum* IMB19 strain is CPS-100.

Figure 25:
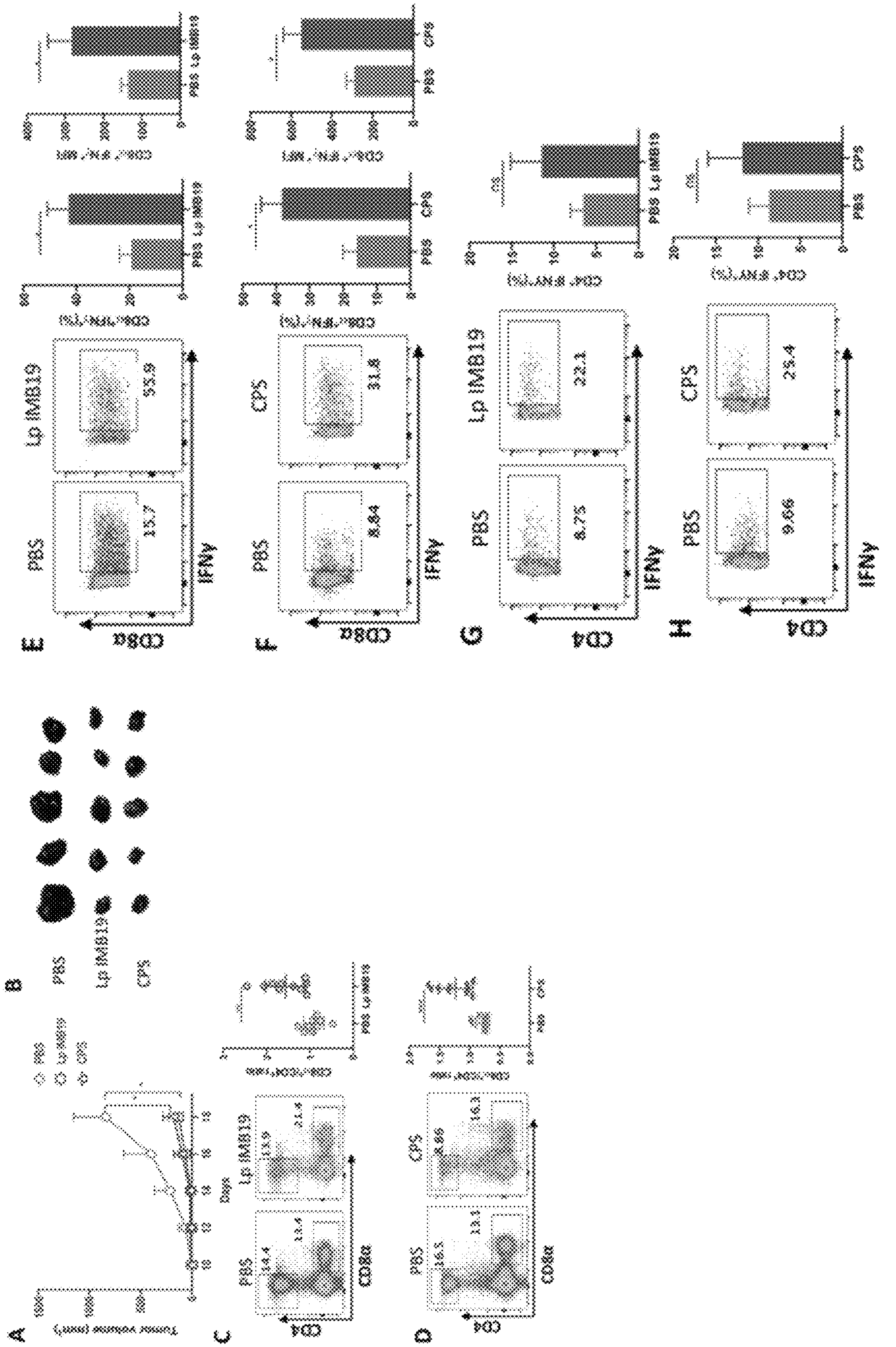
FIG. 25 shows the tumor growth inhibitory effects of *L. plantarum* IMB 19 and CPS through activation of CD8+ T cells and improvement of intratumoral infiltration, with A showing B16.F10 melanoma growth kinetics in C57/Bi6

Example 13: Improvement of CD8+ T-Cell Function and Anti-Tumor Immunity Effect of *L. plantarum* IMB19 and CPS Whether the activity of CPS as an immune stimulant in vitro is able to lead to tumor-suppressing activity in vivo was evaluated. It was confirmed that the growth of subcutaneous melanoma was significantly reduced in treatment groups orally administered with *L. plantarum* IMB19 and intraperitoneally administered with CPS (FIGS. 25A and 25B). Delayed tumor growth in both groups was associated with infiltration of CD8+ T cells (C in FIG. 25). The production and increased frequency of IFN-γ by the tumor-infiltrating CD8+ T cells mean that the cytotoxic activity of the CD8+ T cells was greatly increased due to the above administration (E and F in FIG. 25). Intratumoral CD4+ T cells also showed upregulation of IFN-γ production in both treatment groups (G and H in FIG. 25G). In contrast, there was no difference in the intratumoral Treg population compared to the PBS-administered group (A and B in FIG. 26). Oral administration of *L. plantarum* IMB19 modulated tumor growth in EMT-6 breast cancer (FIG. 27). Consequently, these data suggest that CPS and *L. plantarum* IMB19 enhance anti-tumor immune activity of inhibiting cancer growth.

Example 14: Increased Intratumoral Macrophage Infiltration of CPS

CPS increases macrophage infiltration in tumors. In order to identify specific APC types modulating CD8+ T-cell responses, intraperitoneal administration of CPS was performed, B16.F10 melanoma cells were inoculated, and infiltration of APCs in early tumors was assessed. CPS mainly increased the frequency of CD11c+ CD11b+ macrophages in tumors compared to CD11c+ DCs (A in FIG.

28). The number of macrophages was confirmed to be very high in CPS-administered mice through flow cytometry (A in FIG. 28). Under the same conditions, activation markers of CD11c+ CD11b+ macrophages and CD11c+ dendritic cells were identified. Surprisingly, the activation state of CPS-treated dendritic cells did not show a significant difference from the control group (C in FIG. 28). However, macrophages were more strongly activated and showed higher expression of CD11b, MHC I, MHC II, CD86, and CD40 (B in FIG. 28). In order to confirm activation of the systemic adaptive immune system in the same mice, CD69, which is a marker of early activation of CD8+ T cells, was identified in draining lymph nodes. Compared with the control group, CD69 was clearly and significantly upregulated due to CPS administration (D in FIG. 28). These data suggest that CPS plays an important role in the activation of macrophages and is able to limit tumor growth.

Example 15: Differentiation of Macrophages into Inflammatory Macrophages and Macrophage Reprogramming from M2 to M1 Phenotype by CPS In order to characterize the effect of CPS on macrophages, changes in phenotype when macrophages were exposed to CPS were confirmed. Peritoneal CD11b+ F4/80+ macrophages displayed an activated phenotype when treated with CPS, and significant upregulation of MHC I, MHC II, CD68, iNOS2, and CD40 appeared in CPS-treated macrophages compared to LPS- or Pam3CSK4-treated macrophages (E in FIG. 28), so an M1 phenotype or an inflammatory phenotype of macrophages was indicated. In particular, similar to Pam3CSK4, TLR2 was upregulated upon CPS treatment, suggesting that CPS may be a TLR2 ligand. However, in contrast to the in-vivo experiments, the expression of CD80 and CD86 was not altered (E in FIG. 28).

Alternatively activated macrophages or M2-phenotype macrophages significantly contribute to immune suppression and enhance tumor growth (Ann. Oncol. 28, xii18-xii32 (2017)) (Front Oncol. 9, 421 (2019)). Thus, these results indicate that CPS in tumors is able to reprogram M2 macrophages to the M1 phenotype. Indeed, the number of IL-4-induced M2-phenotype peritoneal macrophages was significantly increased when using CPS compared to when using LPS and Pam3CSK4 (F in FIG. 28). In addition, the inflammatory macrophage marker iNOS2 was significantly upregulated independently of MHC I, MHC II, CD40, and CD68 (F in FIG. 28). These data imply that CPS treatment produces inflammatory macrophages and reprograms immunosuppressive macrophages to an immunostimulatory phenotype.

Although specific embodiments of the present invention have been disclosed in detail above, it will be obvious to those of ordinary skill in the art that the description is merely of preferable exemplary embodiments, and is not to be construed as limiting the scope of the present invention. Therefore, the substantial scope of the present invention will be defined by the appended claims and equivalents thereof.

Accession Number

Name of depository institution: Korea Institute of Biotechnology and Biotechnology Accession number: KCTC14337BP Deposit Date: 2020 Oct. 21

INDUSTRIAL APPLICABILITY

According to the present invention, a novel *Lactobacillus plantarum* IMB19 strain and a polysaccharide derived from the strain exhibit strong ability to stimulate CD8+ T-cell activity and excellent Treg cell inhibitory activity, and stimulate and enhance anti-tumor immune responses through various mechanisms such as increased intratumoral macrophage infiltration of CPS and differentiation/reprogramming of macrophages to an inflammatory (M1) phenotype. Therefore, the strain and the strain-derived polysaccharide according to the present invention can be useful for immune modulation in a subject, particularly for immune enhancement, and are capable of inducing and improving anti-tumor immune responses, thereby inhibiting tumor growth. The novel strain and the strain-derived polysaccharide according to the present invention are useful for the prevention, amelioration, or treatment of, for example, tumors, infectious diseases, and various immune diseases caused by or symptomatic of immune dysfunction.

SEQUENCE LIST FREE TEXT

An electronic file is attached.

What is claimed is:

1. A method of immune modulation, comprising administering a *Lactobacillus plantarum* IMB19 strain having accession number KCTC 14337BP or a capsular polysaccharide derived from the strain to a subject.

2. The method according to claim 1, wherein the immune modulation is enhancement of immunity.

3. A method of immune modulation comprising administering a polysaccharide represented by Formula I below to a subject:

-[-D-B-I-F-G-C-E-H-A-]$_n$- [Formula I]

in Formula I,

A and D are galactose,

B, C, E, G, and H are rhamnose,

F is N-acetylglucosamine,

I is glucose, and n is an integer of 1 or more.

4. The method according to claim 3, wherein galactose of at least one of A and D is phosphorylated.

5. The method according to claim 4, wherein a hydroxyl group (—OH) of carbon at position 1 of A is phosphorylated.

6. The method according to claim 4, wherein a hydroxyl group (—OH) of carbon at position 6 of D is phosphorylated.

7. The method according to claim 3, wherein n is 2 or more, and A and D of repeating units are connected through a phosphodiester linkage.

8. The method according to claim 3, wherein, in Formula I,

D and B; and B and I are connected through an α-1,3-glycosidic linkage,

I and F are connected through a β-1,6-glycosidic linkage,

F and G; G and C; C and E; and E and H are connected through an α-1,2-glycosidic linkage, and H and A are connected through an α-1,6-glycosidic linkage.

9. The method according to claim 3, wherein the polysaccharide has a structure of Formula II below:

[Formula II]

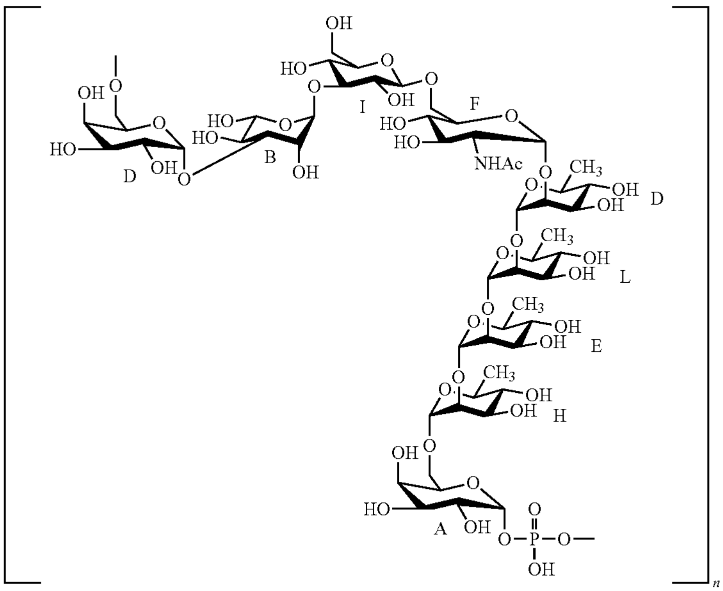

n being an integer of 1 or more.

10. The method according to claim 3, wherein the immune modulation is enhancement of immunity.

11. The method according to claim 1, wherein a tumor or an infectious disease in the subject is treated by the administered strain or capsular polysaccharide.

12. The method according to claim 3, wherein a tumor or an infectious disease in the subject is treated by the administered polysaccharide.

13. The method according to claim 1, wherein the strain or capsular polysaccharide is administered in a food composition comprising the strain or capsular polysaccharide.

14. The method according to claim 3, wherein the polysaccharide is administered in a food composition comprising the polysaccharide.

15. A method of producing inflammatory T cells, comprising:

(a) priming antigen-presenting cells with a *Lactobacillus plantarum* IMB19 strain having accession number KCTC 14337BP or a polysaccharide represented by Formula I below:

-[-D-B-I-F-G-C-E-H-A-]$_n$- [Formula I]

in Formula I,

A and D are galactose,

B, C, E, G, and H are rhamnose,

F is N-acetylglucosamine,

I is glucose, and n is an integer of 1 or more; and (b) co-culturing the primed antigen-presenting cells with T cells.

16. The method according to claim 15, wherein the antigen-presenting cells are selected from the group consisting of macrophages, B cells, dendritic cells (DCs), and Langerhans cells.

17. The method according to claim 15, wherein the inflammatory T cells are cytotoxic T cells or helper T cells.

18. A method of producing M1-phenotype macrophages, comprising:

differentiating macrophages into M1-phenotype macrophages by treating macrophages with a *Lactobacillus plantarum* IMB19 strain having accession number KCTC 14337BP or a polysaccharide represented by Formula I below:

-[-D-B-I-F-G-C-E-H-A-]$_n$- [Formula I]

in Formula I,

A and D are galactose,

B, C, E, G, and H are rhamnose,

F is N-acetylglucosamine,

I is glucose, and n is an integer of 1 or more; and obtaining the differentiated M1-phenotype macrophages.

19. The method according to claim 18, wherein in the M1-phenotype macrophages, expression of at least one selected from the group consisting of MHC I, MHC II, CD68, iNOS2, and CD40 is upregulated.

* * * * *

UNITED STATES PATENT AND TRADEMARK OFFICE

CERTIFICATE OF CORRECTION

PATENT NO. : 11,690,884 B2
APPLICATION NO. : 17/811542
DATED : July 4, 2023
INVENTOR(S) : Sin-Hyeog Im et al.

It is certified that error appears in the above-identified patent and that said Letters Patent is hereby corrected as shown below:

In the Specification

Column 40, Line 52, "for a or" should be -- for α or --.
Column 41, Line 9, "R-configured" should be -- β-configured --.
Column 42, Line 9, "a or β residues" should be -- α or β residues --.
Column 42, Line 11, "Gala" should be -- Galα --.
Column 43, Line 66, "Ha/Ca" should be -- Hα/Cα --.
Column 45, Line 50, "03 and 04 of ribitol, at 04 alone" should be -- O3 and O4 of ribitol, at O4 alone --.

Signed and Sealed this
Twenty-second Day of August, 2023

Katherine Kelly Vidal

Katherine Kelly Vidal
*Director of the United States Patent and Trademark Office*